(12) United States Patent
Margiott et al.

(10) Patent No.: US 12,727,797 B2
(45) Date of Patent: *Sep. 8, 2026

(54) WIRELESS OXYGEN SATURATION MEASUREMENT KIT

(71) Applicant: ViOptix, Inc., Newark, CA (US)

(72) Inventors: Alex Michael Margiott, Dunbarton, NH (US); Steven J. Kuhn, Santa Clara, CA (US); Maw-Lin Kuo, Fremont, CA (US); Cameran Casale, Berkeley, CA (US); Vittorio Martinet, Brooklyn, NY (US); Robert John de Saint Phalle, Marblehead, MA (US); Dickshitha Thyagharajon, Fremont, CA (US); Tanmay Mahendra Kothale, Mountain View, CA (US); Lilit Karayan, Sunnyvale, CA (US); Hristo Stoytchev, San Carlos, CA (US); Timothy Buskard, Livermore, CA (US); Shaheen Jeeawoody, Hayward, CA (US); Mark Lonsinger, San Jose, CA (US); Scott E. Coleridge, New York, NY (US)

(73) Assignee: ViOptix, Inc., Newark, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/460,221

(22) Filed: Jan. 26, 2026

(65) Prior Publication Data

US 2026/0215705 A1 Jul. 30, 2026

Related U.S. Application Data

(60) Provisional application No. 63/749,480, filed on Jan. 24, 2025.

(51) Int. Cl.
*A61B 5/1455* (2006.01)
*A61B 5/00* (2006.01)

(52) U.S. Cl.
CPC ........ *A61B 5/14551* (2013.01); *A61B 5/0002* (2013.01); *A61B 2560/0214* (2013.01)

(58) Field of Classification Search
CPC .................................................... A61B 5/1455
See application file for complete search history.

(56) References Cited

U.S. PATENT DOCUMENTS 6,134,460 A 10/2000 Chance
6,748,254 B2 6/2004 O'Neil et al.

(Continued)

FOREIGN PATENT DOCUMENTS

CN 108344524 B 8/2021
JP 4465271 B2 5/2010

(Continued)

OTHER PUBLICATIONS

Amiri, A.R., et al., Intraoperative Assessment of Human Spinal Cord Perfusion using near Infrared Spectroscopy with Indocyanine Green Tracer Technique, Spine J., Dec. 2013, 13(12), pp. 1818-1825.

(Continued)

*Primary Examiner* — Marjan Fardanesh
(74) *Attorney, Agent, or Firm* — Aka Chan LLP

(57) ABSTRACT

An oximeter device includes a sensor probe unit that is connected by a wire to a sensor probe electronic module. The sensor probe electronic module connects wirelessly to a medical device console, which can be a phone, tablet, or other mobile device. And the mobile device can connect to a network or the Internet (e.g., the Cloud). Alternatively, the sensor probe electronic module can directly to the network or the Internet directly without a medical device console.

(Continued)

The medical device console can execute an application and show on its display oxygen saturation and related measurements obtained through the sensor probe unit.

20 Claims, 39 Drawing Sheets

(56) References Cited

U.S. PATENT DOCUMENTS

| | | | |
|---|---|---|---|
| 7,355,688 | B2 | 4/2008 | Lash et al. |
| 7,525,647 | B2 | 4/2009 | Lash et al. |
| 7,538,865 | B2 | 5/2009 | Lash et al. |
| 7,657,293 | B2 | 2/2010 | Lash et al. |
| 7,796,247 | B2 | 9/2010 | Mao et al. |
| 8,052,605 | B2 | 11/2011 | Muller et al. |
| 8,308,784 | B2 | 11/2012 | Streeter et al. |
| 8,315,685 | B2 | 11/2012 | Arizaga Ballesteros |
| 8,352,006 | B1 | 1/2013 | Elmandjra et al. |
| 8,622,918 | B1 | 1/2014 | Mao et al. |
| 8,929,967 | B2 | 1/2015 | Mao et al. |
| 9,591,999 | B2 | 3/2017 | Schenkman et al. |
| 10,028,682 | B2 | 7/2018 | Thiele |
| 10,188,872 | B2 | 1/2019 | De Taboada et al. |
| 10,209,178 | B2 | 2/2019 | Carvalho Sousa et al. |
| 10,321,862 | B2 | 6/2019 | Dalene et al. |
| 10,335,074 | B2 | 7/2019 | Mao et al. |
| 10,548,526 | B1 | 2/2020 | Mao et al. |
| 10,758,743 | B2 | 9/2020 | De Taboada et al. |
| 11,273,319 | B2 | 3/2022 | De Taboada et al. |
| 11,662,309 | B2 | 5/2023 | Magnussen et al. |
| 12,514,474 | B2 | 1/2026 | Shadgan et al. |
| 2007/0078316 | A1 | 4/2007 | Hoarau et al. |
| 2007/0093698 | A1 | 4/2007 | Goldberger et al. |
| 2009/0163775 | A1 | 6/2009 | Barrett et al. |
| 2010/0105998 | A1 | 4/2010 | Benni |
| 2011/0060266 | A1 | 3/2011 | Streeter et al. |
| 2013/0225955 | A1 | 8/2013 | Schenkman et al. |
| 2014/0276014 | A1 | 9/2014 | Khanicheh et al. |
| 2014/0343384 | A1 | 11/2014 | Floyed et al. |
| 2015/0265214 | A1 | 9/2015 | De Kok et al. |
| 2015/0282747 | A1 | 10/2015 | Thiele |
| 2016/0235303 | A1 | 8/2016 | Fleming et al. |
| 2016/0278675 | A1 | 9/2016 | Benni |
| 2017/0209083 | A1 | 7/2017 | Zarandi et al. |
| 2017/0215780 | A1 | 8/2017 | Mao et al. |
| 2018/0042513 | A1 | 2/2018 | Connor |
| 2018/0214026 | A1 | 8/2018 | Goodall et al. |
| 2018/0214066 | A1 | 8/2018 | Goodall et al. |
| 2019/0150811 | A1 | 5/2019 | Evans et al. |
| 2019/0234869 | A1 | 8/2019 | Sajjadi et al. |
| 2019/0254536 | A1 | 8/2019 | Nahman et al. |
| 2021/0259618 | A1 | 8/2021 | Seidman et al. |
| 2022/0218272 | A1 | 7/2022 | Pollonini et al. |
| 2024/0000383 | A1 | 1/2024 | Connor |
| 2025/0241564 | A1 | 7/2025 | Margiott et al. |

FOREIGN PATENT DOCUMENTS

| | | | |
|---|---|---|---|
| KR | 102000866 | B1 | 7/2019 |
| WO | 2012109661 | A2 | 8/2012 |
| WO | 2013166461 | A1 | 11/2013 |
| WO | 2018168145 | A1 | 9/2018 |
| WO | 2021042215 | A1 | 3/2021 |

OTHER PUBLICATIONS

Arifler, D., et al., Optimal Wavelength Combinations for Near-Infrared Spectroscopic Monitoring of Changes in Brain Tissue Hemoglobin and Cytochrome C Oxidase Concentrations, Biomed Opt Express, Mar. 1, 2015, 6(3), pp. 933-947.

Boushel, R., et al., Monitoring Tissue Oxygen Availability with near Infrared Spectroscopy (NIRS) in Health and Disease, Scand J Med Sci Sports, 2001: 11, pp. 213-222.

Busch, D.R. et al., Laser Safety in Fiber-Optic Monitoring of Spinal Cord Hemodynamics: A Preclinical Evaluation, J Biomed Opt, 2018, 23:065003.

Casha, S., et al., A Systematic Review of Intensive Cardiopulmonary Management after Spinal Cord Injury, J Neurotrauma, 2011, 28, pp. 1479-1495.

Delphy, D. T., et al., Quantification in tissue near-infrared spectroscopy, Phil. Trans. R. Soc. Lond. B 1997, 352, pp. 649-659.

Demir, A. et al., Near-infrared Spectroscopy Monitoring of the Spinal Cord during Type B Aortic Dissection Surgery, J Card Surg., May 2013, 28(3), pp. 291-294.

Dix, L.M.L., et al., Monitoring Cerebral Oxygenation in Neonates: An Update, Frontiers in Pediatrics, vol. 5(46), Mar. 14, 2017, doi: 10.3389/pfed.2017.00046, 9 pgs.

Etz, D.C., et al., Spinal Cord Ischemia in Open and Endovascular Thoracoabdominal Aortic Aneurysm Repair: New Concepts, J Cardiovasc Surg (Torino), Apr. 2014: 55(2 Suppl 1), pp. 159-168.

Hawryluk, G., et al., Mean Arterial Blood Pressure Correlates with Nuerological Recovery after Human Spinal Cord Injury: Analysis of High Frequency Physiologic Data, Journal of Neurotrauma, 32:1958-1967, Dec. 15, 2015.

Kogler, A.S., et al., Fiber-optic Monitoring of Spinal Cord Hemodynamics in Experimental Aortic Occlusion, Anesthesiology, Dec. 2015, 123(6), pp. 1362-1373.

Lemaire, S.A., et al., Transcutaneous near-infrared Spectroscopy for Detection of Regional Spinal Ischemia during Intercostal Artery Ligation: Preliminary Experimental Results, J Thorac Cardiovasc Surg., Nov. 2006, 132(5), pp. 1150-1155.

Macnab, A.J., et al., Near Infrared Spectroscopy for Intraoperative Monitoring of the Spinal Cord, Spine (Phila Pa 1976), Jan. 1, 2002, 27(1), pp. 17-20.

Matcher, S.J., et al., Performance Comparison of Several Published Tissue Near-Infrared Spectroscopy Algorithms, Anal. Biochem., May 1995, 227(1), pp. 54-68.

Mesquita, R. C., et al., Optical Monitoring and Detection of Spinal Cord Ischemia, PLoS One, Dec. 16, 2013, 8 (12).

Moerman, A., et al., Near-infrared Spectroscopy for Monitoring Spinal Cord Ischemia during Hybrid Thoracoabdominal Aortic Aneurysm Repair, J Endovasc Ther., Feb. 2011, 18(1), pp. 91-95.

Ploumis, A et al., A Systematic Review of the Evidence Supporting a Role for Vasopressor Support in Acute SCI, Spinal Cord, 2010, 48(5), pp. 356-362.

Redlin, M., et al., Detection of Lower Torso Ischemia by near-infrared Spectroscopy during Cardiopulmonary Bypass in a 6.8-kg Infant with Complex Aortic Anatomy, Ann Thorac Surg., Jul. 2006, 82(1), pp. 323-325.

Shadgan, B., et al., Optical Assessment of Spinal Cord Tissue Oxygenation Using a Miniaturized Near Infrared Spectroscopy Sensor, Journal of Neurotrauma, 2019, 36, pp. 3034-3043.

Suzuki, S., et al., Tissue Oxygenation Monitor Using NIR Spatially Resolved Spectroscopy, Proc SPIE 3597, Optical Tomography and Spectroscopy of Tissue III, Jul. 19, 1999.

Tachtsidis, I., et al., Relationship between Brain Tissue Haemodynamics, Oxygenation and Metabolism in the Healthy Human Adult Brain during Hyperoxia and Hypercapnea, Adv. Exp. Med. Biol., 2009, 645, pp. 315-320.

Tator, C.H. et al., Review of the Secondary Injury Theory of Acute Spinal Cord Trauma with Emphasis on Vascular Mechanisms, J Neurosurg, Jul. 1991, 75(1), pp. 15-26.

Tsiakaka, O., et al., Toward the Monitoring of the Spinal Cord: A Feasibility Study, Microelectronics Journal, 2019, 88, pp. 145-153.

Wyser, D., et al., Wearable and Modular Functional near-infrared Spectroscopy Instrument with Multidistance Measurements at Four Wavelengths, Neurophotonics, 2017, 4(4), 041413.

1604
3018

3025
3027
1604
3018

WIRELESS OXYGEN SATURATION MEASUREMENT KIT

CROSS-REFERENCE TO RELATED APPLICATIONS

This application claims the benefit of U.S. patent application 63/749,480, filed Jan. 24, 2025, which is incorporated by reference along with all other references cited in this application.

BACKGROUND OF THE INVENTION

This invention relates to medical devices, and more specifically, to devices and techniques to measure oxygen saturation.

Oxygen saturation or StO2 is a relative measure of the concentration of oxygen that is dissolved or carried in a given medium, such as blood or tissue, as a proportion of the maximal concentration that can be dissolved in that medium at the given temperature. In medicine, oxygen saturation is the fraction of oxygen-saturated hemoglobin relative to total hemoglobin (unsaturated and saturated) in the blood. The human body maintains a specific balance of oxygen in the blood. Normal arterial blood oxygen saturation levels in humans are typically 97-100 percent. If the level falls below 90 percent, it is considered low and called hypoxemia. Arterial blood oxygen levels below 80 percent may compromise organ function, such as the brain and heart. Continued low oxygen levels may lead to respiratory or cardiac arrest. Oxygen saturation is an important measure of human health and well-being.

Oximeters are medical devices used to measure the oxygen saturation of tissue in humans and living things for various purposes. For example, oximeters are used for medical and diagnostic purposes in hospitals and other medical facilities (e.g., surgery, patient monitoring, or ambulance or other mobile monitoring for, e.g., hypoxia); sports and athletics purposes at a sports arena (e.g., professional athlete monitoring); personal or at-home monitoring of individuals (e.g., general health monitoring, or person training for a marathon); and veterinary purposes (e.g., animal monitoring).

Pulse oximeters and tissue oximeters are two types of oximeters that operate on different principles. A pulse oximeter uses a pulse to make measurements. A pulse oximeter typically measures the absorbance of light due to pulsing arterial blood. In contrast, a tissue oximeter does not need a pulse in order to function, and can be used to make oxygen saturation measurements of a tissue flap that has been disconnected from a blood supply or of tissue, such as internal organs that are connected to a blood supply.

Human tissue, as an example, includes a variety of light-absorbing molecules. Such chromophores include oxygenated hemoglobin, deoxygenated hemoglobin, melanin, water, lipid, and cytochrome. Oxygenated hemoglobin, deoxygenated hemoglobin, and melanin are the most dominant chromophores in tissue for much of the visible and near-infrared spectral range. Light absorption differs significantly for oxygenated and deoxygenated hemoglobins at certain wavelengths of light. Tissue oximeters can measure oxygen levels in human tissue by exploiting these light-absorption differences.

Despite the success of existing oximeters, there is a continuing desire to improve oximeters by, for example, improving form factor; improving measurement accuracy; reducing measurement time; lowering cost; reducing size, weight, or form factor; reducing power consumption; improving network or wireless connectivity, and for other reasons, and any combination of these.

In particular, assessing a patient's oxygenation state at the local level is important as it is an indicator of the state of the patient's local tissue health. Thus, oximeters are often used in clinical settings, such as during surgery and recovery, where it may be suspected that the patient's tissue oxygenation state is unstable. For example, during surgery, oximeters should be able to quickly deliver accurate oxygen saturation measurements under a variety of nonideal conditions. While existing oximeters have been sufficient for postoperative tissue monitoring where absolute accuracy is not critical and trending data alone is sufficient, accuracy is, however, important during a surgery in which spot-checking can be used to determine whether tissue might remain viable or needs to be removed.

Therefore, there is a need for improved tissue oximeter sensors, oximeter devices, and oximetry methods for using and making measurements using these sensors and devices.

BRIEF SUMMARY OF THE INVENTION

An oximeter device includes a sensor probe unit that is connected by a wire to a sensor probe electronic module. The sensor probe electronic module connects wirelessly to a medical device console, which can be a phone, tablet, or other mobile device. And the medical device console can connect to a network or the Internet (e.g., the Cloud). Alternatively, the sensor probe electronic module can directly connect to the network or the Internet without a medical device console. The medical device console can execute an application and show on its display oxygen saturation and related measurements obtained through the sensor probe unit.

ViOptix, Inc. is a pioneer and worldwide leader in the field of tissue oximetry and tissue oximeters. ViOptix's products include T.Ox, T.Ox Remote, and Intra. Ox, which are described at ViOptix's Web site, www.vioptix.com. The ViOptix website, user's manuals, and other publicly available documents on its products, as of the filing date of this patent application, are incorporated by reference.

In an implementation, a form factor of the sensor probe unit is the same or similar to the form factor of the T.Ox small patch sensor having a rectangular shape with right-angle or rounded corners where the longest dimension of the width and the length of the sensor is no more than one centimeter, 2 centimeters, 3 centimeters, 4 centimeters, or 5 centimeters. In some of these embodiments, the size of the sensor is about 5 millimeters×5 millimeters with manufacturing tolerances. The operation and capabilities of the oximeter device of this application are similar to T.Ox, but without the need for a T.Ox console. Any mobile device (e.g., running Apple's iOS or Google's Android operating system) can run an application and interface with the sensor probe electronic module via Bluetooth or other wireless technology (such as an application or interface provided via a USB or Wi-Fi dongle). The application on the mobile device will display the oxygen saturation readings or a real-time oxygen saturation graph that are updated periodically, such as every 4 seconds. In the application, a user can set custom alarms or alerts that occur when the measured oxygen saturation exceeds or falls below a certain level.

Other objects, features, and advantages of the present invention will become apparent upon consideration of the following detailed description and the accompanying drawings, in which like reference designations represent like features throughout the figures.

DETAILED DESCRIPTION OF THE INVENTION

Figure 1:
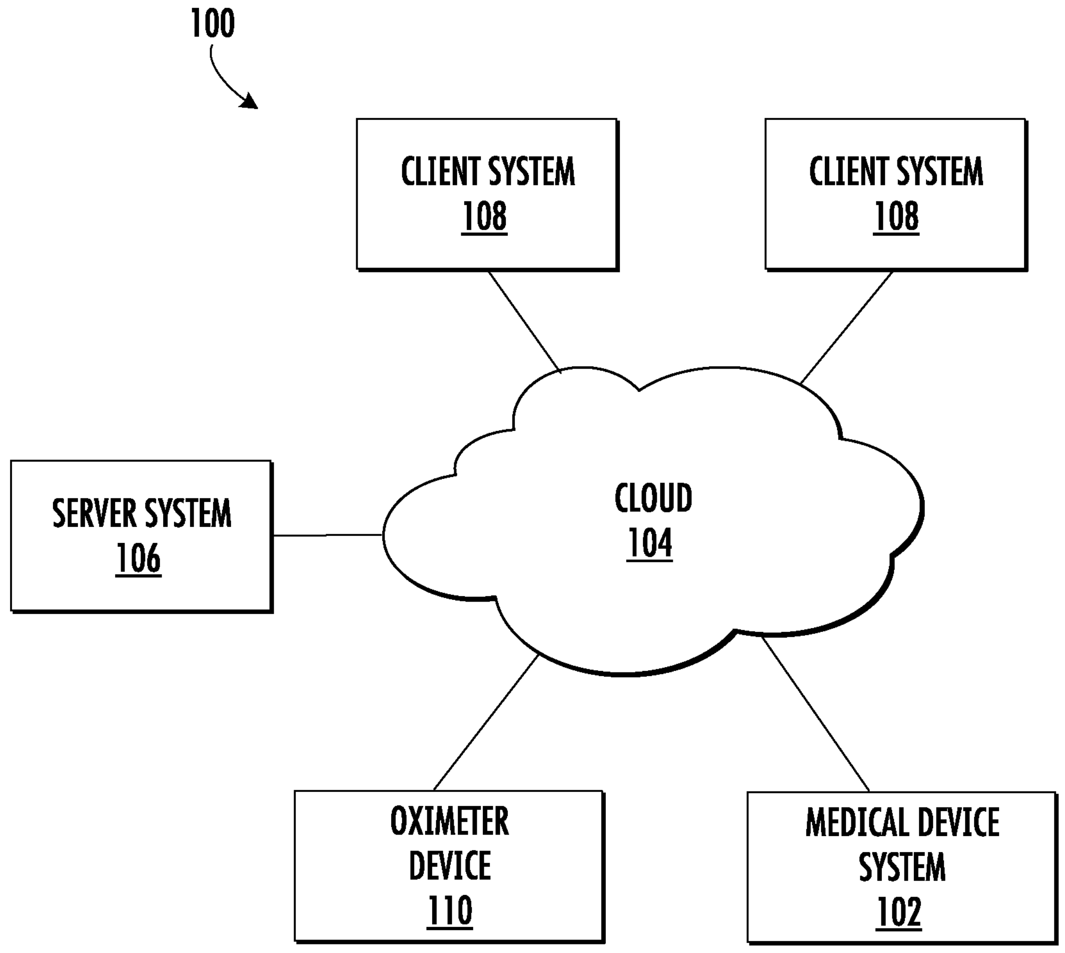
FIG. 1 is an architectural diagram of a computing environment to which various techniques described in this application may be applied, in an implementation.

Some embodiments of the present invention relate to the field of medical devices, their use and manufacture. Some embodiments relate generally to optical imaging systems that monitor oxygen levels in tissue. These embodiments relate to monitoring oxygen levels to determine the viability of flaps before and after a flap transplant. Some embodiments relate to medical devices and techniques for diagnosing intestinal ischemia or bowel ischemia.

Flap surgery is a type of plastic or reconstructive procedure that enables tissue from one area of a body to effectively be moved to another area of the body. A flap is a section of living tissue with a blood supply that may be transported from a "donor" area of a body to a new area of the body, i.e., an area onto which the flap is to be transplanted. A flap may be transplanted to an area of the body that has lost, for example, skin, fat, or muscle. Flap surgery generally restores some skin, fat, muscle movement, or skeletal support (e.g., in areas of the patient's body that have lost bone(s)) to an area in which muscle movement, fat, bone(s), or skin coverage may have been missing or lost.

There are many different kinds of flaps that are used in flap surgery. A local flap is typically a piece of skin with underlying tissue that is located next to a wound. The local flap is repositioned over the wound while remaining attached at one end, such that the local flap may be nourished by its original blood supply. A regional flap is generally a section of tissue that is attached by a specific blood vessel or specific blood vessels. When lifted, the regional flap uses a relatively narrow attachment to the donor, or original, site to receive a blood supply from the specific blood vessel or vessels, e.g., a tethered artery and vein. A musculocutaneous flap, i.e., a muscle and skin flap, is typically used when an area to be covered by the flap is relatively large and requires a significant blood supply. A musculocutaneous flap is often used in breast reconstruction surgery and remains tethered to its original blood supply. A microvascular free flap is a flap of tissue and skin that is detached, along with blood vessels, from an original site of a body and reattached to a new site in the body. As a microvascular free flap is completely detached from an original site, the attachment of such a flap to a new site requires reattaching severed blood vessels at the new site.

Blood flow through transplanted flaps may change drastically in the period of time substantially immediately after a transplant is completed. A transplanted flap may sometimes die, i.e., transplanted tissue may die, when the blood flow through the transplanted flap is compromised. For example, a blood clot in the transplanted flap or a pinched vein in the transplanted flap may cause the transplanted flap to die. Currently, to monitor a transplanted flap to determine whether blood flow through a transplanted flap is adequate to sustain the transplanted flap, laser Doppler flap monitoring may be used. Laser Doppler flap monitoring, or laser Doppler flowmetry, allows Doppler measurements to be made near blood vessels of the transplanted flap. Interpretation of the Doppler measurements may enable potential flap failures to be detected before clinical signs of failure, e.g., discoloration of the transplanted flaps, manifest themselves.

Though laser Doppler flap monitoring may be effective for enabling potential flap failures to be detected in some instances, laser Doppler systems are generally able to make measurements on relatively large vessels and are unable to measure regional perfusion in the micro-vasculature within a skin flap. Even though flow may be detected in larger vessels when laser Doppler flap monitoring is employed, distal flap tissue may be under-perfused and, as a result, may die.

As an alternative to laser Doppler flap monitoring, some surgeons may nick a transplanted flap in various places to assess the blood flow therethrough. Nicking a transplanted flap is invasive and does not always allow for an accurate determination of the viability of a transplanted flap, as assessing the blood flow in such a manner is highly subjective. Further, it may be very difficult to determine where in a transplanted flap to make a nick, e.g., a surgeon may inadvertently fail to make a nick near a blood vessel that is pinched.

Therefore, what is needed is a method and an apparatus that allows the viability of a transplanted flap to be accurately determined. That is, what is desired in some embodiments is a system that is non-invasive and relatively non-subjective, and allows the blood flow through a flap to be accurately assessed.

Intestinal ischemia or bowel ischemia is a term used to describe the result of a variety of disorders that cause insufficient blood flow to the gastrointestinal tract. Ischemia can be localized to a relatively small part of the small intestine or large intestine, or it may be widespread and involve both types of intestines. Moreover, ischemic necrosis (i.e., localized death of living cells) of the intestine can be superficial, involving the mucosa (inner lining) to full thickness transmural necrosis. Intestinal ischemia can manifest with symptoms ranging from mild, short-lived abdominal pain to bloody diarrhea or a more serious situation that may require surgery.

There are several causes for intestinal ischemia. The most common cause is diminished intestinal perfusion resulting from low cardiac output. It is often seen in patients with cardiac disease or in patients with prolonged shock of any etiology. Another cause of intestinal ischemia is an occlusive disease of the vascular supply to the intestine. The occlusive disease can result from atheroma (i.e., a deposit of lipid-containing plaques on the inner wall layer of an artery), thrombosis (i.e., a stationary clot attached to the blood vessel wall), or embolism (i.e., a migrating blood clot that forms a blockage) in which the collateral circulation is not adequate to maintain intestinal integrity. Another common form of intestinal ischemia is ischemic colitis, in which inflammation and injury of the colon result from inadequate blood supply.

When ischemic bowel disease severely damages tissue in the intestine, the damaged tissue must be surgically removed. The remaining tissue can be sewn together, typically in end-to-end anastomosis (i.e., surgical connection of two severed tubular organ parts). Prior to resection, a surgeon must distinguish between viable and nonviable intestinal tissue. Typically, the surgeon relies on subjective visual inspection, such as tissue color, to determine which intestinal tissue is viable. Such a decision is often made hastily during an operation. Further, such visual inspection has been shown to be unreliable in determining the long-term viability of intestinal tissue.

Determining intestinal viability is difficult but important for patients with ischemic bowel disease. If nonviable tissue is not removed, the result can be fatal. Removing too much intestine can also lead to severe complications. Thus, there is a need for better medical devices and systems that can determine the oxygenation state of the entire thickness of an intestinal tissue, as well as other tissues. Improved devices and systems can better assist doctors in determining the viability of an intestinal tissue, and the doctors can make a better-informed decision regarding a treatment plan for the patient. Some embodiments of the present invention meet this and other needs.

Moreover, some embodiments of the present invention relate to methods of diagnosing peripheral vascular disease (PVD) using measured changes in oxygen saturation in tissue. More specifically, the invention relates to diagnosing peripheral vascular disease from an analysis of oxygen saturation during recovery from, for example, ischemia (reduced or stoppage of blood flow), PVD (peripheral vascular disease), exercises for enhancing metabolic demands, and others.

Peripheral vascular disease is a condition that is exemplified by a narrowing of blood vessels to internal organs and muscles. Patients with peripheral vascular disease are four times more likely to have a myocardial infarction and three times more likely to have a stroke. The five-year mortality rate for people with peripheral vascular disease is 30 percent. Peripheral vascular disease affects 20 percent of the elderly and 40 percent of diabetics.

Unfortunately, it has been estimated that 8-12 million people in the United States are affected with this disease and the numbers are growing at a rate of five percent a year. Although these numbers show that peripheral vascular disease is a fairly common disease, peripheral vascular disease is often not diagnosed or is misdiagnosed. It has been estimated that 71 percent of physicians overlook a peripheral vascular disease condition in their patients.

As provided for in some embodiments of the present invention, it would be beneficial to have innovative techniques for diagnosing peripheral vascular disease. Additionally, it would be beneficial to have techniques for diagnosing peripheral vascular disease with relatively high accuracy rates.

Some embodiments of the present invention relate generally to optical imaging systems that monitor oxygen levels in tissue. More specifically, the present invention relates to optical probes that include sources and detectors that are symmetrically arranged on sensor heads of the optical probes.

Near-infrared spectroscopy has been used for noninvasive measurement of various physiological properties in animal and human subjects. The basic principle underlying near-infrared spectroscopy is that physiological tissues include various highly-scattering chromophores to the electromagnetic waves (e.g., near-infrared waves) with relatively low absorption. Many substances in a medium may interact or interfere with the light waves (e.g., electromagnetic waves such as visible or near-infrared waves) propagating therethrough. Human tissues, for example, include numerous chromophores such as oxygenated hemoglobin (a form of hemoglobin that carries oxygen from the lungs to body tissues), deoxygenated hemoglobin (a form of hemoglobin that has released its oxygen to tissues and is no longer bound to oxygen), water, lipid, and cytochrome, where the hemoglobin are the dominant chromophores in the spectrum range of approximately 700 nanometers to approximately 900 nanometers. Accordingly, the near-infrared spectroscope has been applied to measure oxygen levels in the physiological medium, such as tissue hemoglobin oxygen saturation and total hemoglobin concentrations.

Various techniques have been developed for the near-infrared spectroscopy, e.g., time-resolved spectroscopy (TRS), phase modulation spectroscopy (PMS), spatial frequency domain imaging (SFDI), and continuous wave spectroscopy (CWS). In a homogeneous and semi-infinite model, both TRS and PMS have been used to obtain spectra of the absorption coefficients and reduced scattering coefficients of the physiological medium by solving a photon diffusion equation, and to calculate concentrations of oxygenated and deoxygenated hemoglobin as well as tissue oxygen saturation. CWS has generally been designed to solve a modified Beer-Lambert equation and to measure changes in the concentrations of oxygenated and deoxygenated hemoglobin.

Despite their capability of providing the hemoglobin concentrations as well as the oxygen saturation, one major drawback of TRS and PMS is that the equipment is bulky and expensive. CWS may be manufactured at a lower cost but is limited in its utility because it cannot compute the oxygen saturation from the changes in the concentrations of oxygenated and deoxygenated hemoglobin.

Optical diffusion imaging and spectroscopy (ODIS) allows tissue to be characterized based on measurements of photon scattering and absorption. In tissue such as human tissue, near-infrared light is highly scattered and minimally absorbed. Optical diffusion imaging is achieved by sending optical signals into tissue and measuring the corresponding diffuse reflectance or transmittance on the tissue surface.

Scattering is caused by the heterogeneous structure of a tissue and, therefore, is an indicator of the density of a cell and the nuclear size of the cell. Absorption is caused by interaction with chromophores. ODIS emits light into tissue through a sensor. The position of the light source, which emits the light, and a detector, which detects the light, allows a depth of measurement to be determined. A ratio of oxyhemoglobin and deoxyhemoglobin may be used to allow for substantially real-time measurement of oxygen, e.g., oxygen saturation levels. In some embodiments, a light source emits electromagnetic waves that include a carrier wave. In some of these embodiments, an electromagnetic wave described herein may further include a modulating signal (or message signal) where the modulating signal carries the information that is superimposed onto the carrier wave to allow the information to be transmitted via the electromagnetic waves. In some embodiments where more than one light source is employed, the emitted light from these multiple sources includes multiple different wavelengths (or frequencies) of light where each light source may emit light having a single wavelength or multiple different wavelengths (e.g., multi-spectral light source). In these embodiments, the respective carrier waves of light having different wavelengths (or frequencies) are characteristically different from one another as respectively exhibiting at least different wavelengths and different frequencies.

Within ODIS systems, sensors that come into contact with tissue surfaces generally have optical fibers arranged thereon in a substantially symmetric layout. That is, optical fibers that are coupled to light sources are arranged in a substantially symmetric orientation relative to optical fibers that are coupled to light detectors. While a symmetric orientation is effective in allowing for oxygen saturation levels to be measured, the manufacture of such a sensor is often difficult, as the exact placement of the optical fibers within the sensor is crucial. Further, when the anatomy of tissue or underlying structure is not substantially symmetric, the use of a sensor with a symmetric orientation may not allow for accurate measurements to be readily made.

Therefore, what is needed in some embodiments is a sensor that is relatively easy to manufacture and is arranged to be used on tissue that may not have a symmetric anatomy. That is, what is desired is a sensor with a layout of optical structures (which can include optical fibers) for light sources and optical structures (which can include optical fibers) for detectors that facilitate use with tissue having substantially any anatomy.

Some embodiments of the present invention relate to medical devices and their manufacture. More particularly, the present invention relates to patient monitoring devices and methods.

Patient monitoring systems measure, display, and sometimes store physiological data. Patient monitoring systems are now used in a wide variety of applications. This includes, for example, hospital, ambulatory, and home health care. Hospitals routinely measure and analyze the vital signs of surgical, trauma, and other patients from admission through discharge. There are many different types of monitoring devices. For example, there are monitoring devices for blood pressure, body temperature, heart activity, blood gases, cholesterol, glucose, pulse rate, respiration rate, tissue oxygen saturation, and many other parameters.

Noninvasive monitoring devices fulfill an important role in assessing, tracking, diagnosing, and treating patients. These devices enable early diagnosis, treatment of acute conditions, and reduce the need for invasive interventions. Some types of monitoring devices gather patient data via sensors attached to the patient.

In order for the sensors gather accurate information, it is important that they are protected from outside interference. They should also be comfortable for the patient to wear, as the sensors may be attached to the patient for long periods of time. Furthermore, in an operating room environment or for an open wound, anything that touches or comes near the patient must be sterile. Thus, sterility is also a concern. These are just a few examples of desirable features.

There is, then, a continuing demand for medical devices that are easier to use, safer to use, usable in locations outside the hospital, provide more features, and generally address the needs of patients, doctors, nurses, clinicians, first responders, and others in the medical community.

Some embodiments of the present invention fulfill the need to provide improved systems and techniques for monitoring patients.

Some embodiments of the present invention relate to methods of diagnosing peripheral vascular disease (PVD) using measured changes in oxygen saturation in tissue. More specifically, the invention relates to diagnosing peripheral vascular disease from an analysis of oxygen saturation during recovery from ischemia (reduced or stoppage of blood flow).

These embodiments thus provide innovative techniques for diagnosing peripheral vascular disease as well as techniques for diagnosing peripheral vascular disease with relatively high accuracy rates.

Some embodiments of the present invention relate to methods and apparatuses for diagnosing peripheral vascular disease (PVD) using measured changes in oxygen saturation in tissue. More specifically, these embodiments relate to diagnosing peripheral vascular disease from an analysis of oxygen saturation during recovery from ischemia (reduced or stoppage of blood flow).

There is a need for innovative techniques for diagnosing peripheral vascular disease in these embodiments. Additionally, or alternatively, there is a need for techniques of diagnosing peripheral vascular disease with relatively high accuracy rates.

Some embodiments relate generally to optical imaging systems that monitor oxygen levels in tissue. More specifically, the present invention relates to monitoring oxygen levels to determine the viability of flaps before and after a flap transplant.

Some embodiments of the present invention relate to medical devices and their manufacture. More particularly, the present invention relates to patient monitoring devices and methods.

Patient monitoring systems measure, display, and sometimes store physiological data. Patient monitoring systems are now used in a wide variety of applications. This includes, for example, hospital, ambulatory, and home health care. Hospitals routinely measure and analyze the vital signs of surgical, trauma, and other patients from admission through discharge. There are many different types of monitoring devices. For example, there are monitoring devices for blood pressure, body temperature, heart activity, blood gases, cholesterol, glucose, pulse rate, respiration rate, tissue oxygen saturation, and many other parameters.

Noninvasive monitoring devices fulfill an important role in assessing, tracking, diagnosing, and treating patients. These devices enable early diagnosis, treatment of acute conditions, and reduce the need for invasive interventions. Some types of monitoring devices gather patient data via sensors attached to the patient.

In order for the sensors gather accurate information, it is important that they are protected from outside interference. They should also be comfortable for the patient to wear, as the sensors may be attached to the patient for long periods of time. Furthermore, anything that touches or comes near the patient must be sterile. Thus, sterility is also a concern. These are just a few examples of desirable features.

There is, then, a continuing demand for medical devices that are easier to use, safer to use, usable in locations outside the hospital, provide more features, and generally address the needs of patients, doctors, nurses, clinicians, first responders, and others in the medical community. Therefore, there is a need for an improved system and techniques for monitoring patients.

Some embodiments of the present invention relate to the field of medical devices, their use and manufacture, and more specifically to medical devices and techniques for diagnosing intestinal ischemia or bowel ischemia.

When the blood supply to a tissue or organ within a body is diminished due to poor circulation or blockage of blood vessels, the tissue or organ suffers ischemia, which results in diminished functioning of the tissue or organ. The tissue or organ ischemia can present various symptoms in a patient, which makes a proper diagnosis of the underlying disease difficult for a doctor. Consequently, an ischemic disease is often not diagnosed until an advanced stage, which limits treatment options for the patient.

This is particularly the case for a patient suffering with intestinal ischemia. The ischemic condition or oxygenation state of an internal organ, such as the intestine or mesentery, is difficult to evaluate. The intestine is a long tubular organ that can stretch about 7 feet long. The mesentery is a fold of tissue that anchors the intestine to the back of the abdominal wall. Blood vessels, nerves, and lymphatics branch through the mesentery to supply the intestine. Since the intestine and mesentery involve an extensive network of tissues, it is difficult to localize an ischemic area in the tissue.

The present invention provides various medical devices and systems for measuring the oxygen saturation of a tissue located inside a body. In particular, the devices and systems can be used to measure oxygen saturation of the mouth, esophagus, stomach, small intestine, large intestine, mesentery, anus, or others. While some of these body parts may be classified as organs, for this application, “tissue” and “organ” are used interchangeably to refer to any body part or aggregate of cells. In other words, "tissue" may be used to refer to an organ, and vice versa.

The medical devices and systems in accordance with embodiments of the invention include a catheter device, an endoscopic device, and a needle sensor device, which allow the doctor to explore tissues deep inside a body noninvasively or with a minimal pin-sized puncture. In embodiments of the invention, the devices include a sensor probe that has one or more optical fibers that form an oximeter at a distal end of the sensor probe. As the devices are guided down along the gastrointestinal tract, the oximeter sensor of the sensor probe can contact a tissue and measure oxygen saturation at various locations along the tract.

In embodiments of the invention, the sensor probe is connected to a signal emitter which sends light having a wavelength from about 600 nanometers to about 1000 nanometers through optical fibers in the sensor probe into a tissue in some embodiments. In some embodiments, the wavelength may fall within the range of 700 to 900 nanometers. After being scattering and absorbed by chromophores (e.g., hemoglobin) in the tissue, an attenuated version of the light is detected by the sensor probe and is transmitted to a photodetector.

In an implementation, the sensor probe uses a ratiometric algorithm, and does not use a calibration or have any knowledge of an unattenuated brightness. In another implementation, based on values of the initial light and the attenuated version of the light, an oxygen saturation value of the tissue can be obtained. Based on the oxygen saturation value of the tissue, it can be determined whether the tissue is suffering from ischemia.

Embodiments of the invention can be used in a wide variety of applications. One application is in diagnosing whether or not a patient has intestinal ischemia or exhibits a hypoxic condition. Moreover, the devices and systems can be used to determine the severity of intestinal ischemia and the extent of tissue damage. In another application, the devices and systems can be used in monitoring oxygen saturation of an intestinal tissue or mesentery during a surgical procedure (e.g., anastomosis). Since oxygen saturation measurements can be made in real-time during surgery, any necessary modifications to surgical procedures can be made based on oxygen saturation measurements. Furthermore, the devices and systems can also be used during recovery after surgery to evaluate a patient's prognosis.

Embodiments of the present invention provide several advantages. The catheter and endoscopic devices can be inserted into a human body noninvasively to determine the oxygenation state of a mucosal surface of the intestine or any other tissue along the gastrointestinal tract. Moreover, the sensor needle device can be introduced into an abdomen through a pin-sized hole to determine the oxygenation state of a serosal surface of the intestine or mesentery. These devices cause minimal discomfort to the patient and rarely cause any medical complications.

Moreover, the devices and systems according to embodiments of the invention provide oxygen saturation measurements of the entire thickness of the intestine, not just the outer skin or superficial surface of the intestine. An oximeter sensor of the present devices and systems also directly contacts a tissue to make oxygen saturation measurements of the tissue. Thus, the oxygen saturation measurements according to embodiments of the invention can assess the oxygenation state of the intestine more accurately.

Further, sensor probes, catheter devices, and sensor needle devices of the present invention are cost-effective to manufacture. The cost-effectiveness is important as the devices containing a sensor probe are typically disposed of after a single use. Also, since the portion of a device that is placed onto tissue or introduced into a body cavity is sealed (e.g., electrically sealed and liquid or fluid sealed) so that any electrical components such as light emitting diodes, photodiodes, or exposed electrical connections, cannot come in contact with tissue or internal organs, which may otherwise be subject to electrical shock, heating, or burning by the device.

Moreover, assessing the blood supply associated with a flap is crucial to ensure that the flap is viable. By monitoring the oxygen saturation level of an area on flap tissue, the blood flow to at least that area may be determined. Monitoring an oxygen saturation level is generally a non-invasive, non-subject process. Near-infrared spectroscopy has been used for non-invasive measurement of various physiological properties in animal and human subjects. The basic principle underlying near-infrared spectroscopy is that physiological tissues include various highly-scattering chromophores to the near-infrared waves with relatively low absorption. Many substances in a medium may interact or interfere with the near-infrared light waves propagating therethrough. Human tissues, for example, include numerous chromophores such as oxygenated hemoglobin, deoxygenated hemoglobin, water, lipid, and cytochrome, where the hemoglobins are the dominant chromophores in the spectrum range of approximately 700 nm to approximately 900 nm. Accordingly, the near-infrared spectroscope has been applied to measure oxygen levels in the physiological medium, such as tissue hemoglobin oxygen saturation and total hemoglobin concentrations.

Optical Diffusion Imaging and Spectroscopy (ODIS) allows tissue to be characterized based on measurements of photon scattering and absorption. In tissue such as human tissue, near infrared light is highly scattered and minimally absorbed. Optical diffusion imaging is achieved by sending optical signals into tissue and measuring the corresponding diffuse reflectance or transmittance on the tissue surface.

Scattering is caused by the heterogeneous structure of a tissue and, therefore, is an indicator of the density of a cell and the nuclear size of the cell. Absorption is caused by interaction with chromophores. ODIS emits light into tissue through a sensor. The position of the light source, which emits the light, and a detector, which detects the light, allows a depth of measurement to be determined. A ratio of oxyhemoglobin and deoxyhemoglobin may be used to allow for substantially real-time measurement of oxygen, e.g., oxygen saturation levels. A percentage of hemoglobin that is bound to oxygen may express an oxygen saturation level.

In one embodiment, measuring oxygen saturation levels associated with a flap may enable a surgeon to accurately identify areas of a flap that may not be viable. Being able to identify areas that are not viable enables corrective actions to be taken substantially before the integrity of the overall flap is compromised. By way of example, a surgeon may be able to trim tissue from areas of a flap that may not be viable in an effort to preserve the integrity of the remainder of the flap. In addition, if oxygen saturation levels are measured in a potential flap before the potential flap is removed for transplant, arteries that provide significant blood flow to the potential flap may be identified and, hence, designated for use as reattachment arteries.

Some embodiments are directed to a sensor head where optical fibers that are coupled to light sources are arranged in an offset orientation relative to optical fibers that are coupled to detectors allows the sensor head to be utilized in areas in which tissue being monitored is not substantially symmetric. Any attenuation associated with the offset orientation of optical fibers that are coupled to light sources is typically compensated for through software. Such a sensor head is relatively easy to manufacture in that the placement of optical fibers that are coupled to light sources is less rigid, i.e., any slight variation in the placement of the optical fibers may be corrected for using the software that compensates for attenuation. In addition, the use of software to compensate for attenuation associated with the placement of optical fibers on a sensor head essentially enables the sensor head to be used with both symmetric and asymmetric tissue anatomies.

As will be understood by those skilled in the art, a volume of tissue substantially immediately beneath a sensor head may either be homogeneous or inhomogeneous, depending upon the actual anatomical structures contained within this volume. By way of example, when a sensor head is positioned on skin overlying a thick region of adipose tissue, the distribution of, for example, epithelial cells, capillaries, and tissues containing red blood cells that contain oxygenated hemoglobin is generally relatively uniform, i.e., symmetric and homogenous. However, a sensor head may be positioned over a tissue volume in which the underlying structure includes arteries, veins, bone, tendon, cartilage, fascia, muscle, or pigmented lesions. Such tissue may have asymmetric anatomies that cause light to be reflected, refracted, or absorbed asymmetrically due, for example, to regions that are either unusually reflective or absorptive. It is noted that refraction does occur when shining light on a physiological medium, oximetry primarily relies on reflection of light where differential light absorption by oxygenated and deoxygenated hemoglobin at specific wavelengths for measuring how much light is absorbed by the blood at different light colors to determine, for example, oxygen saturation levels.

Software can compensate for attenuation may eliminate readings associated with light that reflects off of structures such as bone. Optical structures that are coupled to sources and are positioned in a sensor head in an offset orientation relative to optical structures optically coupled to detectors may facilitate the transmission and reading of light that avoids structures such as bone. Hence, the use of offset source optical structure orientations facilitates the creation of specialized sensor heads that may be used to measure oxygen saturation in many different parts of a body. In some embodiments, reflection occurs when light bounces off a surface (e.g., a surface on the exterior or interior of a physiological medium such as human tissues), while refraction occurs when light bends as the light passes through a medium (e.g., a physiological medium). Either reflection or refraction or both reflection and refraction when shining a light onto a physiological medium. For example, a portion of the light may penetrate into the physiological medium and changes direction or propagation (refraction); a smaller portion of the penetrated light may be absorbed; and some or all of the remainder of the penetrated light may be reflected off one or more surfaces within the physiological medium and eventually leave the physiological medium and detected by, for example, a detector described herein.

Some embodiments are directed to assessing the blood supply associated with a flap is crucial to ensure that the flap is viable. By monitoring the oxygen saturation level of an area on flap tissue, the blood flow to at least that area may be determined. Monitoring an oxygen saturation level is generally a non-invasive, non-subject process. Near-infrared spectroscopy has been used for non-invasive measurement of various physiological properties in animal and human subjects. The basic principle underlying the near-infrared spectroscopy is that physiological tissues include various highly-scattering chromophores to the near-infrared waves with relatively low absorption. Many substances in a medium may interact or interfere with the near-infrared light waves propagating therethrough. Human tissues, for example, include numerous chromophores such as oxygenated hemoglobin, deoxygenated hemoglobin, water, lipid, and cytochrome, where the hemoglobins are the dominant chromophores in the spectrum range of approximately 700 nm to approximately 900 nm. Accordingly, the near-infrared spectroscope has been applied to measure oxygen levels (e.g., tissue hemoglobin oxygen saturation and total hemoglobin concentrations) in a physiological medium.

Optical Diffusion Imaging and Spectroscopy (ODIS) allows tissue to be characterized based on measurements of photon scattering and absorption. In tissue such as human tissue, near infrared light is highly scattered and minimally absorbed. Optical diffusion imaging is achieved by sending optical signals into tissue and measuring the corresponding diffuse reflectance or transmittance on the tissue surface.

Scattering is caused by the heterogeneous structure of a tissue and, therefore, is an indicator of the density of a cell and the nuclear size of the cell. Absorption is caused by interaction with chromophores. ODIS emits light into tissue through a sensor. The position of the light source, which emits the light, and a detector, which detects the light, allows a depth of measurement to be determined. A ratio of oxyhemoglobin and deoxyhemoglobin may be used to allow for substantially real-time measurement of oxygen, e.g., oxygen saturation levels. A percentage of hemoglobin that is bound to oxygen may express an oxygen saturation level.

In the description that follows, the present invention will be described in reference to embodiments. However, embodiments of the invention are not limited to any particular environment, application, or implementation. For example, although different techniques of monitoring changes in oxygen saturation will be described, the invention is not limited to the specific embodiments described below. Therefore, the description of the embodiments that follows is for purposes of illustration and not limitation. Further, any embodiment or even a feature thereof described herein can be readily combined with any other embodiment or embodiments or feature thereof described herein or equivalents thereof, unless otherwise explicitly disclaimed or described as mutually exclusive of one another. Moreover, examples of embodiments of the invention are shown using figures and are described below. The figures described herein are used to illustrate embodiments of the invention, and are not in any way intended to be restrictive of the broad invention. Embodiments of the invention are not limited to the specific arrangements and constructions shown and described. For example, features shown in one figure can be combined with features shown in another figure.

FIG. 1 is an architectural diagram of a computing environment to which various techniques described in this application may be applied, in an implementation. More specifically, FIG. 1 shows a computing environment 100 where a plurality of client systems 108 that may be connected with a server system 106, one or more medical device systems 102 or oximeter devices 110 via a cloud computing environment or a network 104 to provide various oximetry features, oximetry functions, oximetry tasks, and other functions. Client systems 108 can include one or more types of computing devices, such as a mobile device (e.g., portable phone or tablet computer), a laptop, a desktop, a server, and other devices.

Medical device system 102 can be a medical device system or a patient monitoring system for monitoring oxygen saturation of patient tissue to further determine the viability of the patient tissue. Medical device system 102 can monitor patient tissue to determine the oxygen saturation of the patient tissue to further determine the viability of the patient tissue. The oximetry information can be displayed on the medical device system. The medical device system can send the oximetry information to the server system for storage via network 104, in an implementation. The medical device system can send the oximetry information to one or more of the client systems, such as in a peer-to-peer configuration, for storage and display on the one or more client systems via network 104, in an implementation.

Oximeter device 110 can be a medical device or a patient monitoring device for monitoring oxygen saturation of patient tissue to further determine the viability of the patient tissue. Oximeter device 110 can monitor patient tissue to oxygen saturation of the patient tissue to further determine the viability of the patient tissue. Medical device system 102 can include an oximeter device 110, as will be described below. The oximeter device can send the oximetry information to the server system for storage via network 104, in an implementation. The oximeter device can send the oximetry information to one or more of the client systems, such as in a peer-to-peer configuration, for storage and display on the one or more client systems via network 104, in an implementation.

Client system 108 can access the server system 106 via network 104 to access oximetry information stored on the server system to display the oximetry information, in an implementation. Client system 108 can access the medical device system 102 via network 104 to access oximetry information stored on the server system to display the oximetry information, in an implementation. Client system 108 can access the oximeter device 110 via network 104 to access oximetry information stored on the server system to display the oximetry information, in an implementation. The client system and the medical device system store and operate computer applications that allow the client system and the oximeter device to transfer oximetry information to the client system for display, in an implementation.

Cloud network 104 can include one or more of a private cloud, a public cloud, a hybrid cloud, the Internet, an intranet, a mesh network, and other types of networks.

The cloud computing environment or network 104 may be provisioned for access by one or more of the server systems 106 (e.g., one or more server computers, one or more virtual machines, one or more executable containers, and others), in some implementations. The medical device system 102 may be connected to the cloud through a hard-wire connection, wirelessly, or through either a hard-wired or wireless connection. The oximeter device 110 may be connected to the cloud through a hard-wire connection, wirelessly, or through either a hard-wired or wireless connection.

The medical device system and oximeter device (sometimes referred to as a sensor probe unit below) facilitate various functionalities described, such as monitoring the viability of biological tissue, intestinal ischemia, bowel ischemia, peripheral vascular disease, and other measurements to determine one or more of oxygen saturation, percentage of oxygenated hemoglobin, percentage of deoxygenated hemoglobin, and other oximetry values for tissue oximetry measurements.

Figure 2:
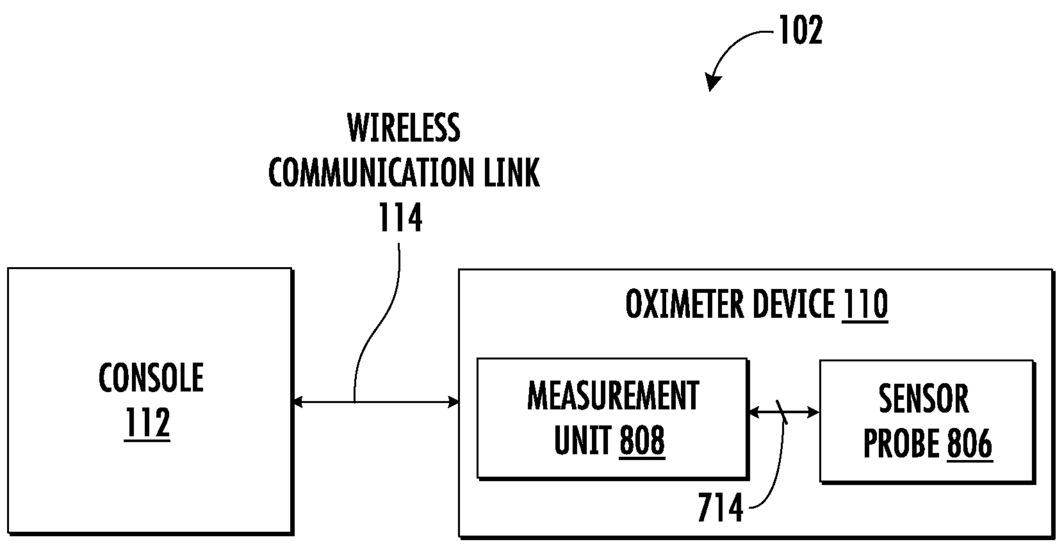
FIG. 2 shows a simplified diagram of an example medical device system in which some of the various oximetry techniques described in this application may be implemented.

FIG. 2 shows a simplified diagram of an example medical device system 102 in which some of the various oximetry techniques described in this application may be implemented, according to some implementations. Medical device system 102 includes a medical device console 112 and an oximeter device 110 that is connected to the medical device console 112 via a wired or wireless connection 114. Medical device console 112 can be a tablet computer or other type of computing device. Oximeter device 110 is sometimes referred to as a sensor probe system or a sensor probe.

Oximeter device 110 is configured to contact patient tissue for making oximetry measurements of the tissue and is sometimes referred to as an oximeter device.

The oximeter device 110 includes a sensor probe electronic module 808 connected to a sensor probe unit 806 via conductors 714. Sensor probe electronic module 808 is sometimes referred to as a measurement unit and sensor probe unit 806 is sometimes referred to as a sensor head. The conductors can include wires, such as wires in ribbon cable or discrete wires. Conductors 714 can include a number of conductors for two-way communication between the sensor probe electronic module and the sensor probe, where communication signals can travel from the sensor probe electronic module to the sensor probe and from the sensor probe to the sensor probe electronic module. Conductors 714 can also include a number of conductors that supply power to the sensor probe. Power can be supplied from the sensor probe electronic module to the sensor probe by a one-way power supply connection, where the sensor probe electronic module supplies DC power to the sensor probe.

The sensor probe is configured to contact patient tissue to make oximetry measurements of the tissue. More specifically, the sensor probe is configured to emit light into the tissue and collect reflected or transmitted light from the tissue for making oximetry measurements of the patient tissue. The sensor probe is configured to transmit measurement information to the measurement module across conductors 714. The measurement module can process the measurement information to generate oximetry information, such as oxygen saturation values, percentage oxygenated hemoglobin, percentage non-oxygenated hemoglobin, an absorption coefficient ua, a scattering coefficient us, such as the reduced scatting coefficient, or other values. The sensor probe electronic module can display one or more of the generated values or transmit one or more of the values to console 112 for display. In an embodiment, the oximetry information can be generated by the sensor probe electronic module or the console.

In an implementation, the medical device system can store and operate a medical device application on medical device console 112 that allows an operator to control the oximeter device 110 via the application operating on the console to make oximetry measurements of patient tissue using oximeter device 110. Control signals for the medical device application can be transmitted to the sensor probe electronic module across communication link 114. The application operating on the console can also control the display of oximetry information on the display of the console where the oximetry information is generated by oximeter device 110. Medical device console 112 and oximeter device 110 are described further below.

In an implementation where communication link 114 is a wireless communication link, the communication link may operate according to one or more standard protocols such as Bluetooth or other local wireless network (IoT protocols such as Zigbee wireless mesh network, Z-wave, Bluetooth Low Energy (BLE or Bluetooth LE) aka Bluetooth 4.1. Connection 114 may operate according to other IoT protocols, such as Advanced Message Queuing Protocol, AMQP, Cellular-2G, 3G, 4G/LTE, 5G, or others, Constrained Application Protocol or CoAP, Data Distribution Service or DDS, LoRa, LoRaWAN, Lightweight M2M (LWM2M) as a device management protocol designed for sensor networks and the demands of an M2M environment, Message Queuing Telemetry Transport or MQTT, Wi-Fi, XMPP Extensible Messaging and Presence Protocol for real-time human-to-human communication, Zigbee which has a longer range than BLE but a lower data rate than BLE, Z-Wave allowing smart devices to communicate with encryption and thereby providing a level of security to the IoT (Internet of Things) deployment, and others Bluetooth LE, colloquially BLE, formerly marketed as Bluetooth Smart) is a wireless personal area network technology.

Bluetooth mesh profiles use Bluetooth Low Energy to communicate with other Bluetooth Low Energy devices in the network. Each device may pass the information forward to other Bluetooth Low Energy devices creating a mesh effect.

In some implementations, connection 114 may be established via protocols such as 802.11x, 802.15 (e.g., 802.15.1 for WPAN/Bluetooth connections, 802.15.2 for coexistence connections, 802.15.3 for high-rate WPAN, 802.15.3b-2005, 802.15.3c-2009, 802.15.3d-2017, 802.15.3e-2017, 802.15.3f-2017, 802.15.4 for low-rate WPAN connections, 802.15.4a, 802.15.5, 802.15.6, 802.15.7 for Visible Light Communication, 802.15.8 for Peer Aware Communications, 802.15.9 for Key Management Protocol, 802.15.10 for Layer 2 Routing, 802.15.13 for Multi-Gigabit/s Optical Wireless Communications, and others), DASH7 Alliance Protocol, or Ultra-wideband (UWB) or ultraband.

802.15.1 may be used for WPAN or Bluetooth connections. More particularly, task group one may be based on Bluetooth technology. 802.15.1 defines physical layer (PHY) and Media Access Control (MAC) specification for wireless connectivity with fixed, portable and moving devices within or entering personal operating space. 802.15.2 is used where task group two addresses the coexistence of wireless personal area networks (WPAN) with other wireless devices operating in unlicensed frequency bands such as wireless local area networks (WLAN).

802.15.3 for high-rate WPAN comprises a MAC and PHY standard for high-rate (11 to 55 Mbit/s) WPANs. 802.15.3a was an attempt to provide a higher speed ultra-wideband PHY enhancement amendment to IEEE 802.15.3 for applications that involve imaging and multimedia. 802.15.3b-2005 amendment was released on May 5, 2006. It enhanced 802.15.3 to improve implementation and interoperability of the MAC. This amendment includes many optimizations, corrected errors, clarified ambiguities, and added editorial clarifications while preserving backward compatibility.

802.15.3c-2009 constitutes a millimeter-wave-based alternative physical layer (PHY) for the existing 802.15.3 Wireless Personal Area Network (WPAN) Standard 802.15.3-2003. 802.15.3d-2017: an alternative physical layer (PHY) at the lower THz frequency range between 252 GHz and 325 GHz for switched point-to-point links is defined in this amendment. Two PHY modes are defined that enable data rates of up to 100 gigabytes per second using eight different bandwidths between 2.16 GHz and 69.12 GHz. 802.15.3e-2017 constitutes an alternative physical layer (PHY) and a modified medium access control (MAC) layer is defined in this amendment. Two PHY modes have been defined that enable data rates up to 100 Gb/s using the 60 GHz band. MIMO and aggregation methods have been defined to increase the maximum achievable communication speeds. Stack acknowledgment has been defined to improve the medium access control (MAC) efficiency when used in a point-to-point (P2P) topology between two devices.

802.15.3f-2017 extends the RF channelization of the millimeter wave PHYs to allow for use of the spectrum up to 71 GHz. 802.15.3f was initiated because several regulatory domains extended the licensed exempt 60 GHz bands up to 71 GHz. 802.15.4 for Low Rate WPAN connections deals with low data rate but very long battery life (months or even years) and very low complexity. The standard defines both the physical (Layer 1) and data-link (Layer 2) layers of the OSI model. IEEE 802.15.4a (formally called IEEE 802.15.4a-2007) is an amendment to IEEE 802.15.4 specifying additional physical layers (PHYs) to the original standard. The principal interest was in providing higher precision ranging and localization capability (1 meter accuracy and better), higher aggregate throughput, adding scalability to data rates, longer range, and lower power consumption and cost.

802.15.5 provides the architectural framework enabling WPAN devices to promote interoperable, stable, and scalable wireless mesh networking. This standard is composed of two parts: low-rate WPAN mesh and high-rate WPAN mesh networks. The low-rate mesh is built on IEEE 802.15.4-2006 MAC, while the high-rate mesh utilizes IEEE 802.15.3/3b MAC. The common features of both meshes include network initialization, addressing, and multi-hop unicasting. In addition, the low-rate mesh supports multicasting, reliable broadcasting, portability support, trace route and energy saving function, and the high-rate mesh supports multi-hop time-guaranteed service. IEEE 802.15.6 task group approved a draft of a standard for Body Area Network (BAN) technologies. The draft was approved on 22 Jul. 2011 by Letter Ballot to start the Sponsor Ballot process. Task Group 6 was formed in November 2007 to focus on a low-power and short-range wireless standard to be optimized for devices and operation on, in, or around the human body (but not limited to humans) to serve a variety of applications including medical, consumer electronics, and personal entertainment.

802.15.7 may be used for visible light communication with several new PHY layers and MAC routines to support optical camera communications (OCC) and light fidelity (Li-Fi). In March 2017, the 802.15 Working Group decided to continue 802.15.7 with OCC only, which is broadcast only, and to create a new task group 802.15.13 to work on a new standard for Li-Fi, which obviously needed a significantly revised MAC layer, besides new PHYs.

DASH7 Alliance Protocol (D7A) is an open-source wireless sensor and actuator network protocol, which operates in the 433 MHz, 868 MHz and 915 MHz unlicensed ISM band/SRD band. DASH7 provides multi-year battery life, range of up to 2 km, low latency for connecting with moving things, a very small open-source protocol stack, AES 128-bit shared-key encryption support, and data transfer of up to 167 kbit/s. The DASH7 Alliance Protocol is the name of the technology promoted by the non-profit consortium called the DASH7 Alliance. Ultra-wideband (UWB, ultra-wideband, ultra-wide band and ultraband) is a radio technology that can use a very low energy level for short-range, high-bandwidth communications over a large portion of the radio spectrum. UWB was proposed for use in personal area networks, and appeared in the IEEE 802.15.3a draft PAN standard.

Figure 3:
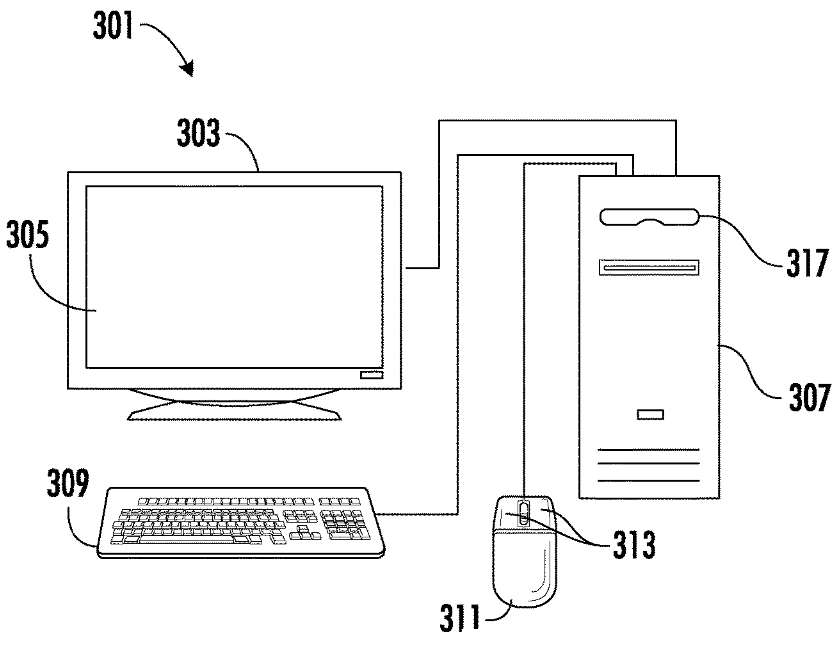
FIG. 3 shows an exemplary server system, in an implementation.

FIG. 3 shows an exemplary server system 106, client system 108, or a medical device console 112, in various implementations. In an implementation, a user interfaces with the system through a computer workstation system, such as shown in FIG. 3. FIG. 3 shows a computer system 301 that includes a monitor 303, screen 305, enclosure 307 (may also be referred to as a system unit, cabinet, or case), keyboard or another human input device 309, and mouse or another pointing device 311. Mouse 311 may have one or more buttons such as mouse buttons 313.

It should be understood that the present invention is not limited to any computing device in a specific form factor (e.g., desktop computer form factor), but can include all types of computing devices in various form factors. A user can interface with any computing device, including smartphones, personal computers, laptops, electronic tablet devices, global positioning system (GPS) receivers, portable media players, personal digital assistants (PDAs), other network access devices, and other processing devices capable of receiving or transmitting data.

For example, in a specific implementation, the client device, medical device console, one of these, or both of these can be a smartphone or tablet device, such as the Apple iPhone (e.g., Apple iphone 16), Apple iPad (e.g., Apple iPad, Apple ipad Air, Apple iPad Pro, or Apple iPad mini), Apple iPod (e.g., Apple ipod Touch), Samsung Galaxy product (e.g., Galaxy S series product or Galaxy Note series product), Google Nexus and Pixel devices (e.g., Google Pixel 7, Google Pixel 8, or Google Pixel 9), and Microsoft devices (e.g., Microsoft Surface tablet). Typically, a smartphone includes a telephony portion (and associated radios) and a computer portion, which are accessible via a touch screen display.

There is nonvolatile memory to store data of the telephone portion (e.g., contacts and phone numbers) and the computer portion (e.g., application programs including a browser, pictures, games, videos, and music). The smartphone typically includes a camera (e.g., front-facing camera or rear camera, or both) for taking pictures and video. For example, a smartphone or tablet can be used to take live video that can be streamed to one or more other devices.

Enclosure 307 houses familiar computer components, some of which are not shown, such as a processor, memory, mass storage devices 317, and the like. Mass storage devices 317 may include mass disk drives, floppy disks, magnetic disks, optical disks, magneto-optical disks, fixed disks, hard disks, CD-ROMs, recordable CDs, DVDs, recordable DVDs (e.g., DVD-R, DVD+R, DVD-RW, DVD+RW, HD-DVD, or Blu-ray Disc), flash and other nonvolatile solid-state storage (e.g., USB flash drive or solid state drive (SSD)), battery-backed-up volatile memory, tape storage, reader, and other similar media, and combinations of these. In an implementation where the enclosure is a server system, mass storage devices may be housed outside of enclosure 307. In the server system implementation, the server may store and operate a server operating system.

A computer-implemented or computer-executable version or computer program product of the invention may be embodied using, stored on, or associated with a computer-readable medium. A computer-readable medium may include any medium that participates in providing instructions to one or more processors for execution. Such a medium may take many forms including, but not limited to, nonvolatile, volatile, and transmission media. Nonvolatile media includes, for example, flash memory, or optical or magnetic disks. Volatile media includes static or dynamic memory, such as cache memory or RAM. Transmission media includes coaxial cables, copper wire, fiber optic lines, and wires arranged in a bus. Transmission media can also take the form of electromagnetic, radio frequency, acoustic, or light waves, such as those generated during radio wave and infrared data communications.

For example, a binary, machine-executable version, of the software implementation may be stored or reside in RAM or cache memory, or on a mass storage device 317. The source code of the software of the implementation may also be stored or reside on mass storage device 317 (e.g., hard disk, magnetic disk, tape, or CD-ROM). As a further example, code of the invention may be transmitted via wires, radio waves, or through a network such as the Internet.

Figure 4:
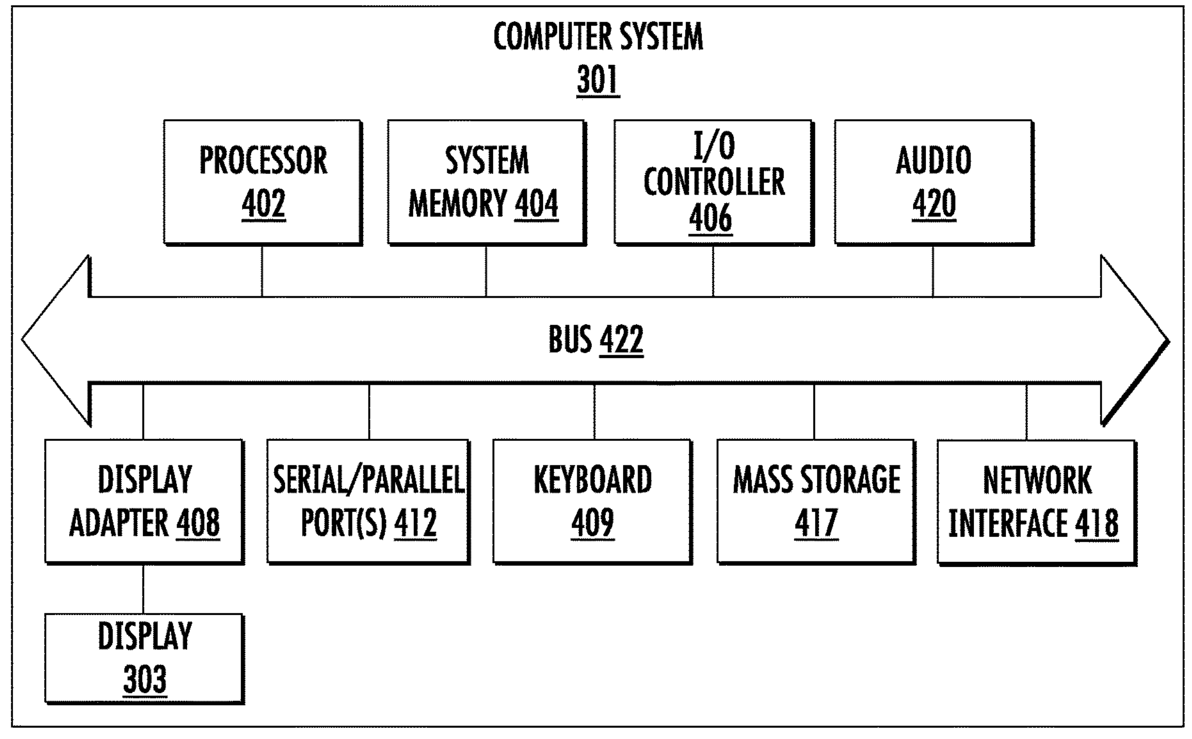
FIG. 4 shows a system block diagram of a computer system used to execute the computer code, in an implementation.

FIG. 4 shows a system block diagram of computer system 301 used to execute the computer code, in an implementation. As in FIG. 3, computer system 301 includes monitor 303, keyboard 309, and mass storage devices 317. Computer system 301 further includes subsystems such as central processor 402, system memory 404, input/output (I/O) controller 406, display adapter 408, serial or universal serial bus (USB) port 412, network interface 418, and speaker 420. The invention may also be used with computer systems with additional or fewer subsystems. For example, a computer system could include more than one processor 402 (i.e., a multiprocessor system) or a system may include a cache memory.

Arrows such as 422 represent the system bus architecture of computer system 301. However, these arrows are illustrative of any interconnection scheme serving to link the subsystems. For example, speaker 420 could be connected to the other subsystems through a port or have an internal direct connection to central processor 402. The processor may include multiple processors or a multicore processor, which may permit parallel processing of information. Computer system 301 shown in FIG. 4 is but an example of a computer system suitable for use with the present invention. Other configurations of subsystems suitable for use with the present invention will be readily apparent to one of ordinary skill in the art.

Computer software products may be written in any of various suitable programming languages, such as C, C++, C#, Pascal, Fortran, Perl, MATLAB (from MathWorks, www.mathworks.com), SAS, SPSS, JavaScript, AJAX, Java, Python, Erlang, and Ruby on Rails. The computer software product may be an independent application with data input and data display modules. Alternatively, the computer software products may be classes that may be instantiated as distributed objects. The computer software products may also be component software, such as Java Beans (from Oracle Corporation) or Enterprise Java Beans (EJB from Oracle Corporation).

An operating system for the system may be one of the Microsoft Windows® family of systems (e.g., Windows 95, 98, Me, Windows NT, Windows 2000, Windows XP, Windows XP x64 Edition, Windows Vista, Windows 7, Windows 8, Windows 10, Windows 11, Windows CE, Windows Mobile, Windows RT), Symbian OS, Tizen, Linux, HP-UX, UNIX, Sun OS, Solaris, Mac OS 15, Apple IOS, Android, Alpha OS, or AIX. Other operating systems may be used. Microsoft Windows is a trademark of Microsoft Corporation.

Any trademarks or service marks used in this patent are the property of their respective owners. Any company, product, or service names in this patent are for identification purposes only. Use of these names, logos, and brands does not imply endorsement.

Furthermore, the computer may be connected to a network and may interface with other computers using this network. The network may be an intranet, internet, or the Internet, among others. The network may be a wired network (e.g., using copper), telephone network, packet network, an optical network (e.g., using optical fiber), or a wireless network, or any combination of these. For example, data and other information may be passed between the computer and components (or steps) of a system of the invention using a wireless network using a protocol such as Wi-Fi (IEEE standards 802.11, 802.11a, 802.11b, 802.11e, 802.11g, 802.11i, 802.11n, 802.11ac, and 802.11ad, just to name a few examples), near field communication (NFC), radio-frequency identification (RFID), mobile or cellular wireless (e.g., 2G, 3G, 4G, 5G, 3GPP LTE, WiMAX, LTE, LTE Advanced, Flash-OFDM, HIPERMAN, iBurst, EDGE Evolution, UMTS, UMTS-TDD, 1×RDD, and EV-DO). For example, signals from a computer may be transferred, at least in part, wirelessly to components or other computers.

In an embodiment, with a Web browser executing on a computer workstation system, a user accesses a system on the World Wide Web (WWW) through a network such as the Internet. The Web browser is used to download Web pages or other content in various formats including HTML, XML, text, PDF, and postscript, and may be used to upload information to other parts of the system. The Web browser may use uniform resource identifiers (URLs) to identify resources on the Web and hypertext transfer protocol (HTTP) in transferring files on the Web.

In other implementations, the user accesses the system through either or both of native and nonnative applications. Native applications are locally installed on the particular computing system and are specific to the operating system or one or more hardware devices of that computing system, or a combination of these. These applications (which are sometimes also referred to as "apps") can be updated (e.g., periodically) via a direct internet upgrade patching mechanism or through an applications store (e.g., Apple iTunes and App store, Google Play store, Windows Phone store, and Blackberry App World store).

The system can run in platform-independent, nonnative applications. For example, a client can access the system through a Web application from one or more servers using a network connection with the server or servers and load the Web application in a Web browser. For example, a Web application can be downloaded from an application server over the Internet by a Web browser. Nonnative applications can also be obtained from other sources, such as a disk.

Figures 5, 6, 7:
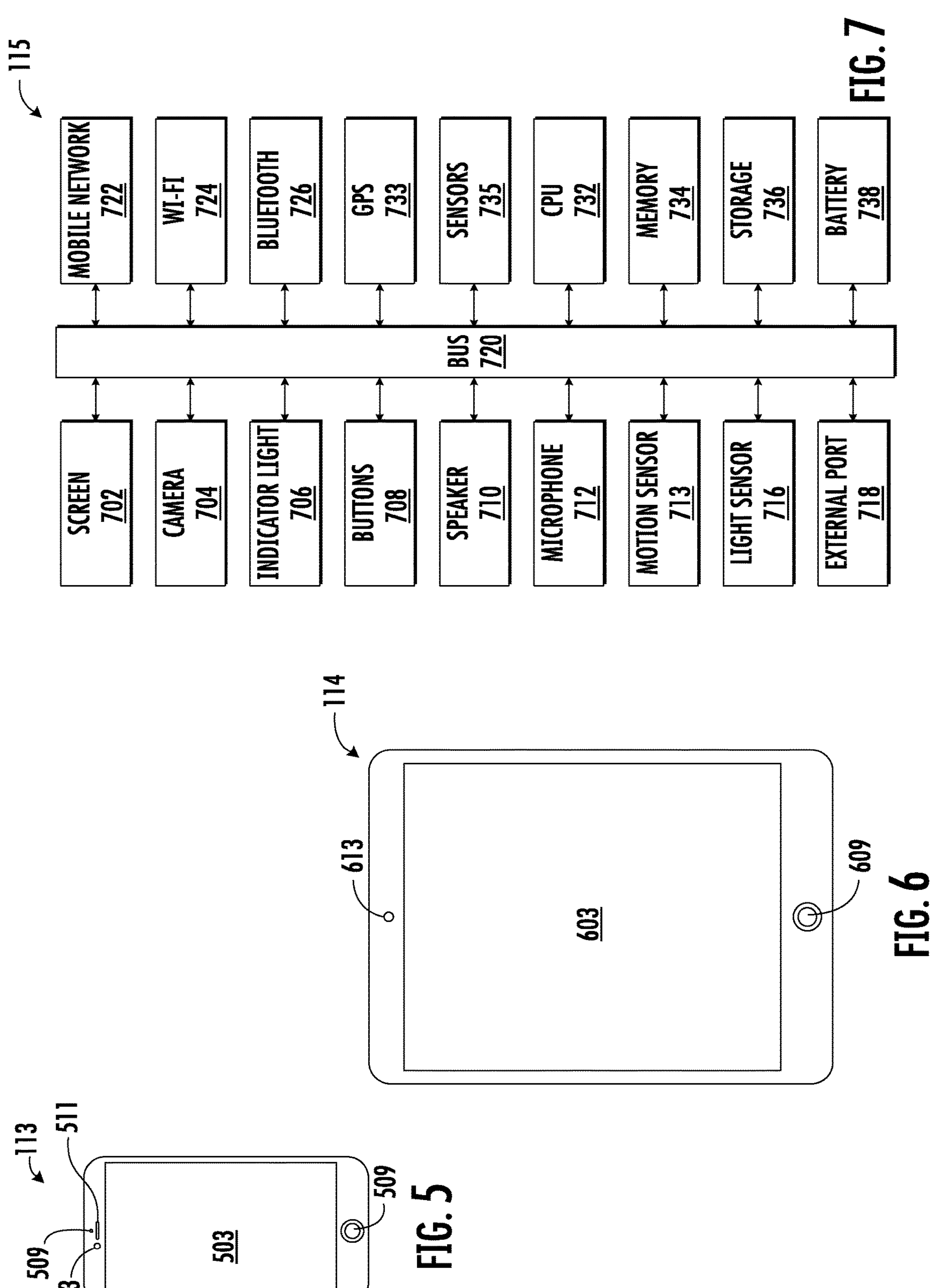
FIG. 5 shows an example medical device console that can include a smartphone device in which some of the various techniques described in this application may be implemented.
FIG. 6 shows an example medical device console.
FIG. 7 shows a simplified schematic diagram of an example medical device console.

FIG. 5 shows an example medical device console 113 that can include a mobile device, such as a smartphone device, in which some of the various techniques described in this application may be implemented. The medical device console includes, for example without limitation, a display 503, a front-facing camera 513, a rear-facing camera (not shown), a speaker or an array of multiple speakers 511, an optional proximity sensor 509, and a multi-function virtual or physical button 510 (e.g., for accessing one or more menus or home screen, for obtaining fingerprints for authentication and/or authorization, and others). In an implementation, the device shown in FIG. 5 may be the medical device console 112 shown in FIG. 2. In an implementation, the device of FIG. 5 may be a client system 108 shown in FIG. 1.

The medical device console can include a tablet computer, a mobile telephone, a desktop computer, a laptop computer, or another type of computing device. The medical device console can be a device of Teguar Corporation of Charlotte North Carolina, Apple Inc. of Cupertino California, Alphabet Inc. of Mountain View California, Microsoft Corporation of Redmond Washington, Sony Corporation of Tokyo Japan, Samsung Electronics Co. Seoul, South Korea, Ltd, Dell Technologies Inc. of Round Rock Texas, or other computer manufacturers.

FIG. 6 shows an example medical device console 114 that can include a tablet computing device in which some of the various techniques described in this application may be implemented. The medical device console includes, for example without limitation, a display 603, a front-facing camera 613, a rear-facing camera (not shown), a speaker or an array of multiple speakers (not shown), a multi-function virtual or physical button 609 (e.g., for accessing one or more menus or home screen, for obtaining fingerprints for authentication or authorization, and others). In an implementation, the device shown in FIG. 6 may be the medical device console 112 or 113 shown in FIGS. 2 and 5. In an implementation, the device of FIG. 6 may be a client system 108 shown in FIG. 1.

FIG. 7 shows a simplified schematic diagram of an example medical device console 114 in which some of the various techniques described in this application may be implemented. In an implementation, the device shown in FIG. 7 may be the medical device console 112 shown in FIG. 2. In an implementation, the device of FIG. 7 may be a client system 108 shown in FIG. 1. The medical device console of FIG. 7 may be the smartphone device 113 shown in FIG. 6 or the tablet computing device 114 shown in FIG. 7.

Medical device console 115 includes a bus 720 that operates according to a bus protocol to transfer data between components inside the console or between computers (e.g., between the console and one or more other computing devices). The components inside medical device console 115 and connected by bus architecture 720 may include a processor 732 (e.g., a central processing unit or CPU) that executes instructions from computer programs (including operating systems). The processor may include caches (e.g., L1, L2, or L3 cache, or any combination) and may utilize memory 734 (e.g., dynamic random-access memory or DRAM), as a cache where memory 734 may store instructions or computer code and data.

Medical device console 115 includes a storage device (e.g., persistent memory, a solid-state high-performance byte-addressable memory device, solid state drives, and others) 736 that stores computer programs and data such that it is typically persistent and provides more storage when compared to memory 734. Storage device 736 includes a removable storage device that provides mobility to computer programs and/or data that is stored in the storage device, in an implementation. The removable storage device can include a persistent memory or PRAM is a type of computer memory with the speed of RAM (random access memory), the retention of an SSD (solid state drive), and which remembers data even after powering off the device.

Memory 734 and storage device 736 provide examples of non-transitory computer readable storage media that may be utilized to store and retrieve computer programs incorporating computer codes that implement the invention, data for use with the invention, and the like. Additionally or alternatively, a data signal embodied in a carrier wave (e.g., in a network including the Internet) may be another form of a computer readable storage medium. These various components of a medical device console 115 may be powered by a battery 738 that may be charged via a charging circuit (not shown).

Medical device console 115 further includes a screen 702, one or more cameras 704 (e.g., a front-facing camera, a rear-facing camera, and others), one or more indicator lights 706, one or more physical buttons, virtual buttons, or switches 708, and a speaker or an array of multiple speakers 710. Medical device console 115 further includes one or more microphones 712 (e.g., an array of a plurality of microphones for beamforming, actively cancelling noises, controlling directional audio outputs, and others), and one or more sensors 713 (e.g., proximity sensor, motion sensor, or other sensors). Medical device console 115 further includes one or more light sensors 716 (e.g., photosensors or photodiodes) to sense and collect one or more characteristics of light. The light sensor may collect light intensity (e.g., representative of a human presence) and light color (e.g., red, green, or blue), illuminance in the unit of lux (e.g., the luminous flux as perceived by a surface and others), for example, to convert perceived light to electrical signals, in an implementation.

The medical device console 115 may include one or more display adapters (not shown) that function in conjunction with screen 702 to, for example, provide a user interface that accepts inputs and displays outputs. Medical device console 115 further includes one or more external ports 718. For example, a medical device console 115 may include a serial port that includes a serial communication interface through which information transfers in or out sequentially one bit at a time and/or a parallel port that includes an interface allowing the medical device console 115 to transmit or receive data down multiple bundled cables to a peripheral device (e.g., a printer).

The external port 718 can operate according to one or more protocols for interfacing with external devices. For example, the external ports 718 can include a lightning port, a Thunderbolt port, a USB-C port, and other ports for interfacing with external devices. The medical device console 115 can further include one or more networking or telecommunication modules, such as a mobile network module 722 for communication with a cellular network, a Wi-Fi network module 724 for communication with a Wi-Fi network, a Bluetooth connection 726 for communication with other Bluetooth enabled devices, other network modules, or any combination of the modules.

The medical device console 115 can further include a GPS module 733 connected to bus 720 that collects GPS signals from GPS satellites. The GPS signals may be used by various applications that operate on the console.

The medical device control can further include one or more sensors 735 that are connected to bus 720. The sensors can include various sensor types, such as tissue sensors of a user, heart rate, electrical conductivity of the user's skin, or other sensors.

Figure 8:
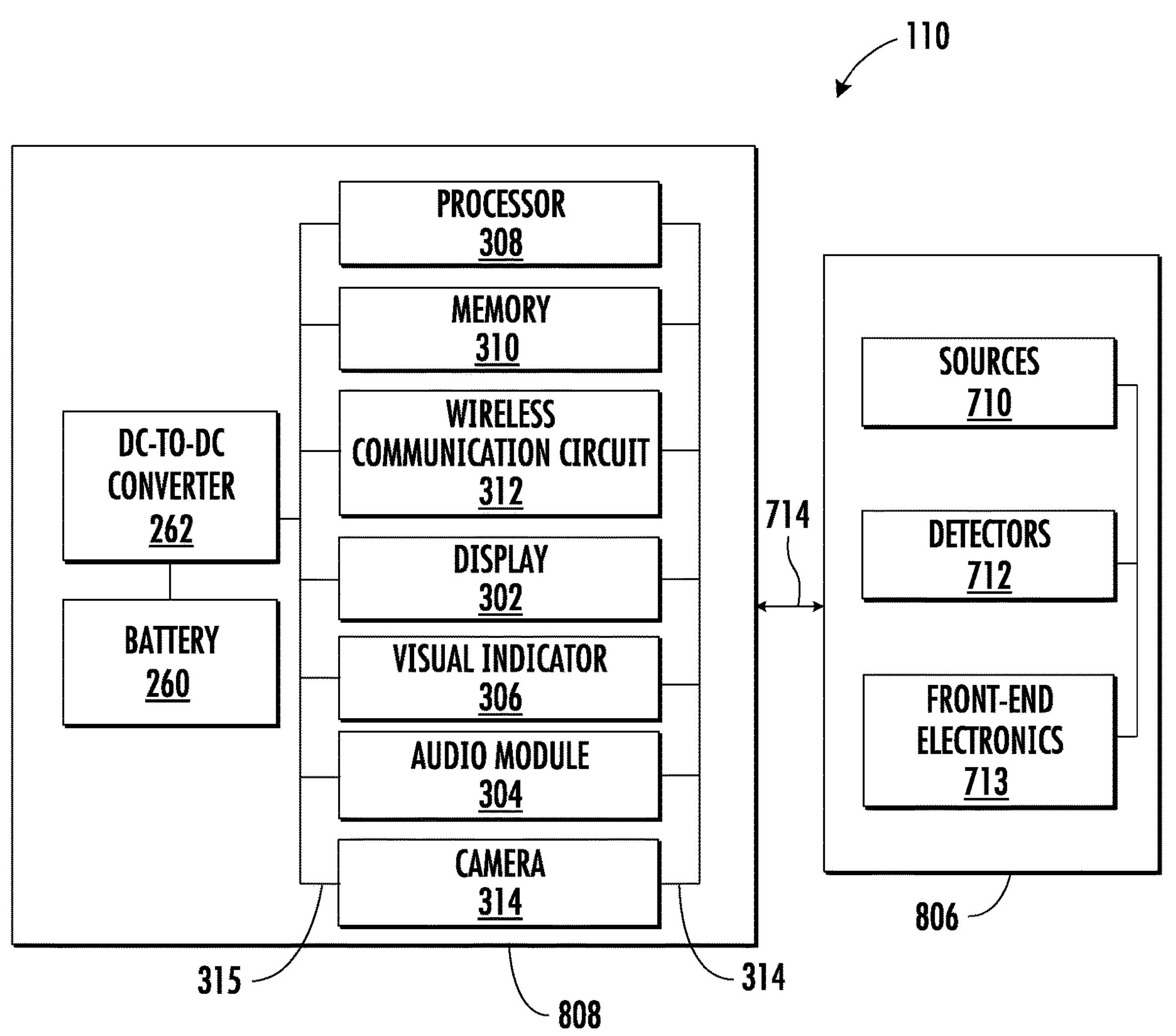
FIG. 8 shows an oximeter device, in an implementation.

FIG. 8 shows a block diagram of the oximeter device 110, in an implementation. The oximeter device 110 includes a sensor probe electronic module 808 connected to a sensor probe unit 806 via conductors 714. The sensor probe electronic module is sometimes referred to as a sensor probe electronic module and the sensor probe unit is sometimes referred to as a sensor head. Conductors 714 can include one or more conductors for a communication link and conductors for a power supply connection. The communication link can be a two-way communication link and the power supply connection can be a one-way power supply connection where the sensor probe electronic module 808 supplies DC power to the sensor probe unit 806.

The sensor probe electronic module 808 includes a processor 308, memory 310, and one or more wireless communication circuits 112 (such as a transceiver circuit) that can operate according to one or more transmission protocols, such as discussed above. For example, the wireless communication circuits can operate according to a Wi-Fi protocol, a mobile communication protocol (e.g., a cellular telephone protocol), a Bluetooth protocol, other protocols, or a combination of these protocols. The module further includes and a power source that includes a battery 260 and can include a DC-to-DC converter 262.

Sensor probe electronic module, in select implementations, includes a display 302, one or more visual indicators 306 (e.g., light indicators), an audio module 304 (e.g., one or more speakers), a camera 314, or any combination of these elements. Various implementations of module 808 do not include a display 302, do not include the one or more visual indicators 306 (e.g., light indicators), do not include the audio module 304, do not include camera 314, do not include any of these elements, or do not include any combination of these elements while including the others. Module 808 can include additional circuits or alternative circuits.

Module 808 further includes a communication bus 314 that connects the processor, memory, wireless communication circuit, display, visual indicator, audio module, and camera. The processor is connected to and controls memory, wireless communication circuit, display, visual indicator, audio module, and camera via bus 314. The processor can be a microprocessor, microcontroller, an application specific integrated circuit (ASIC), or other type of processing circuit.

The battery is connected to the DC-to-DC converter, in an implementation. The DC-to-DC converter is connected over a power distribution bus 315 to provide power to the processor, memory, wireless communication circuit, display, visual indicator, audio module, and camera. In an implementation that does not include a DC-to-DC converter, the battery is connected to the power distribution bus.

The processor, memory, wireless communication circuit, visual indicator, audio module, and camera are located inside a first housing of the sensor probe electronic module 808. The display can be connected to the housing where the display is visible from an exterior of the housing. One or both of the battery and DC-to-DC converter can be housed in the housing or housed in a battery compartment of the housing.

The DC-to-DC converter is also connected to a number of conductors (e.g., two conductors) of the conductors 714. Via conductors 714, the battery and DC-to-DC converter supply power to the sensor probe unit 806. More specifically, the battery and DC-to-DC converter supply power to one or more circuits included in the sensor probe unit 806. Circuits included in the sensor probe unit are housed in a second housing. Circuits included in the second housing are described below.

In an implementation, processor 308 is configured to communicate with sensor probe unit 806 over conductors 714. In an implementation where the conductors are a wired communication link in electrical cable 1604, the electrical cable (e.g., the wired communication link and power supply link) can be about 1 centimeter to about 1 meter or longer. The electrical cable (e.g., the wired communication link and power supply link) can include 4 or more wires, such as 6 wires to provide power, ground, and control signals to probe unit 806 and to receive oximetry measurement information from sensor probe unit 806.

Memory 310 can include a nonvolatile memory (e.g., FLASH memory), volatile memory (e.g., RAM, such as SRAM or DRAM or both), or both. The memory can store the oximetry information along with time stamps, where the time stamps are associated with the stored oximetry information. The time stamps can be real-time values or relative time values. The time stamps can include time stamps for the time the front-end electronics collects each piece of oximetry information from the source detectors. In an implementation, processor 308 can also include memory, such as volatile memory.

Sensor probe unit 806 can include one or more light engines (not shown), which are coupled to one or more of source structures 710 and can include one or more photodetectors (not shown), which are coupled to one or more of detector structures 712. The sensor probe unit further includes front-end electronics 713, which are connected to the light engine and photodetectors. The front-end electronics 713 are configured to communicate over communication link 714 with the sensor probe electronic module 808. Front-end electronics 713 may include an analog front end (AFE) integrated circuit, other ICs, and various discrete components. In an implementation, the AFE (e.g., AFE4404) is produced by Texas Instruments Incorporated of Dallas Texas.

Sensor probe unit 806 is configured to attach to patient tissue (e.g., breast tissue) for making oximetry measurements of the tissue. More specifically, the light engines generate two or more wavelengths of light that may be transmitted from the light sources into patient tissue. The wavelengths can include wavelengths in the visible spectrum and near-infrared (NIR) wavelengths. The wavelengths can include wavelengths of 690 nanometers, 830 nanometers, other wavelengths, or combinations of these wavelengths. The wavelengths may not include wavelengths for the isosbestic point of the chromophores of patient tissue, in one specific implementation.

The AFE in the front-end electronics can provide control signals to the light engine for light generation. The light engine can include two or more light sources, such as LEDs, laser LEDs, lasers, or other types of light sources. In an implementation, the light engine includes four light sources, such as four LEDs. The control signals have an amplitude, frequency, and a duty cycle to control the generation of light by the LEDs so that the generated light has a select amplitude, pulse frequency, and duty cycle. In an alternative implementation, processor 308 provides control signals to the LEDs of the light engine to control the generation and emission of light from the LEDs through the source structures 710 to patient tissue.

After entering patient tissue, the light is absorbed and scattered by chromophores in the patient tissue, such as oxygenated hemoglobin, deoxygenated hemoglobin, fat, water, melanin, and other molecules in the tissue. A portion of the light that is transmitted out from the tissue (e.g., reflected back) is received by one or more of detector structures 712 and includes oximetry information for the patient tissue.

After the photodetectors of the detector structures collect reflected light or transmitted light from patient tissue, the photodetectors generate measurement signals, which are amplified by one or more amplifiers included in the front-end electronics. The amplifiers can include a transimpedance amplifier (TIA), a fixed gain amplifier, a processor-controlled amplifier, or any combination of these amplifiers. The amplifiers can form a portion of the AFE or can be circuits that are not included in the AFE. Amplified electrical signals can be digitized by an analog-to-digital converter included in the front-end electronics, such as in the AFE.

The front-end electronics can control the transfer of the digitized measurement signals across communication link 714 to processor 308. The digitized measurement signal are sometimes referred to as raw measurement signal. Processor 308 is configured to use these raw measurement signals to generate oximetry information, in an implementation. The oximetry information can include oxygen saturation values, chromophore percentages in the patient tissue (e.g., oxygenated hemoglobin percentages and deoxygenated hemoglobin percentages), absorption coefficients ua, scattering coefficients us, quality metric values that indicate qualities of the oxygen saturation values, other oximetry values, or any combination of these values. Memory 310 can store the raw measurement signals, the oximetry information, one of these information, and time stamps for one or both of these information.

In an implementation, processor 308 is configured to control the transfer of the raw measurement signals to the medical device console 112, where the processor of the console is configured to use the raw measurement signals to generate the oximetry information. The oximetry information generated by the console can include oxygen saturation values, chromophore percentages in the patient tissue (e.g., oxygenated hemoglobin percentages and deoxygenated hemoglobin percentages), absorption coefficients ua, scattering coefficients us, quality metric values that indicate qualities of the oxygen saturation values, other oximetry values, or any combination of these values. Memory 310 can store the raw measurement signals, the oximetry information, one of these information, and time stamps for one or both of these information.

In an implementation, the sensor probe unit 806 includes a processor that is configured to use the raw measurement signals to generate oximetry information. The oximetry information can include oxygen saturation values, chromophore percentages in the patient tissue (e.g., oxygenated hemoglobin percentages and deoxygenated hemoglobin percentages), absorption coefficients ua, scattering coefficients us, quality metric values that indicate qualities of the oxygen saturation values, other oximetry values, or any combination of these values. This oximetry information can be transferred to the electronic module for storage, display, or both. This oximetry information can be transferred from the sensor probe electronic module 808 to the medical device console 112 for storage, display, or both.

In this implementation and other implementations described in this application, the sensor probe unit 806 can include a power source that includes a battery 260 and a DC-to-DC converter 262 for powering the modules, such as a processor, located in the sensor probe unit.

The processor of the sensor probe electronic module 80 can also generate a quality metric for the oximetry information. The quality metric information can be stored in the memory, where each oximetry measurement can be associated with uniquely generated quality metric information for the oximetry measurement. The quality metric information can be displayed on display 302. The quality metric information can also be transmitted to the medical device console 112 for storage and display.

Processor 308 controls the transfer of the oximetry information, the time stamps, the quality metric information, and other information to console 112 across communication link 114. The console can display this information. More specifically, a medical device application stored by the console and configured to be operated by the console can generate display information based on the oximetry information for display of the oximetry information on the console's display. In an implementation, the medical device application is configured to generate the display information so that the information fills the display of the console in a landscape orientation, as shown in FIG. 9, which is described further immediately below.

Figure 9:
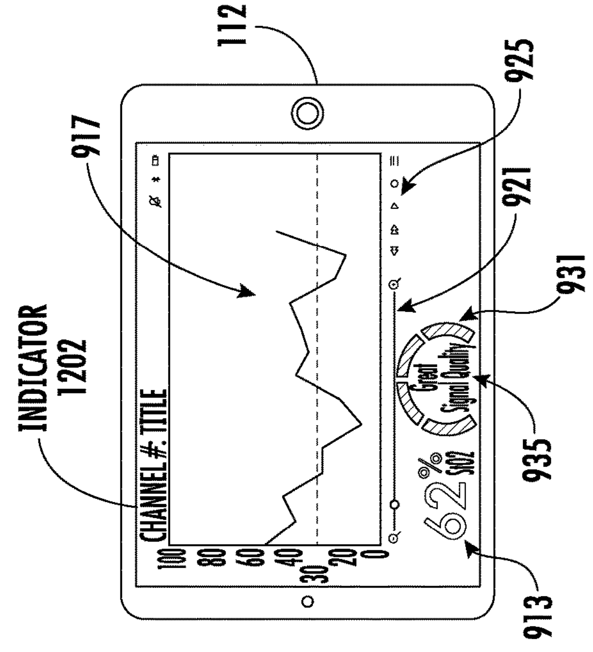
FIG. 9 shows displayed oximetry information, in an implementation.
Figure 9:
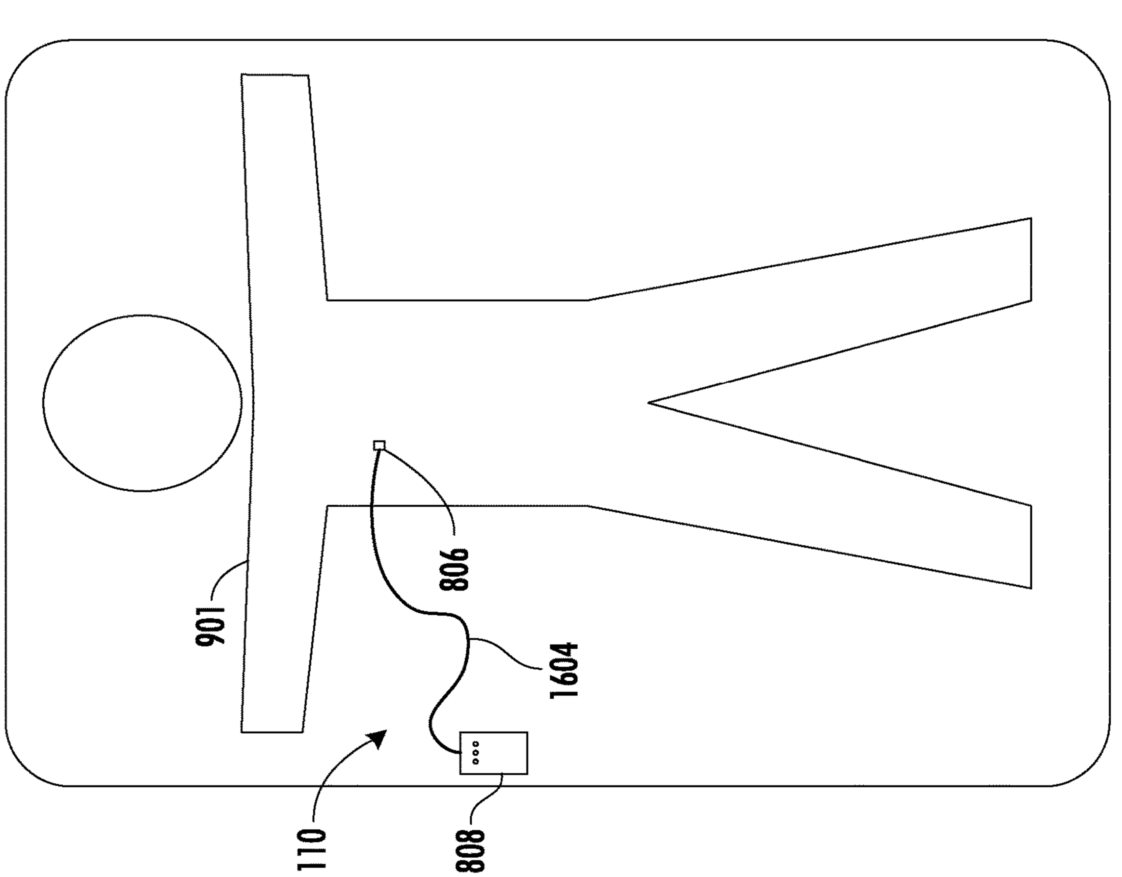

FIG. 9 shows a patient 901 having an oximetry device 110 attached to the patient's tissue to be measured, such as before, during, and after surgery. The patient may be in a hospital and on an operating table for the surgery, such as a breast reconstruction surgery. The sensor probe unit 806 of the oximetry device 110 is attached to the patient tissue. The sensor probe electronic module 808 is attached to the sensor probe unit 806 via flexbile electrical cable 1604. The sensor probe electronic module 808 may be attached to the operating table or placed next to the patient on the operating table. The sensor probe electronic module is wirelessly connected to the medical device console 112. The medical device console can display oximetry information as described above and additional information, such as information about the oximetry device.

In an implementation, conductors 714 can be wires that are bundled in electrical cable 6104. The wires can be inside an outer casing of electrical cable 1604. Each wire can be located inside an outer casing to electrically isolate the wires from each other. The electrical cable 1604 can be a flexible cable. Flexibility of the electrical cable allows the sensor probe electronic module 808 to be moved relative to the sensor probe unit 806. Accordingly, the sensor probe electronic module can be moved without pulling on the sensor probe unit attached to patient tissue that is being monitored by the oximetry device. Thus, patient tissue, such as a tissue flap that is being used for a breast reconstruction or that is healing from breast reconstruction, will not be pulled on by the sensor probe unit 806 attached to the patient tissue as the sensor probe electronic module 808 is moved.

The flexibility of the electrical cable lowers the chance of complications from surgery by lowering the chance that movement of the sensor probe electronic module will result in the sensor probe unit 806 being pulled on. Thus, the chance of complications from necrosis for other complications is lowered and the likelihood of a successful surgery is increased. In various implementations, the sensor probe electronic module 808 may be moved when the patient is moved from surgery to another location after surgery, such as a recovery room, a recovery facility, a patient's home, or another location.

FIG. 9 shows that information displayed on the display of the console 112 can include a real-time value 913 (e.g., 62% StO2) for the oxygen saturation of patient tissue and a graph 917 of the oxygen saturation values over time. The displayed information can include a screen controller 921 (e.g., a slider bar) for increasing or decreasing the time period over which oximetry saturation values are displayed on graph 917. The displayed information can include a set of control 925 (e.g., play button, pause button, reverse button, and a fast forward button) for controlling the graph.

The displayed information can include a quality metric indicator that indicates the quality of the real-time value 913 of the oxygen saturation value. The quality metric indicator includes a bar chart 931 that includes higher numbers of bars (e.g., 4 bars or 3 bars) to indicate a relatively high quality metric for the displayed oxygen saturation value 913 or fewer bars (e.g., 2 bars or 1 bar) for lesser quality metric values. The bar of the bar chart can be displayed in different colors when different numbers of bars are displayed, such as green for 4 bars, yellow for 3 bars, orange for 2 bars, red for 1 bar, and grey for 0 bars. Text 935 can also be displayed to indicate the quality metric, such as "great signal quality' for 4 bars, "good signal quality" for 3 bars, "fair signal quality" for 2 bars, "poor signal quality" for 1 bar, and "no contact" for 0 bars.

Figure 10:
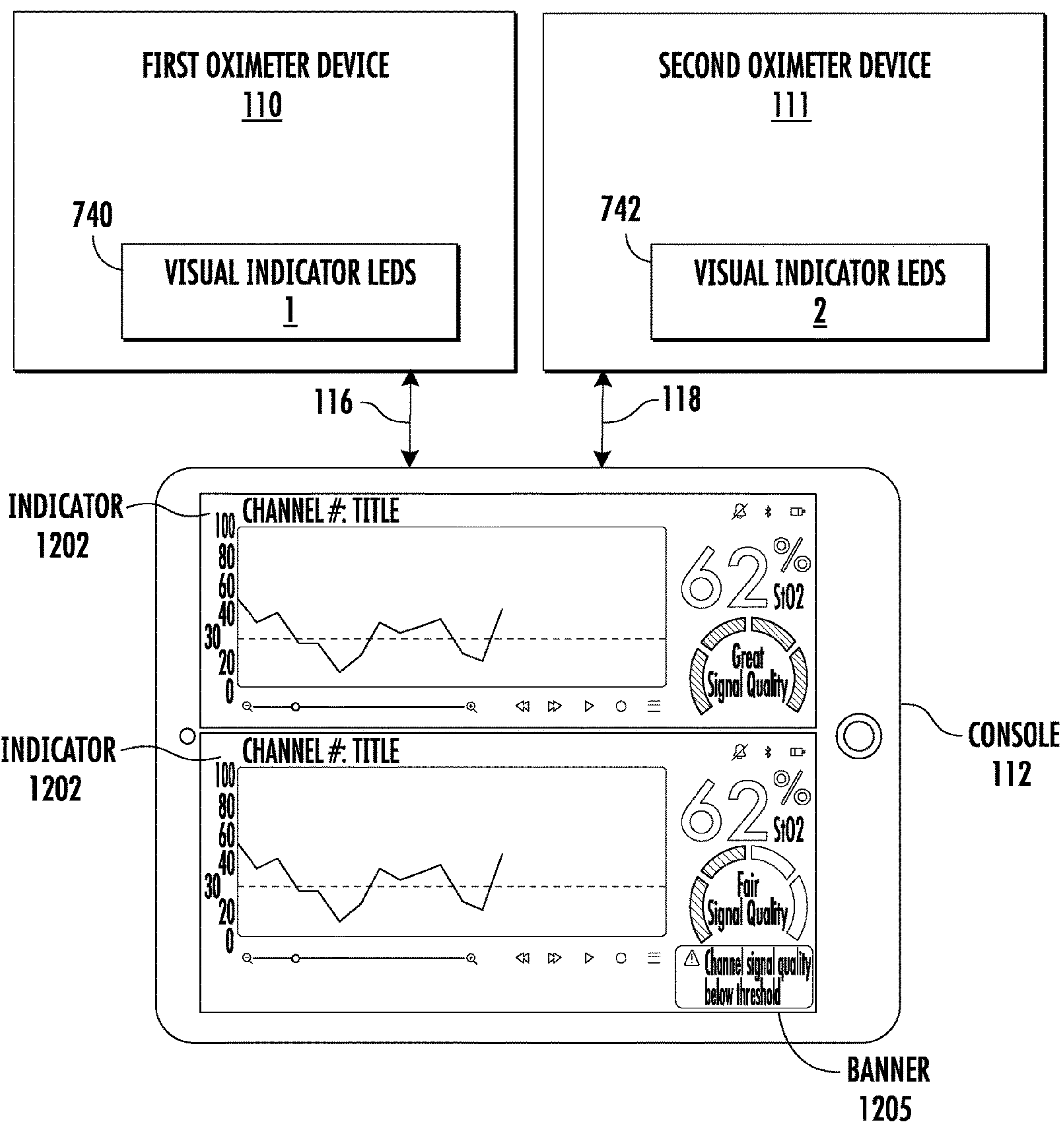
FIG. 10 shows the displayed quality metric information in a banner, in an implementation.

A banner can also be displayed to indicate the quality metric value. An example banner 1205 is shown in FIG. 10. The banners can be colored to match the colors of the displayed bars in the bar chart and can include text in the banners. For example, the yellow banner can include the text: "channel signal quality above threshold," the orange banner can include the text: "channel signal quality below threshold," and the red banner can include the text: "critical error." A banner might not be displayed for a high-quality metric value for 4 bars in the bar chart. FIG. 10 is described further below.

Referring again to FIG. 8, battery 260 may include one or more disposable battery cells, such as alkaline battery cells (e.g., size AA, AAA, N, CR123, 18650, or others), or one or more rechargeable battery cells, such as nickel-metal hydride, lithium battery cells (e.g., Li/FeS2 size AA, AAA, N, CR123, 18650, or others), lithium polymer, or other types of cells. The battery may include one or more (e.g., two or more) battery cells that are AA size cells that output 1.5 volts. The two batteries may be in series to output 3 volts, or may be in parallel to output 1.5 volts.

The DC-to-DC converter converts a first voltage output from the battery to a second voltage that is different from the first voltage where the second voltage is usable by the light engine, the photodetectors, and the front end electronics, such as about 3.3 volts to about 5 volts.

In an implementation, the battery includes sufficient stored energy to operate oximeter device 110 for one or more days, such as two days. Thus, the battery may include relatively large batteries, such as two AA batteries. The oximeter device may be run for one or more days so that the oximeter device can be used with a single patient from before a medical procedure, through the duration of a medical procedure (e.g., breast reconstruction surgery), and after the medical procedure during a recovery period.

Memory 310 of the sensor probe electronic module 308 is configured to continue to store oximetry information after battery 260 runs out of stored energy. Battery 260 may (e.g., two AA batteries) be removed from module 808 and disposed of after the battery runs out of stored energy and replaced with another battery 260 (e.g., two new AA batteries). After a new battery 260 is installed in the module 808, the processor can access oximetry information stored in memory 310 that was stored in the memory before battery 260 ran out of stored energy.

In an implementation, wireless communication circuit 312 includes one or more types of wireless communication circuits. The one or more types of communication circuits can operate according to one or more types of communication protocols, such as any one or more of the communication protocols described above. In an implementation, the wireless communication circuits can include a Wi-Fi communication circuit (e.g., a Wi-Fi chipset) or another internet wireless circuit, a mobile communication circuit (e.g., a cellular telephone communication circuit or chipset), a RF communication circuit (e.g., a Bluetooth chipset), other types of communication circuits, or any combination of these communication circuits.

In an implementation where the wireless communication circuit 312 includes a Wi-Fi communication circuit or another wireless internet circuit, the oximeter device 110 can communicatively connect to a router. The router can be a router located at the hospital where a medical procedure (e.g., a breast reconstruction surgery) takes place, at the hospital where a patient enters recovery, at a rehabilitation facility, at a private residence, such as a patient's home, in a vehicle, or another location.

Tables 1-4 below show various implementations of the medical device system 102. Table 1 below shows a configuration of the medical device system described above, where the light engine and photodetectors are located in the sensor probe unit 806.

Table 2 below shows a configuration of the medical device system where the light engine and photodetectors are located in the sensor probe electronic module 808. One or more optical conductors link the light engine to the source structure, and one or more optical conductors link the detector sources to the photodetectors. In the implementation shown in table 2, the oximeter device 110 may not include an electrical cable that links the sensor probe electronic module 808 to the sensor probe unit 806. In the implementation of table 2, the front end electronics may be located in the sensor probe electronic module.

Table 3 below shows a configuration of the medical device system where the light engine is located in the sensor probe electronic module 808 and the source structures are located in the sensor probe unit 806. One or more optical conductors link the light engine to the source structures. The detector structures and photodetectors are located in the sensor probe unit 806. An electrical cable links the sensor probe electronic module 808 and the sensor probe unit 806. In the implementation of table 2, the front end electronics may include two modules, where a first module is located in the sensor probe electronic module and a second module is located in the sensor probe unit.

Table 4 below shows a configuration of the medical device system where the photodetectors are located in the sensor probe electronic module 808 and the detector structures are located in the sensor probe unit. One or more optical conductors link the detector structures and the photodetectors. An electrical cable links the sensor probe electronic module 808 and the sensor probe unit 806. In the implementation of table 2, the front end electronics may include two modules, where a first module is located in the sensor probe electronic module and a second module is located in the sensor probe unit.

TABLE 1

| Implementation 1<br>Medical Device System 102 | | | | |
|---|---|---|---|---|
| Medical Device Console 112 | Interface 114 | Sensor Probe Electronic Module 808 | Interface 714 | Sensor Probe Unit 806 |
| Application<br>Display<br>Transmitter | Wireless link ⟷<br>← transfer oximetry information, such as StO2 values and quality metric values Or<br>← transfer raw measurement information | Processor<br>Memory<br>Wireless communication circuit<br>Battery and DC-to-DC converter | Electrical cable ⟷<br>transfer control signals →<br>transfer power →<br>← transfer measurement signals | Front-End Electronics<br>Detector structures<br>Photodetectors<br>Source structures<br>Light engine |

TABLE 2

| Implementation 2 Medical Device System 102 | | | | |
|---|---|---|---|---|
| Medical Device Console 112 | Interface 114 | Sensor Probe Electronic Module 808 | Interface 714 | Sensor Probe Unit 806 |
| Medical Device Application | Wireless link ⟷ | Processor | Optical conductor ⟷ | Source structures |
| Display Transmitter | ← transfer oximetry information, such as StO2 values and quality metric values Or ← transfer raw measurement information | Memory Wireless communication circuit Battery and DC-to-DC converter Light engine Photodetectors Front-End Electronics | Transmit generated light → Transmit received light ← | Detector structures |

TABLE 3

| Implementation 3 Medical Device System 102 | | | | |
|---|---|---|---|---|
| Medical Device Console 112 | Interface 114 | Sensor Probe Electronic Module 808 | Interface 714 | Sensor Probe Unit 806 |
| Medical Device Application Display | Wireless link ⟷ ← transfer oximetry | Processor Memory | Electrical cable ⟷ transfer | Front-End Electronics Detector structures |
| Transmitter | information, such as StO2 values and quality metric values | Wireless communication circuit Battery and DC-to-DC converter | control signals → transfer power → ← transfer measurement signals | Photodetectors |
| | Or ← transfer raw measurement information | Light engine | Optical conductors ⟷ Transmit generated light → | Source structures |

TABLE 4

| Implementation 4 Medical Device System 102 | | | | |
|---|---|---|---|---|
| Medical Device Console 112 | Interface 114 | Sensor Probe Electronic Module 808 | Interface 714 | Sensor Probe Unit 806 |
| Medical Device Application Display | Wireless link ⟷ ← transfer | Processor Memory | Electrical cable ⟷ | Source structures |
| Transmitter | oximetry information, such as StO2 | Wireless communication circuit | transfer control signals → | Light engine |

TABLE 4-continued

| Implementation 4 Medical Device System 102 | | | | |
|---|---|---|---|---|
| Medical Device Console 112 | Interface 114 | Sensor Probe Electronic Module 808 | Interface 714 | Sensor Probe Unit 806 |
| | values and quality metric values Or ← transfer raw measurement information | Battery and DC-to-DC converter | transfer power → | |
| | | Photodetectors Front-End Electronics | Optical conductors ←→ Transmit received light → | Detector structures |

Referring again to FIG. 9, FIG. 9 shows a patient where an oximeter device 110 is connected to a patient 901. The patient can be in a hospital, in a vehicle (such as an ambulance or personal vehicle), at a medical office (e.g., a doctor's office, rehabilitation facility, or other office), at a sports event, in a home, or other location. The sensor probe unit 806 of the oximeter device 110 is connected to patient tissue, such as the patient's breast tissue, where a breast reconstruction surgery is to be performed. The sensor probe unit 806 is connected to sensor probe electronic modules 808 via an electrical cable connection. The sensor probe electronic module 808 is wirelessly connected to the medical device console 112.

The medical device application operating on the medical device console 112 can control the operation of the oximeter device for collecting oximetry information from the patient. The medical device application can allow oximetry information for the probe to be displayed on the display of the medical device console. The medical device application provides a screen button, slider, or other screen options for controlling the oximeter device system 110.

FIG. 10 shows an implementation where the oximetry information for two oximeter devices 110 and 111 (i.e., oximetry devices) are coupled to patient tissue, such as a single breast for surgery, or contralateral patient tissue, such as two breasts where one breast may be operated on for breast reconstruction surgery, for example. The oximeter devices 110 and 111 can be wirelessly connected to the medical device console over wireless communication links 116 and 118. Oximetry information generated by both of the oximeter devices can be transmitted to the medical device console via the communication links.

The medical device application operating on the medical device console provides a screen that displays oximetry information from both of the oximeter devices. The medical device application provides a screen button, slider, or other screen options for selecting the display of oximetry information for one or both oximeter devices 110 and 111 on the display.

In an implementation, each oximeter device 110 and 111 includes a visual indicator 740 and 742, such as LEDs, that indicates a unique identifier for each oximeter device. The visual indicators 740 and 741 for the oximeter devices 110 and 111 can be on the housing for the sensor probe units 806 that are attached to patient tissue or on the housing for the sensor probe electronic modules 808. The visual indicators can be displayed on a display, by lights (e.g., LEDs), or other devices. In an implementation, the visual identifier provides an indication via a combination of the lights (e.g., LEDs) being lighted. In an implementation, the sensor probe electronic modules 808 of the oximeter devices 110 and 111 are housed in housings, the housings are at least semitransparent to light transmission from LEDs located in the housing. In an example implementation, the visual indicator of sensor device 110 can have 1 lighted LED to indicate oximeter device 110 and the visual indicator of sensor device 110 can have 2 lighted LEDs to indicate oximeter device 111.

In an implementation, the oximeter information that is displayed on the display can include an indicator 1202 that identifies the particular oximeter device that the displayed oximeter information is associated with. For example, the top oximetry information displayed on the display of the medical device console 112 can be generated by oximeter device 110 that is attached to the patient's left breast, for example, and the bottom oximetry information displayed on the display of the medical device console can be generated by oximeter device 111 located on the patient's right breast. The top indicator 1202 may match the indicator displayed oximeter device 110. For example, if oximeter device 110 lights one visual indicator LED, the top indicator may light one dot or bar in a series of dots or bars to match the one lighted visual indicator LED of oximeter device 110. The bottom indicator 1202 may match the indicator displayed oximeter device 111. For example, if oximeter device 110 lights two visual indicator LEDs, the bottom indicator may light two dot or two bar in a series of dots or bars to match the two lighted visual indicator LEDs of oximeter device 111. Thus, the displayed oximetry information in the top and bottom displays of the medical device console can be connected with the particular oximeter device providing the information and the oximetry information displayed in the top and bottom displays can be correlated with the particular patient tissue being measured, such as the patient's left and right breast tissue.

In the implementation shown in FIG. 10, oximeter devices 110 and 111 are wirelessly coupled to the medical device console 112 by independent wireless links 116 and 118. Thus, one of the sensor probe units 806 for one of the oximeter devices (e.g., oximeter device 110) can be removed from patient tissue without effecting the other sensor probe unit 806 for a different oximeter device (e.g., oximeter device 111). Further, the number of oximeter devices that be used with a patient is limited to the number of wireless links allowed by the wireless protocol used by the medical device console 112. For example, if the medical device console 112 uses a wireless connection and protocol that allows for n number of links (e.g., 2, 3, 4, 5, 6, 7, 8, 9, 10, 11, 12, or more links), then n number of oximeter devices may be used with a patient.

Figure 11:
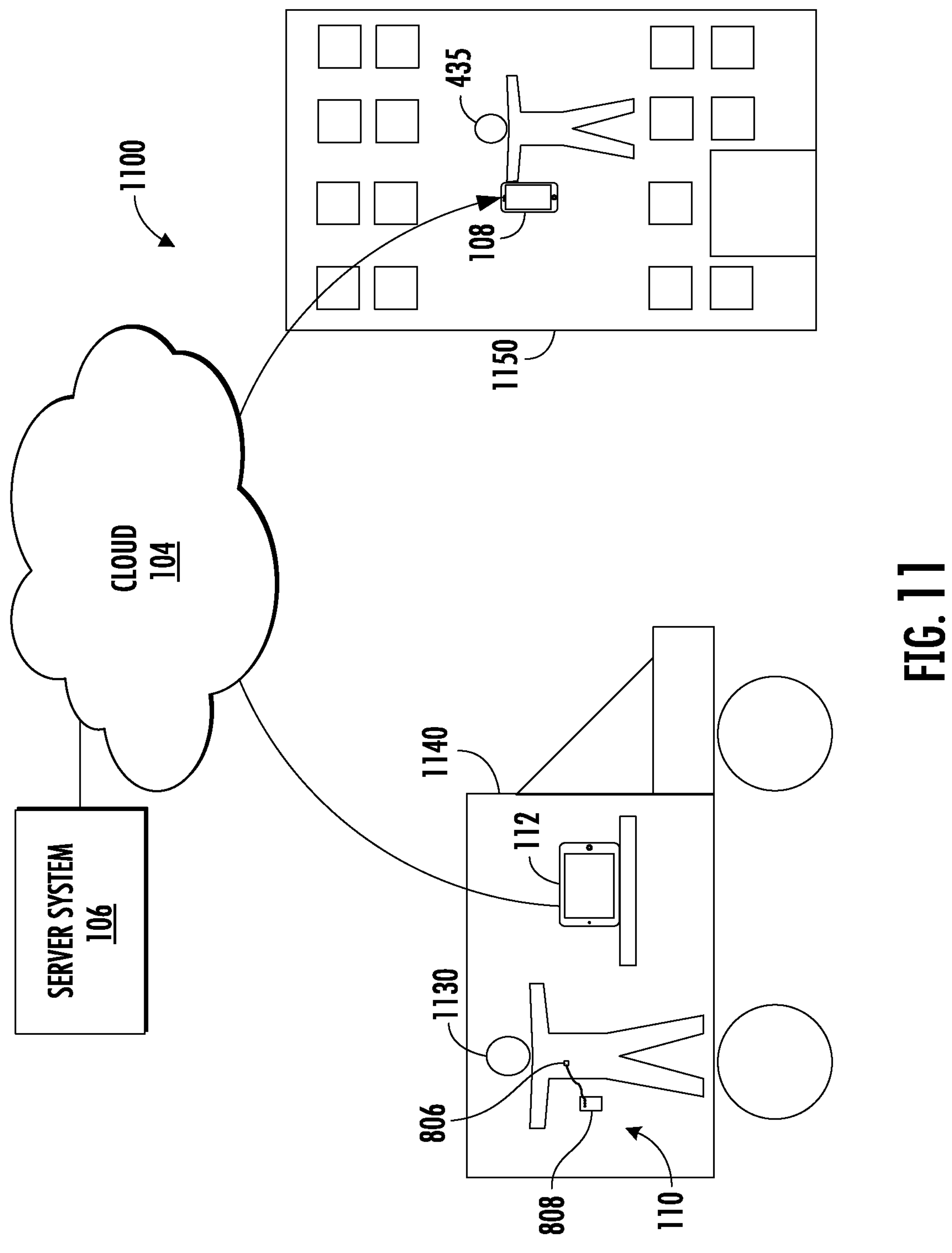
FIG. 11 shows a use environment for the medical communication system shown in FIG. 1.

FIG. 11 shows a use environment 1100 for the medical communication system 100 shown in FIG. 1 and described above. In the use environment shown in FIG. 11, a patient 1130 is being transported in a vehicle 1140, such as an ambulance. The vehicle may be headed to a medical facility 1150, such as a hospital. In the vehicle, a sensor probe unit 806 of an oximeter device 110 is connected to patient tissue. The sensor probe electronic module 808 of the oximeter device is connected to the sensor probe unit and is wirelessly connected to the medical device console 112. The oximeter device 110 may generate oximetry information for the patient as described and the information may be wirelessly transmitted from the oximeter device to the medical device console.

In the use environment, the oximetry information is transmitted up to the cloud 104 (e.g., Internet, intranet, or other network elements described above) from the medical device console, such as by a Wi-Fi connection, a cellular connection, or other connection. The oximetry information may be transmitted through the cloud to the server system 106, which stores the oximetry information. The oximetry information may be transmitted to the server system via a WiFi connection or other types of connections.

The oximetry information may be retrieved from the server system 106 by a client system 108. The oximetry information can be requested or pushed to the client system and can be delivered to the client system via a Wi-Fi connection, a cellular connection, or another type of connection provided by the cloud or local networks. The client system can store and operate a medical device application that provides for the display of the oximetry information on the display of the client system. The oximetry information can be displayed on the client system the same or similarly to the oximetry information displayed on the medical device consoles as shown in FIGS. 9 and 10.

The client system 108 can be located at a variety of locations, such as a medical facility 1150 or hospital where a medical professional (e.g., a doctor, nurse, or another medical professional) uses the client system to view the oximetry information. In an implementation, the client system 108 is adapted to store the oximetry information and any other information transmitted with the oximetry information, such as quality metric information and any time stamps for the oximeter information and quality metric information. When the patient arrives at the medical facility, the medical professional can continue to sue the client system 108 to review the oximetry information for the patient or can switch to using a medical device console 112 for viewing the oximetry information. The client system 108 allows the medical profession to assess the patient's health while the patient is in transport and prepare to treat the patient based on the oximetry information displayed on the client system or can communicate with a medical professional or others monitoring the patient's oxygen saturation in the vehicle to advise the medical professional in the vehicle how to treat the patient.

Figure 12A:
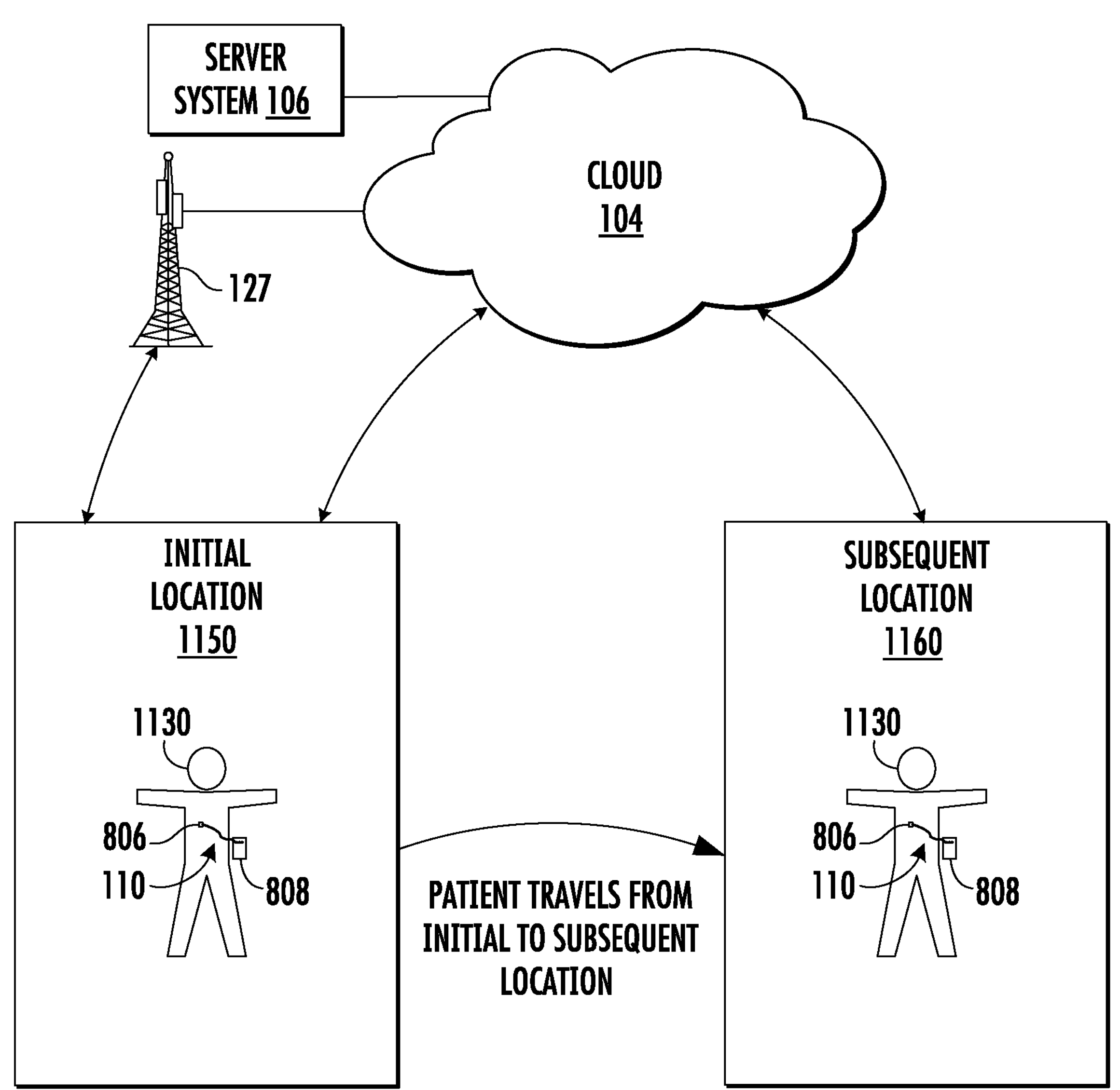
FIG. 12A shows a use environment for the medical communication system shown in FIG. 1 where a patient, who is connected to an oximeter device for patient monitoring, travels from an initial location with the oximeter device to a subsequent location with further patient monitoring by the oximeter device.

FIG. 12A shows a use environment for the medical communication system shown in FIG. 1 where a patient 1130 travels from an initial location 1150 with patient monitoring by an oximeter device 110 to a subsequent location 1160 with patient monitoring by the oximeter device.

The initial location can be a medical facility, such as a hospital, urgent care center, surgery center, medical office, recovery center, or other type of medical facility. The initial location can be a vehicle, such as an ambulance, car, recreational vehicle, vessel, or other type of vehicle. The initial location can be a residence, such as a home, apartment, condominium, multiplex (e.g., a duplex), a townhouse, manufactured home, tiny home, assisted living center, or other dwelling place. The subsequent location can be a medical facility, such as a hospital, urgent care center, surgery center, medical office, recovery center, or other type of medical facility. The subsequent location can be a vehicle, such as an ambulance, car, recreational vehicle, vessel, or other type of vehicle. The subsequent location can be a residence, such as a home, apartment, condominium, multiplex (e.g., a duplex), a townhouse, manufactured home, tiny home, assisted living center, or other dwelling place.

At the initial location, the oximeter device 110 is attached to patient tissue for making oximetry measurements. At the initial location, the oximeter device is connected to network 104 and to server system 106 via the network. At the subsequent location, the oximeter device 110 is connected to network 104 and to server system 106 via the network.

At the initial location, the oximeter device can generate oximetry information, such as oxygen saturation information, and transfer the oximetry information to the sever system 106 via the network 104. At the initial location, the senor probe can be attached to patient tissue, such as tissue that is to be transplanted, a tissue flap, a patient's breast for a breast reconstruction surgery, or another tissue. The generated oximetry information can include raw oximetry measurement data, processed oximetry data, or both. Raw oximetry data can include digitized photodetector measurement values. The processed oximetry date can include oxygen saturation values, percentage of oxygenated hemoglobin, percentage of non-oxygenated hemoglobin, absorption coefficient, scattering coefficient, other information, or any combination of this information. Oximetry information located on the system server can be accessed remotely as described above with respect to FIGS. 11 and 12A above.

At the subsequent location, the oximeter device can generate oximetry information, such as oxygen saturation information, and transfer the oximetry information to the sever system 106 via the network 104. At the initial location, the senor probe can be attached to patient tissue, such as tissue that has been reconstructed, such as a patient's breast after a breast reconstruction surgery. The generated oximetry information can include raw oximetry measurement data, processed oximetry data, or both. Raw oximetry data can include digitized photodetector measurement values. The processed oximetry date can include oxygen saturation values, percentage of oxygenated hemoglobin, percentage of non-oxygenated hemoglobin, absorption coefficient, scattering coefficient, other information, or any combination of this information.

Figure 12B:
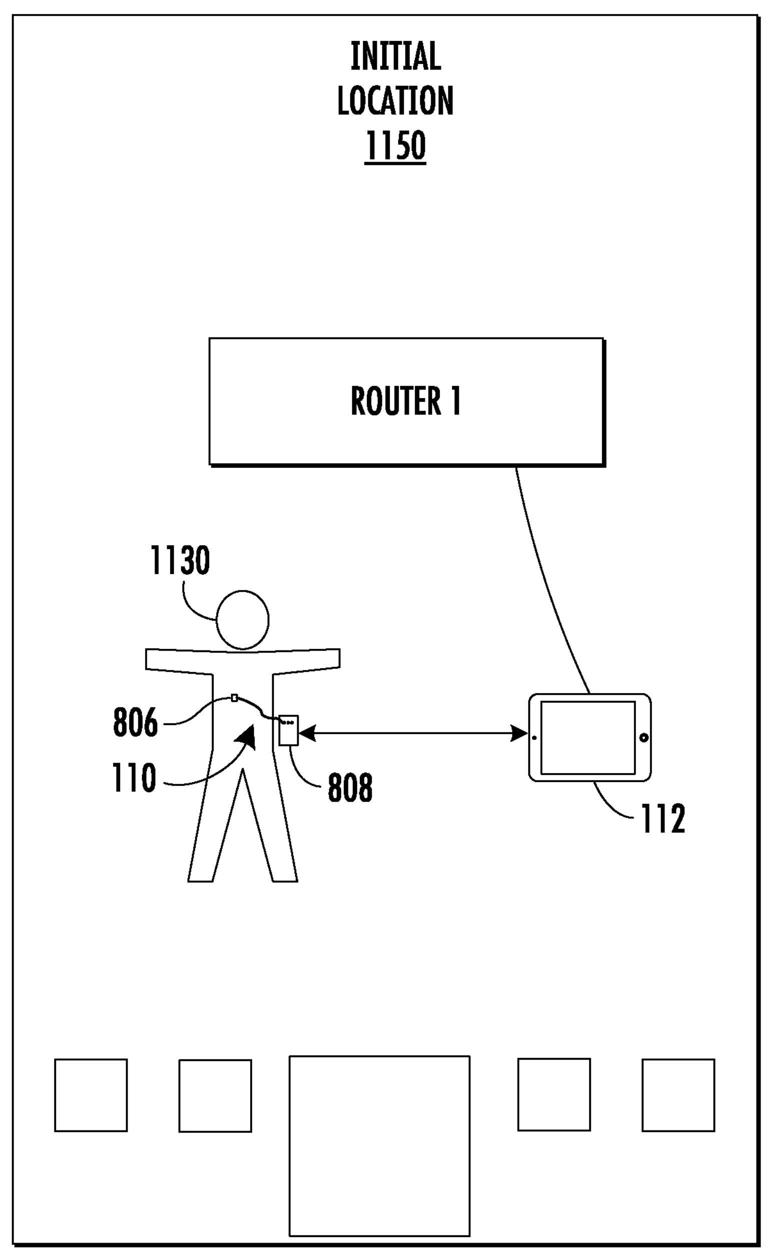
FIG. 12B shows a patient and an oximeter device attached to the patient located at an initial location prior to travel to a subsequent location, in an implementation.

FIG. 12B shows the initial location 1150, in an implementation. At the initial location oximeter device 110 can be connected to a medical device console 112. The oximeter device can be wirelessly or wire connected to the medical device console. For example, the oximeter device can be connected to the medical device console via a RF communication link operating according to one or more RF communication protocols, such as the Bluetooth protocol.

The medical device console 112 can be connected to a router 1 that is located at the initial location and the router can be connected to the network. As such, the oximeter device is connected to the network and the server system via the medical device console and the router.

The medical device console can be connected to the network and server system via a mobile network 127, such as a cellular network, in an embodiment where the medical device console is configured for mobile communication. As such, the oximeter device is connected to the network and the server system via the medical device console and the mobile network. The oximeter device can include a processor, mobile communication circuitry, and operate a mobile device operating system (OS) that enables the oximeter device for mobile communications. The mobile device OS can be Android OS of Google LLC, iOS of Apple Inc., HarmonyOS of Huawei Corporation, KaiOS of Kai Technology, LLC, or other mobile operating systems.

During transport from the initial location to the subsequent location, the oximeter device can continue to generate oximetry information for the patient's tissue. In an implementation where the oximeter device is configured for mobile communication, the oximeter device can transmit the generated oximetry information to the network and server system via the mobile network.

In an implementation where the medical device console travels with the patient during transport from the initial location to the subsequent location, the oximeter device can transmit generated oximetry information to the medical device console. The medical device console can transmit the generated oximetry information to the network and server system, where the medical device console is configured for mobile communication. The medical device console can also be configured to communicate with another mobile device that travels with the oximeter device and the medical device console for transmission to the network and server system. The medical device console can store the generated oximetry information in the memory of the device console. At the subsequent location, the medical device console can transmit the oximetry information to the network and server system when the medical device console connects to the network. Transfer of the oximetry information to the network and server system is described further below.

In an implementation, the oximeter device stores generated oximetry information in the sensor probe memory during transport from the initial location to the second location. The oximeter device can include sufficient memory to store generated oximetry information for one hour or longer during transport. The oximeter device can connect to a device (e.g., a router, a medical device consol, a mobile communication device, a computer, or other device) at the subsequent location where the oximeter device can transmit the stored oximetry information to the device for further transmission to the network and server system. Connection of the oximeter device to a device at the subsequent location is described below.

Figure 12C:
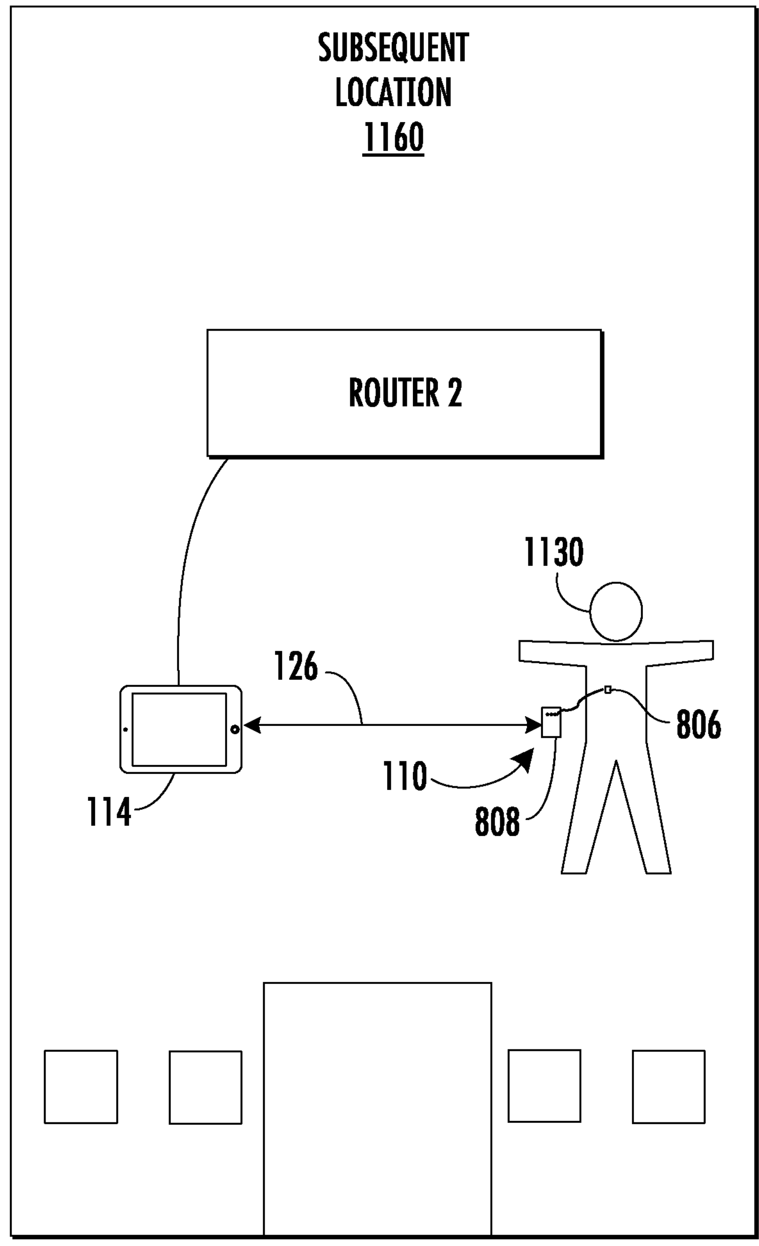
FIG. 12C shows a patient and an oximeter device attached to the patient located at a location subsequent to travel from an initial location, in an implementation.

FIG. 12C shows the patient 1130 and oximeter device 110 located at the subsequent location 1162 subsequent to travel from the initial location 1150. At the subsequent location, a medical device console 114 is connected to router 2 that is located at the subsequent location. The oximeter device 110 can connect to the medical device console via a wired or wireless connection. The wireless connection can be an RF connection, such as a Bluetooth connection. The medical device console 114, oximeter device 110, or both can store and operate program code that pair the oximeter device and the medical device console when these devices are moved into RF communication range. Alternatively, the medical device console 114 and the oximeter device 110 can be paired via user inputs to place the devices in pairing mode.

Subsequent to the medical device console and oximeter device pairing, the oximeter device can transmit any stored oximetry measurement information that is stored during travel to the medical device console. The oximetry measurement information can include raw oximetry measurement information that is not processed by the oximeter device during travel. By not processing the raw oximetry measurement information during travel, the battery power of the battery can be conserved. The medical device console can process the raw oximetry measurement information to generate oximetry information, such as values for oxygen saturation, percentage of oxygenated hemoglobin, percentage of non-oxygenated hemoglobin, absorption coefficients ua, scattering coefficients us, or other oximetry values. The medical device console can display the oximetry information as shown in FIG. 9 and described above.

In an implementation, the medical device console transmits the raw oximetry measurement information to the server system. The server system can process the raw oximetry measurement information to generate oximetry information, such as values for oxygen saturation, percentage of oxygenated hemoglobin, percentage of non-oxygenated hemoglobin, absorption coefficients ua, scattering coefficients us, or other oximetry values. The sever system can transmit the processed or partially processed oximetry measurement information through network 104 back to the medical device console for display as shown in FIG. 9 and described above.

The oximetry measurement information can be processed by the oximeter device and transmitted from the oximeter device to the medical device console, in an implementation. The processed oximetry measurement information can include oximetry information, such as values for oxygen saturation, percentage of oxygenated hemoglobin, percentage of non-oxygenated hemoglobin, absorption coefficients ua, scattering coefficients us, or other oximetry values. The medical device console can display the oximetry information as shown in FIG. 9 and described above.

The oximeter device can continue to make oximetry measurements of the patient tissue at the subsequent location. The oximeter device can process the raw oximetry measurement information for the oximetry measurements, partially process raw oximetry measurement information for the oximetry measurements, or not process the raw oximetry measurement information for the oximetry measurements. Raw oximetry measurement information, partially processed raw oximetry measurement information, processed raw oximetry measurement information can be provided to the medical device console for further processing, display, transmission to the server system, or a combination of these processes.

Figure 12D:
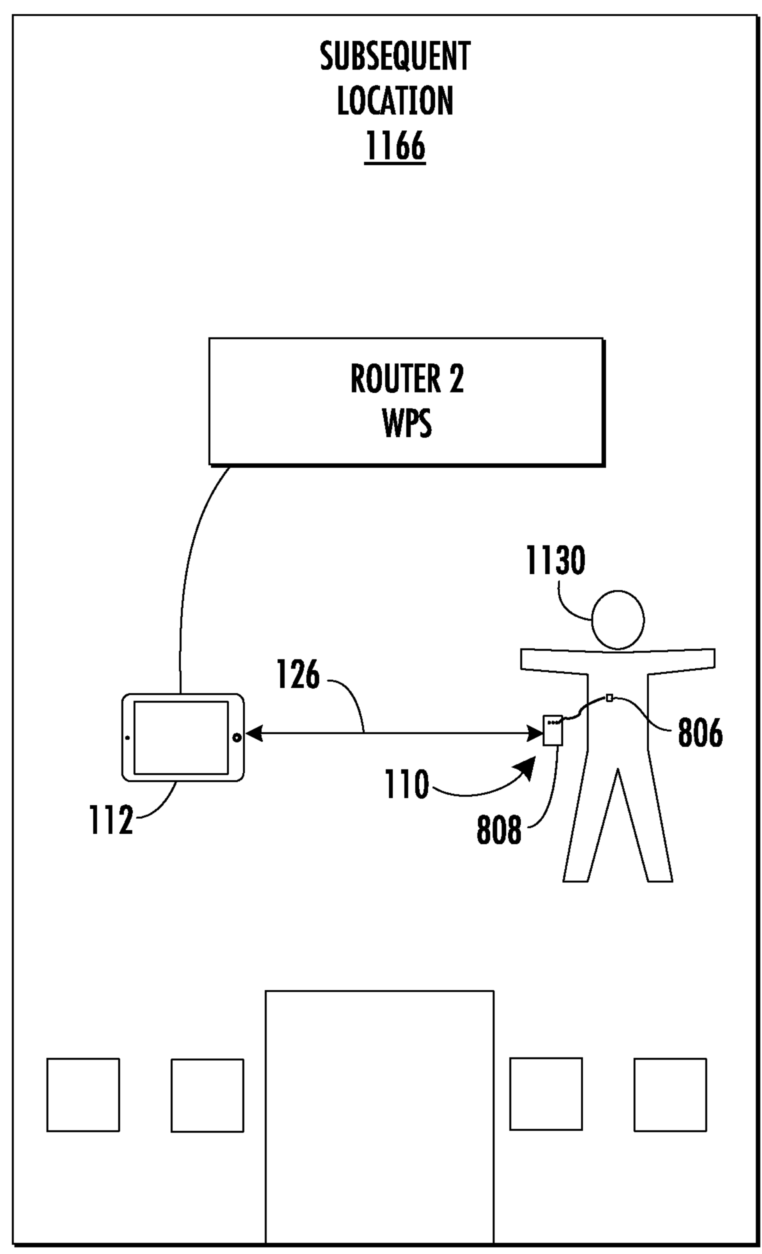
FIG. 12D shows a patient and an oximeter device attached to the patient located at a location subsequent to travel from an initial location, in an implementation.

FIG. 12D shows the patient 1130 and oximeter device 110 located at the subsequent location 1162 subsequent to travel from the initial location 1150. At the subsequent location, a medical device console 114 is connected to router 2 that is located at the subsequent location. In an implementation, router 2 includes a Wi-Fi protected setup (WPS) so that the medical device console can log in and connect with the router without entry of log in credentials on the console by a user typing in the credentials. The WPS feature can include a button or other device that can be pressed to allow log in of the medical device console into the router.

Figure 12E:
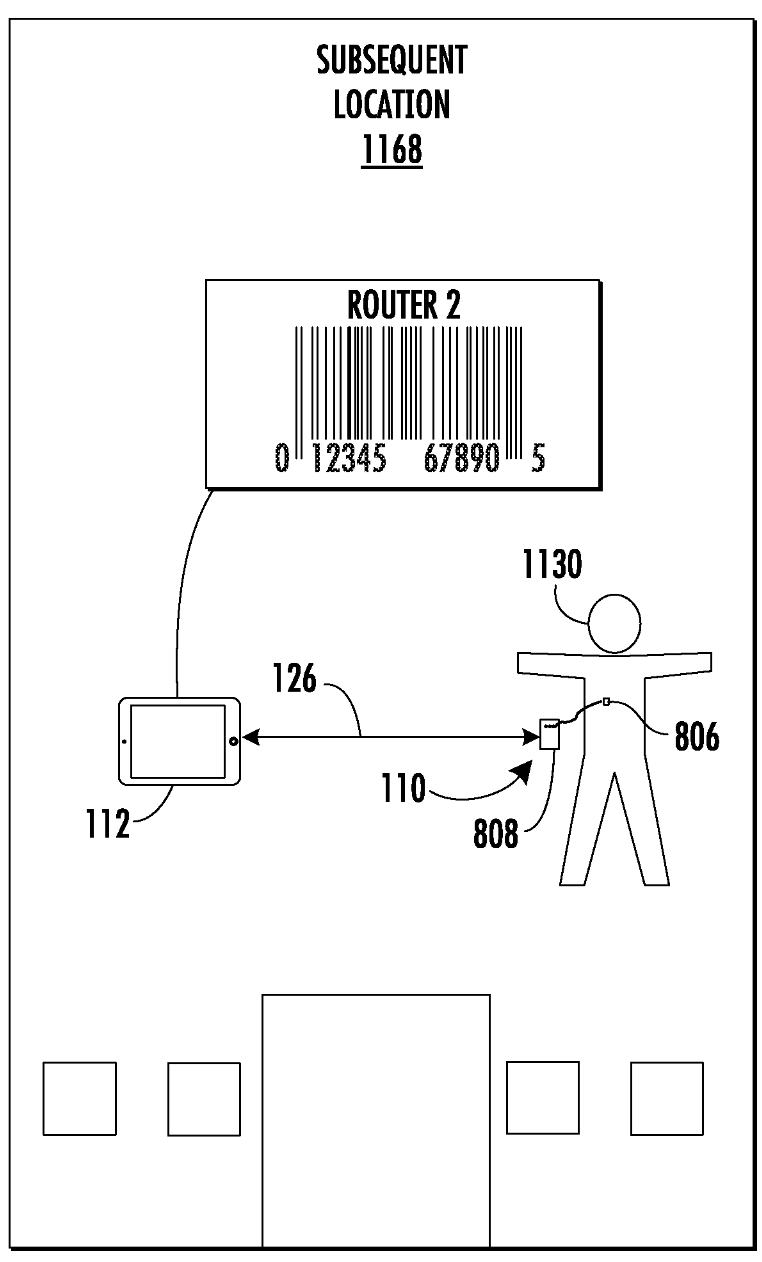
FIG. 12E shows a patient and an oximeter device attached to the patient located at a location subsequent to travel from an initial location, in an implementation.

FIG. 12E shows the patient 1130 and oximeter device 110 located at the subsequent location 1162 subsequent to travel from the initial location 1150. At the subsequent location, a medical device console 114 is connected to router 2 that is located at the subsequent location. In an implementation, router 2 includes a barcode, such as a one-dimensional or two-dimensional bar code that include log in credential for the router. In an implementation, the medical device console using a camera of the console can scan the bar code and supply the credential back to the router to log in to the router. The barcode allows the medical device console to log in and connect with the router without the entry of log in credentials on the console by a user typing in the credentials.

Figure 12F:
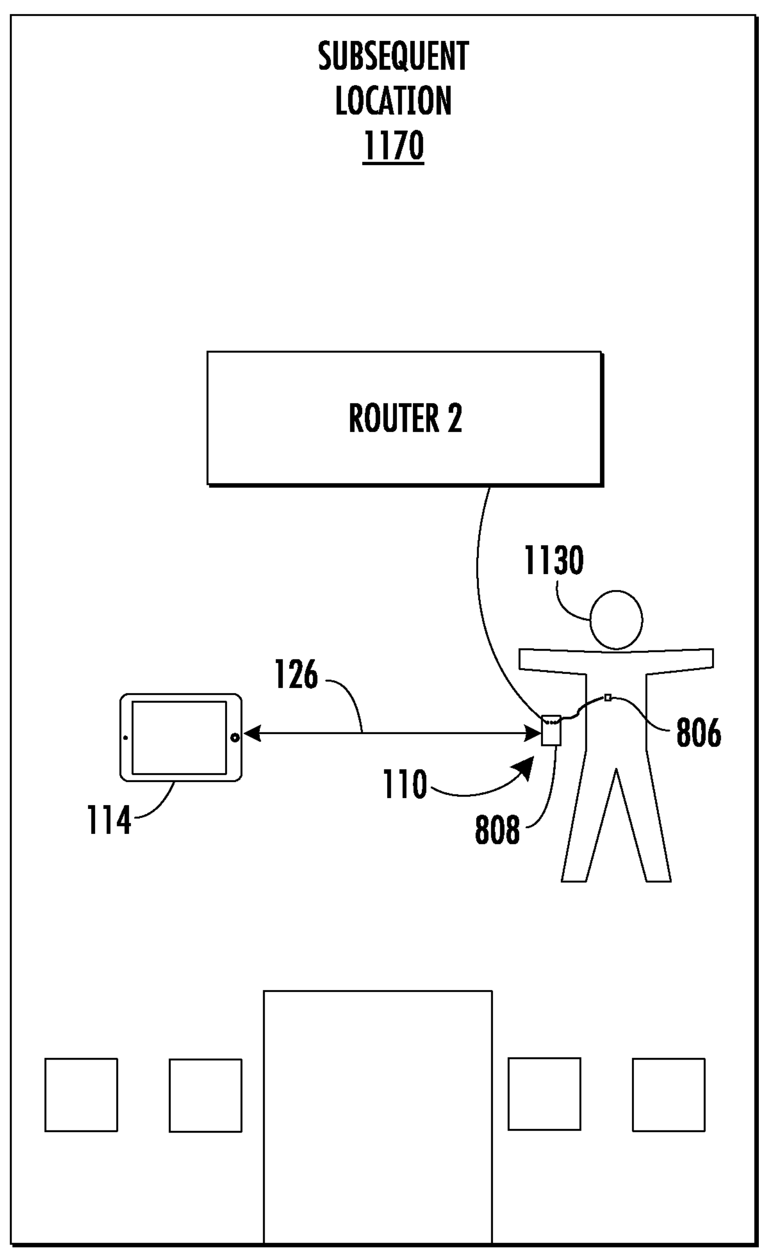
FIG. 12F shows a patient and an oximeter device attached to the patient located at a location subsequent to travel from an initial location, in an implementation.

FIG. 12F shows the patient 1130 and oximeter device 110 located at the subsequent location 1162 subsequent to travel from the initial location 1150. At the subsequent location, the oximeter device 110 can log in and connect to the router. After log in, the oximeter device can transmit raw oximetry measurement information, partially processed raw oximetry measurement information, processed raw oximetry measurement information to the server system via the router and network. The sever system can transmit the processed oximetry measurement information through network 104 back to the medical device console for display, as shown in FIG. 9 and described above. The server system can store the oximetry information for remote access by medial personal as shown in FIG. 12H and described below. The oximeter device can log in and connect with the router via any of the processes described, such as typing in log in credentials into the oximeter device, using a WPS feature, scanning a barcode, or other log in processes.

Figure 12G:
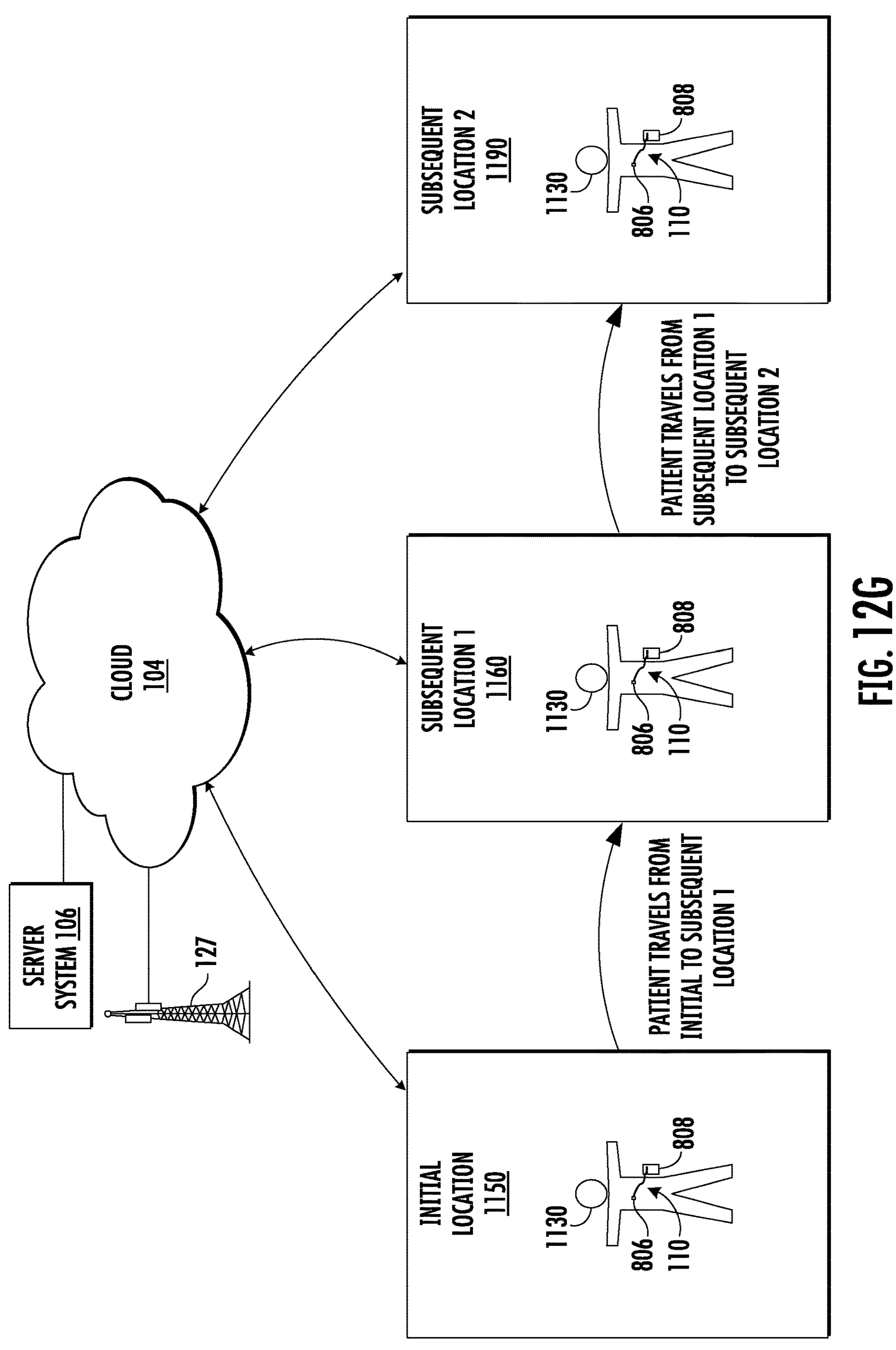
FIG. 12G shows a patient and an oximeter device attached to the patient located at a number of locations subsequent to travel from an initial location, in an implementation.
Figure 12H:
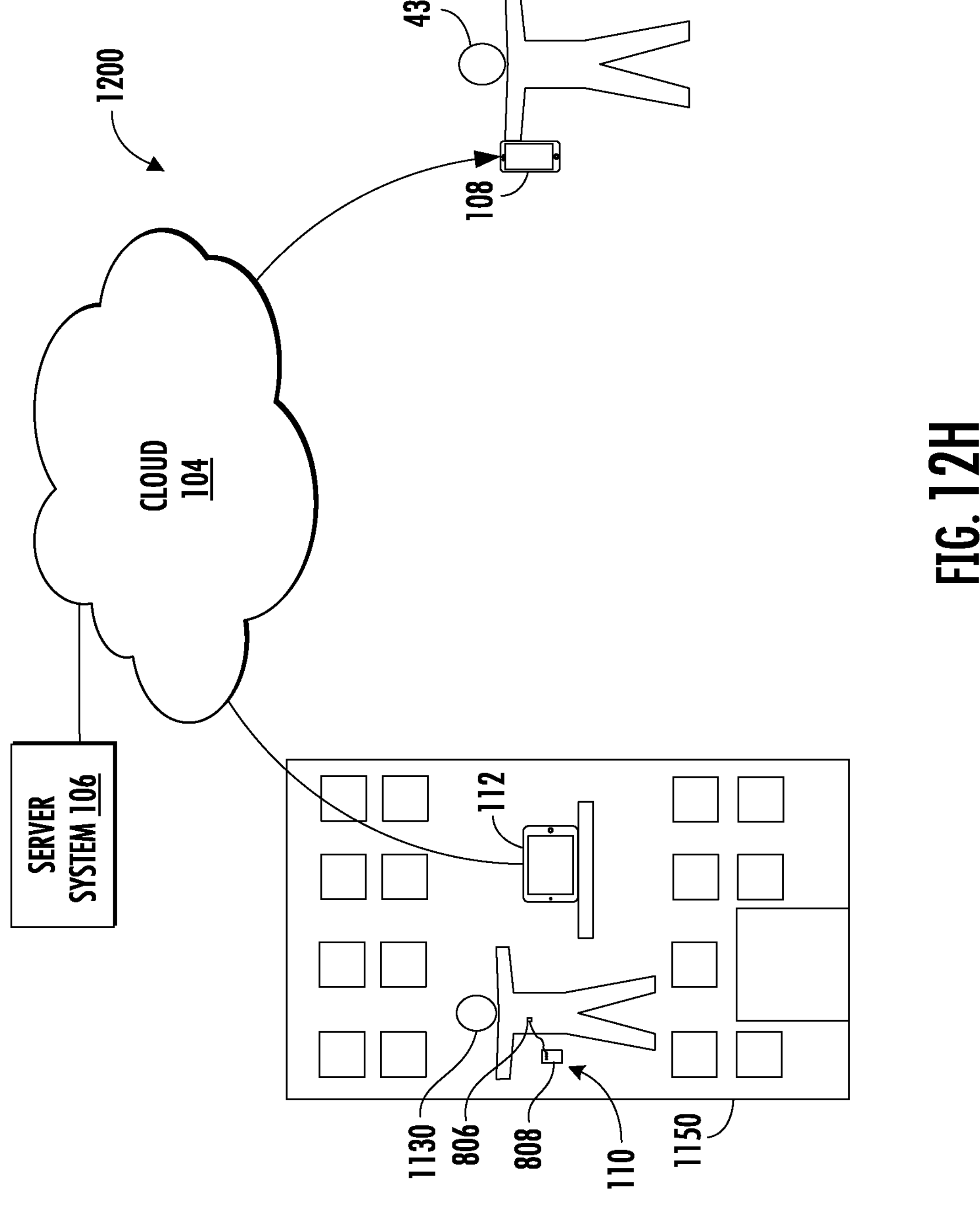
FIG. 12H shows a use environment for the medical communication system shown in FIG. 1.

FIG. 12G shows a number of locations that the patient can travel to while connected to the oximeter device for substantially continuous monitoring by the oximeter device at the various locations and while in transmit. For example, the patient 1130 can travel from an initial location 1150, such as a hospital, to a first subsequent location 1160, such as a rehabilitation facility, and to a second subsequent location 1190, such as the patient's home. The handoffs in connection of the oximeter device to one or more medical device consoles, the network, and the server system can proceed as described above. The patient can travel back to previously visited locations, such as the hospital, with the oximeter device attached and taking oximetry measurements. The oximeter device can connect to a medical device console at the previous location as described above, can connect to a router and the network, to a mobile network, or other device providing access to the network and the server system. The patient can also travel to other locations with the oximeter device attached and taking oximetry measurements for transfer of oximetry measurement data to the network, server system, a medical device console, the mobile network, or another device for transfer of oximetry measurement information to the console, network, and server system.

In an implementation, the user system 108 can establish a peer-to-peer connection and communication with the oximeter device 110 or medical device console 112 located at each of the above described locations, such as before the patient and oximeter device travel, during patient and oximeter device travel, after patient and oximeter device travel, or any combination of these locations and travels.

In an implementation, the mobile device console 112 or the oximeter device 110 is configured to search for an alternative network if communication with a currently connected network is lost. For example, the application operating on the mobile device console 112 can monitor the network connectivity of the console to a currently connected network, such as a Wi-Fi network. If the application operating on the mobile device console determines that the connection to the Wi-Fi network is lost, the application may control the mobile communication circuitry of the console to search for an available mobile network for connection to the mobile network if the mobile network is available. The oximeter device 110 may be similarly configured. Providing for the mobile device console or the oximeter device to find an alternative network allows these devices to continue to transmit oximetry measurement information to the server system 106 for storage and use so that there are minimal or no gaps in the oximetry measurement data generated by the oximeter device and stored on the system server.

FIG. 12H shows a use environment 1200 for the medical communication system 100 shown in FIG. 1 and described above. In the use environment shown in FIG. 12A, a patient 1130 is located in a medical facility 1150, such as a hospital, rehabilitation center, or another medical office. Alternatively, the patient can be at the patient's home, in a vehicle, or at another location. In an implementation, an oximeter device 110 is attached to patient tissue of patient 1130 to collect oximetry information for the patient tissue. Specifically, a sensor probe unit 806 of an oximeter device 110 may be connected to patient tissue, such as a patient's breast tissue before, during, and after a surgery has been performed, such as a breast reconstruction surgery. The oximeter device 110 may generate oximetry information for the patient tissue.

The sensor probe electronic module 808 of the oximeter device 110 is wirelessly connected to a medical device console 112 and may transmit the oximetry information to the medical device console for display or for further transmission to other devices and systems. The medical device console may be connected to a router at the location of the patient, such as at a medical facility, the patient's home, or another location. The medical device console may send oximetry information to server system 106 or client system 108 via network 104.

In the use environment, the oximetry information is transmitted up to the cloud 104 (e.g., Internet, intranet, or other network elements described above) from the medical device console, such as by a Wi-Fi connection, a mobile device connection (such as a mobile cellular connection), or other connection. In an implementation, where the oximeter device 110 is Wi-Fi enabled, mobile communication enabled (such as a mobile cellular connection), the oximetry information is transmitted up to the cloud 104. The oximetry information may be transmitted through the cloud to the server system 106, which stores the oximetry information. The oximetry information can be stored in a database in the server system. The database can have a variety of database types, such as in a relational database, such as an SQL database.

The oximetry information may be retrieved from the server system 106 by a client system 108. The oximetry information can be requested or pushed to the client system and can be delivered to the client system via a Wi-Fi connection, a mobile connection, or another type of connection provided by the cloud or local networks.

The client system can store and operate a medical device application that provides for the display of the oximetry information on the display of the client system. The oximetry information can be displayed on the client system, the same or similarly to the oximetry information displayed on the medical device console, as shown in FIGS. 9 and 10.

The client system 108 can be located and used at a variety of locations, such at the home of a medical professional, in a car of a medical professional such as while the medical professional drives to the medical facility, or a variety of other locations that medical professional might be located at. In an implementation, the client system 108 is adapted to store the oximetry information and any other information transmitted with the oximetry information, such as quality metric information and any time stamps for the oximeter information and quality metric information.

The client system 108 allows the medical profession, such as a doctor, to assess the patient's health while the doctor is away from the medical facility to monitor the patient's health before or after a medical procedure, while the patient is in recovery. For example, the doctor can contact other medical professionals at the medical facility to direct treatment for the patient based on the oximetry information displayed on the client system.

More specifically, in an implementation, the medical device console may communicate with the local router (e.g., router at medical facility, home, or other location), network 104, server system 106, client system 108 (e.g., in a peer-to-peer communication), or any combination of these devices and systems via a secure file transfer protocol (SFTP) in an implementation. If the patient's location is a medical facility, such as a hospital, for example, transmission from the medical device console may pass through TCP port 22 of the local network's firewall (e.g., medical device facility's firewall) to network 104 using the secure shell (SSH) protocol.

In an implementation, in a peer-to-peer communication, an application operating on client system 108 can request oximetry measurement information from the medical device console 112 when the medical device console is operating an application that allows access to the oximetry measurement information stored on the console. A peer-to-peer communication may be available between the medical device console and the client system when the patient and console are at a patient's home, recovery center, vehicle, or other location where transmission security may be lower than at a hospital, for example. The medical device console and client system can recognize each other through standard peer-to-peer recognition protocols and via security features of the applications operating on the medical device console and client system. In an implementation, a user of the client system can be a medical care provider of the patient, such as the patient's doctor. Via the client system, the doctor can monitor the patient's oxygen saturation values, such as after a surgery, such as a breast reconstruction surgery. In an implementation, the application operating on the medical device console can send push notifications to the client system, such as if the patient's oxygen saturation level falls below a threshold oxygen saturation level. In an implementation where the oximeter device 110 is a Wi-Fi enabled device, the oximeter device and client system can communicate via peer-to-peer communications as described.

In an implementation, the medical device console communicates through the local router (e.g., router at medical facility) and across network 104 to server system 106 using SSL/TSL encryption for communication and secure file transfer of oximetry measurement information. The medical device console can make a REST API call (also known as a REST API request) for outbound communication via the TCP 443 port of the medical device facility's firewall to server system 106 using SSL/TSL encryption for communication. The medical device facility will determine whether to allow outbound communication through TCP 443 port. When the TCP 443 port is opened, the oximeter device 110 can securely transfer oximetry measurement information to server system 106 for storage and by the server system. Subsequent to storage of the oximetry information on the server system, the client device can access the oximetry information stored on the server system.

Figure 13:
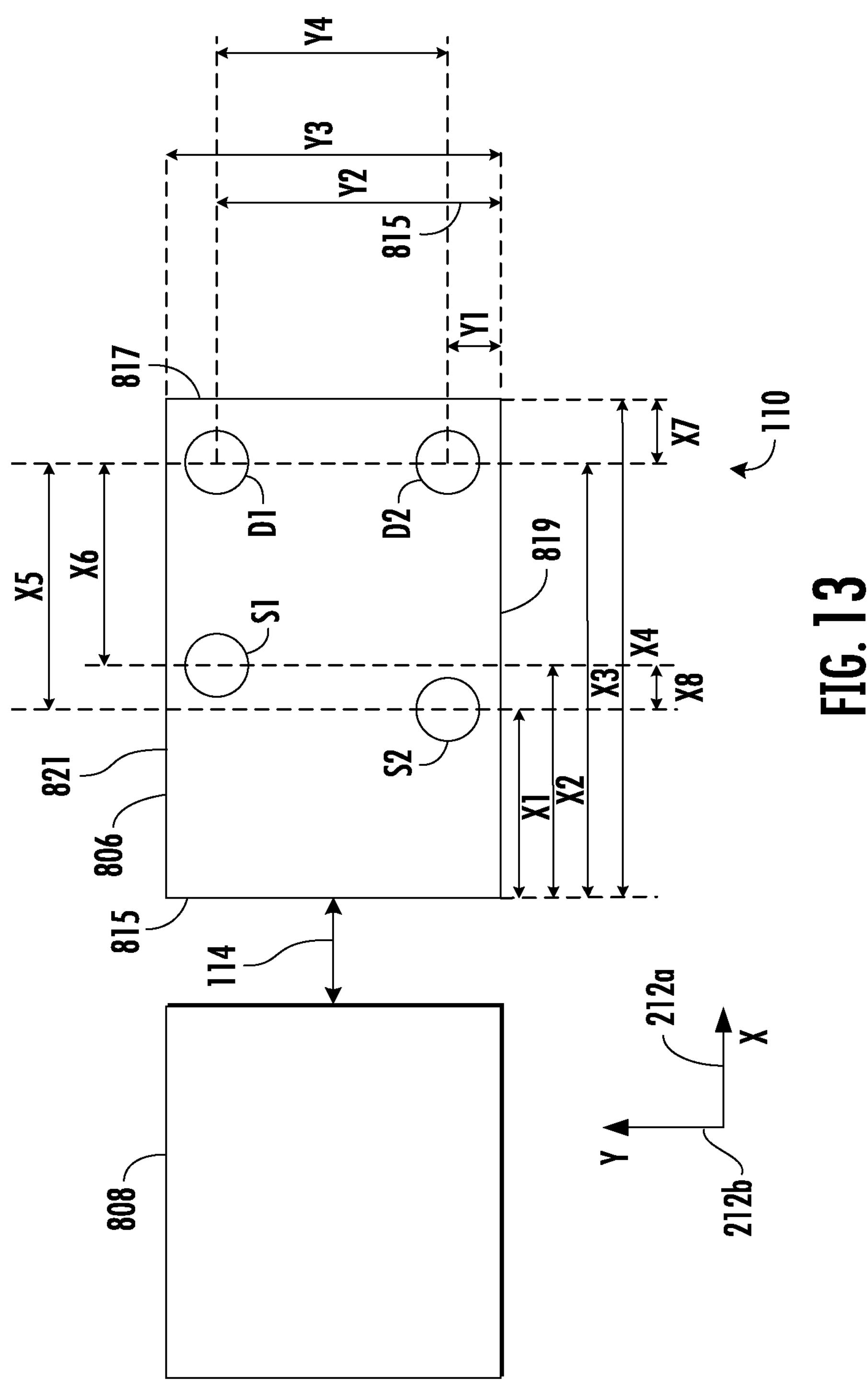
FIG. 13 shows a simplified schematic of the sensor probe, in an implementation.
Figure 17:
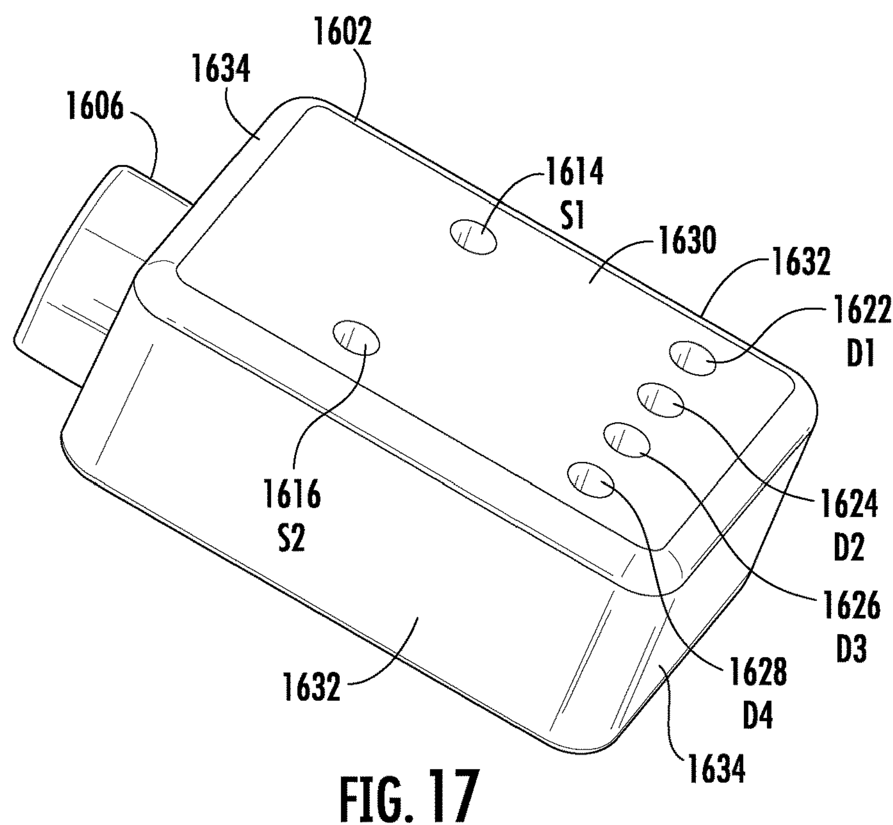
FIG. 17 shows a perspective bottom view of the sensor probe unit, in an implementation.

FIG. 13 shows a simplified schematic of oximeter device 110, in an implementation, and includes a number of identifiers for a number of lengths between various elements of the sensor probe unit 806. FIG. 13 includes a coordinate axis where the X axis 212*a* extends right and left along the plane of the drawing page and the Y axis 212*b* extends upward and downward along the plane of the drawing page.

x1 is the length between a backside 815 of the sensor probe unit 806 and the center of a second source structure S2.

x2 is the length between the backside 815 of the sensor probe unit and the center of a first source structure S1.

x3 is the length between the backside 815 of the oximeter device unit and the centers of each of the detector structures D1 and D2, where the centers are arranged in a line. A line between the centers of the first and second source structures S1 and S2, and the line between the centers of the detector structures D1 and D2 are not parallel, in this implementation. The line between the centers of the first and second source structures S1 and S2, and the line between the centers of the detector structures D1, D2, D3, and D4 are not collinear, in this implementation. The line between the centers of the first and second source structures S1 and S2, and the line between the centers of the detector structures D1, D2, D3, and D4 can be lines on the planar bottom surface of housing 1602 (FIG. 17).

x4 is the length between a front side 817 and a backside 815 of the sensor probe unit.

x5 is the length between the center of the second source structure S2 and the centers of the detector structures D1 and D2, where the centers are arranged in a line.

x6 is the length between the center of the first source structure S1 and the line through the centers of the detector structures D1 and D2.

x7 is the length between the line through the centers of the detector structures D1 and D2 and a front side 817 of the sensor probe unit.

x8 is the length between the line through the centers of the source structures S1 and S2.

y1 is the length between a side 819 of the sensor probe unit and the center of the second detector structure D2.

y2 is the length between the side 819 of the sensor probe unit and the center of the first detector structure D1.

Y3 is the length between the sides 819 and 821 of the sensor probe unit.

Y4 is the length between the centers of the first and second detector structures D1 and D2.

Table 5 below includes the lengths.

| Length Identifier | Length |
|---|---|
| x1 | 5.44 millimeters (0.214 inches) |
| x2 | 5.94 millimeters (0.234 inches) |
| x3 | 10.95 millimeters (0.431 inches) |
| x4 | 12.46 millimeters (0.49 inches) |
| x5 | 5.51 millimeters (0.217 inches) |
| x6 | 5.00 millimeters (0.197 inches) |
| x7 | 1.50 millimeters (0.059 inches) |
| x8 | 0.510 millimeters (0.020 inches) |
| y1 | 1.80 millimeters (0.071 inches) |
| y2 | 6.81 millimeters (0.268 inches) |
| y3 | 8.64 millimeters (0.340 inches) |
| y4 | 5.00 millimeters (0.197 inches) |

Figure 14:
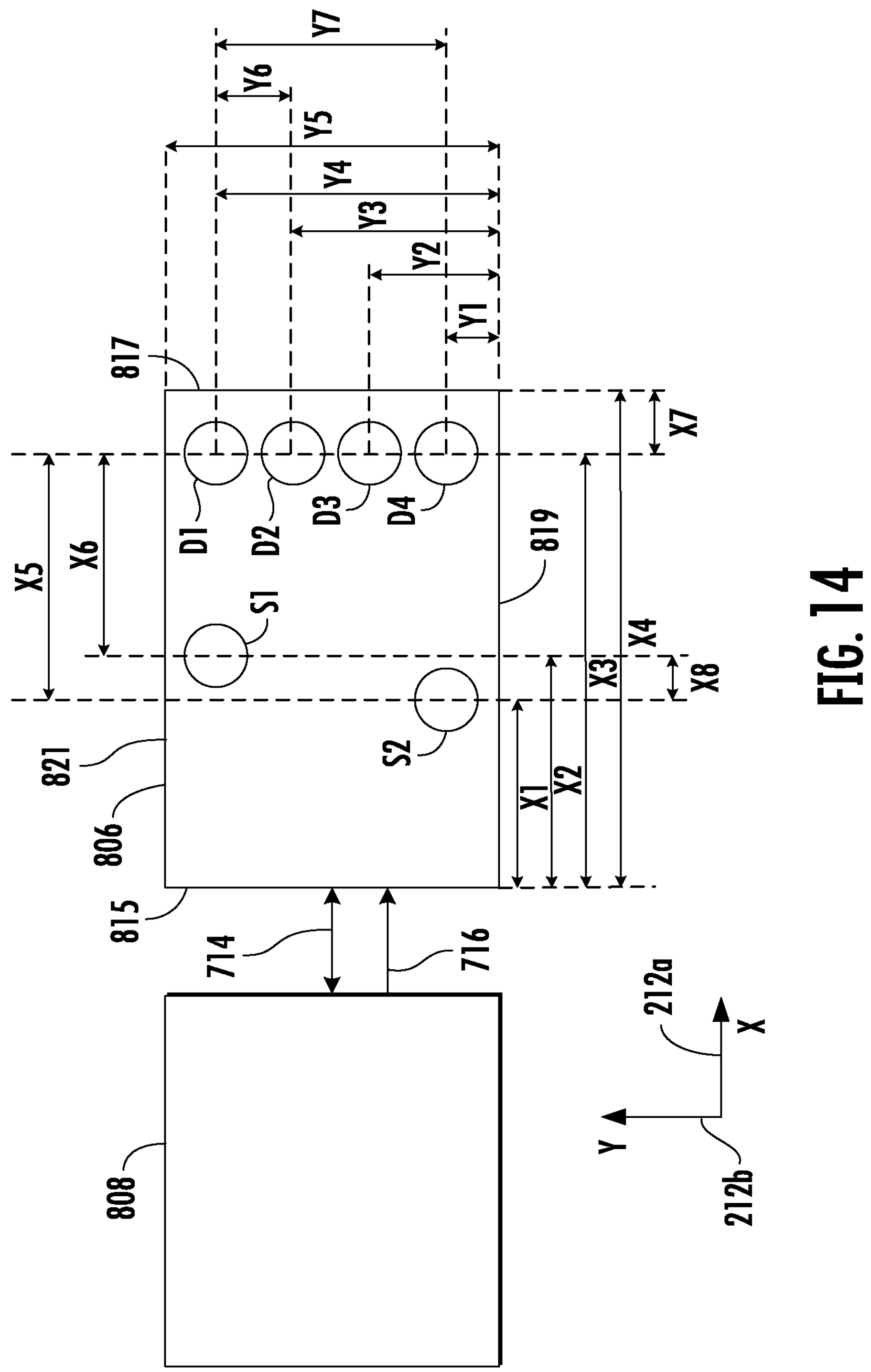
FIG. 14 shows a simplified schematic of the sensor probe, in an implementation.

FIG. 14 shows a simplified schematic of oximeter device 110, in an implementation, and includes a number of identifiers for a number of lengths between various elements of the sensor probe unit 806. FIG. 14 includes a coordinate axis where the X axis 212*a* extends right and left along the plane of the drawing page and the Y axis 212*b* extends upward and downward along the plane of the drawing page.

x1 is the length between a backside 815 of the sensor probe unit 806 and the center of a second source structure S2.

x2 is the length between the backside 815 of the sensor probe unit and the center of a first source structure S1.

x3 is the length between the backside 815 of the sensor probe unit and the centers of each of the detector structures D1, D2, D3, and D4, where the centers are in a line. A line between the centers of the first and second source structures S1 and S2 and the line between the centers of the detector structures D1, D2, D3, and D4 are not parallel, in this implementation. The line between the centers of the first and second source structures S1 and S2, and the line between the centers of the detector structures D1, D2, D3, and D4 are not collinear, in this implementation. The line between the centers of the first and second source structures S1 and S2, and the line between the centers of the detector structures D1, D2, D3, and D4 can be lines on the planar bottom surface of housing 1602 (FIG. 17).

x4 is the length between the front side 817 and the backside 815 of the sensor probe unit.

x5 is the length between the center of the second source structure S2 and the line through the centers of the detector structures D1, D2, D3, and D4.

x6 is the length between the center of the first source structure S1 and the line through the centers of the detector structures D1, D2, D3, and D4.

x7 is the length between the line through the centers of the detector structures D1, D2, D3, and D4 and a front side 817 of the sensor probe unit 806.

x8 is the length between the line through the centers of the source structures S1 and S2.

y1 is the length between a side 819 of the sensor probe unit and the center of the fourth detector structure D4.

y2 is the length between the side 819 of the sensor probe unit and the center of the third detector structure D3.

y3 is the length between the side 819 of the sensor probe unit and the center of the second source structure D2.

y4 is the length between the side 819 of the sensor probe unit and the center of the first source structure SD1.

y5 is the length between the sides 819 and 821 of the sensor probe unit.

y6 is the length between the centers of the first and second detector structures D1 and D2. Y6 can be the length between each immediately adjacent pair of detector structures.

y7 is the length between the centers of the first and fourth detector structures D1 and D4.

Table 6 below includes the lengths.

| Length Identifier | Length |
|---|---|
| x1 | 5.44 millimeters (0.214 inches) |
| x2 | 5.94 millimeters (0.234 inches) |
| x3 | 10.95 millimeters (0.431 inches) |
| x4 | 12.45 millimeters (0.49 inches) |
| x5 | 5.51 millimeters (0.217 inches) |
| x6 | 5.00 millimeters (0.197 inches) |
| x7 | 1.50 millimeters (0.059 inches) |
| x8 | 0.51 millimeters (0.020 inches) |
| y1 | 1.80 millimeters (0.071 inches) |
| y2 | 3.48 millimeters (0.137 inches) |
| y3 | 5.13 millimeters (0.202 inches) |
| y4 | 6.81 millimeters (0.268 inches) |
| y5 | 8.64 millimeters (0.340 inches) |
| y6 | 1.68 millimeters (0.066 inches) |
| y7 | 5.00 millimeters (0.197 inches) |

Figure 15:
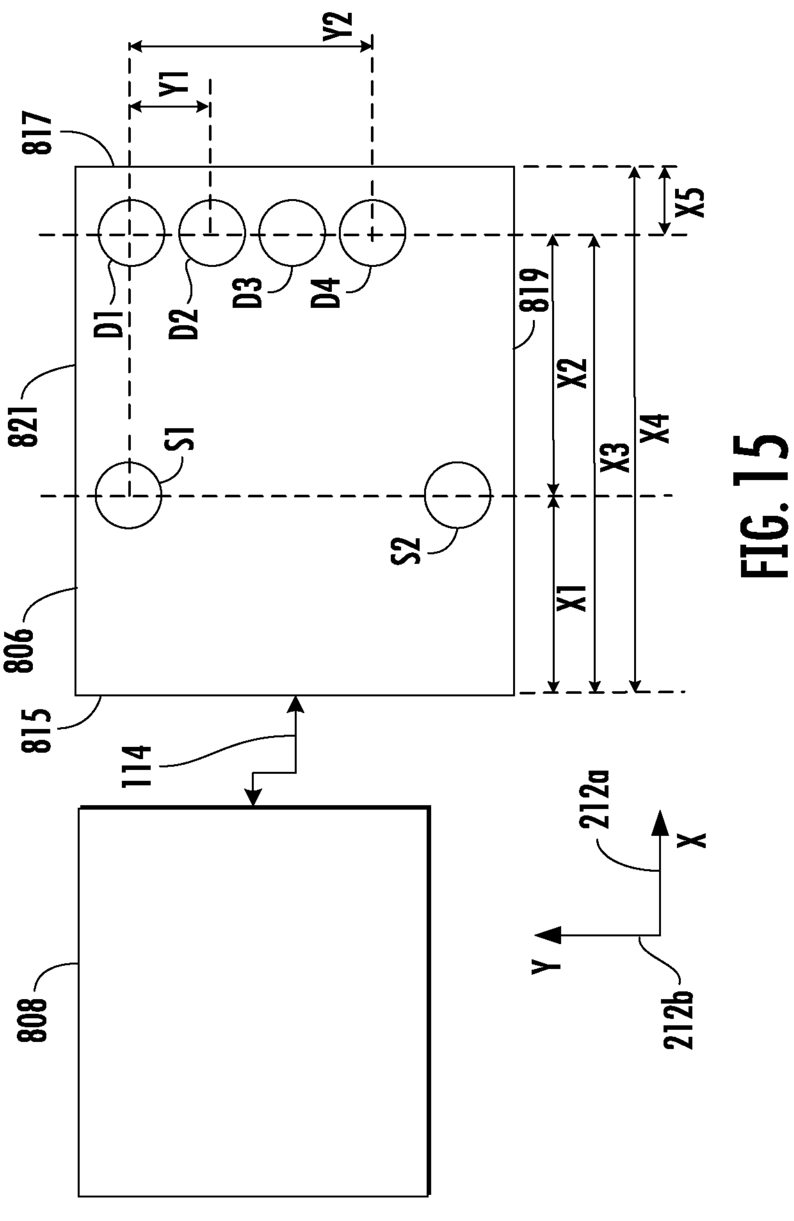
FIG. 15 shows a simplified schematic of a sensor probe, in an implementation

FIG. 15 shows a simplified schematic of oximeter device 110, in an implementation, and includes a number of identifiers for a number of lengths between various elements of the sensor probe unit 806. FIG. 15 includes a coordinate axis where the X axis 212*a* extends right and left along the plane of the drawing page and the Y axis 212*b* extends upward and downward along the plane of the drawing page.

x1 is the length between a backside 815 of the sensor probe unit 806 and the centers of the first and second source structures S1 and S2, where the centers are arranged in a line.

x2 is the length between a line passing between the centers of the first and second source structures S1 and S2, and between a line passing through the centers of the first, second, third, and fourth detector structures D1, D2, D3, and D4.

x3 is the length between the backside 815 of the sensor probe unit and the centers of each of the detector structures D1, D2, D3, and D4, where the centers are arranged in a line.

x4 is the length between the front side 817 and the backside 815 of the sensor probe unit.

x5 is the length between the line through the centers of the detector structures D1, D2, D3, and D4 and a front side 817 of the sensor probe unit 806.

y1 is the length between the centers of the first and second detector structures D1 and D2. y1 can be the length between each immediately adjacent pair of detector structures.

y2 is the length between the centers of the first and fourth detector structures D1 and D4.

Table 7 below includes the lengths.

| Length Identifier | Length |
|---|---|
| x1 | 5.44 millimeters (0.214 inches) |
| x2 | 5.51 millimeters (0.217 inches) |
| | or |
| | 5.00 millimeters (0.197 inches) |
| x3 | 10.95 millimeters (0.431 inches) |
| x4 | 12.45 millimeters (0.49 inches) |
| x5 | 1.50 millimeters (0.059 inches) |
| y1 | 1.68 millimeters (0.066 inches) |
| y2 | 5.00 millimeters (0.197 inches) |

Figure 16:
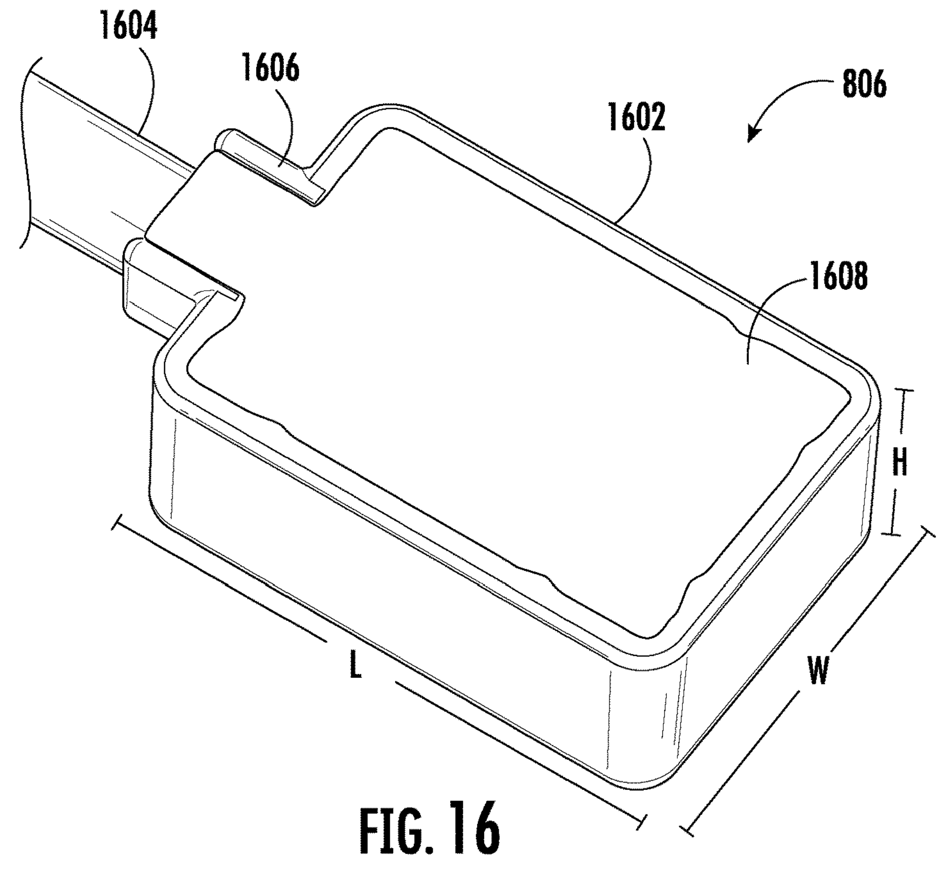
FIG. 16 shows a perspective top view of the sensor probe unit, in an implementation.

The arrangements of source structures S1 and S2 and detector structures D1, D2, D3, and D4 shown in each of FIGS. 14-16 can be arranged as mirror images of the arrangements shown and described, in various implementations. For example, the arrangements of source structures S1 and S2 and detector structures D1, D2, D3, and D4 shown in FIGS. 14-16 can each be a vertical mirror image of the arrangements, a horizontal mirror image of the arrangements, or a vertical and horizontal mirror image of the arrangements, in various implementations. Further, the sensor head may have an arrangement that is a mirror image of that shown in FIGS. 13-15, such as left and right mirror images.

In implementation of each of the configurations shown in FIGS. 13-15, a first distance is between the first source structure S1 and the first detector structure D1, a second distance is between the first source structure S1 and the second detector structure D2, a third distance is between the second source structure S2 and the first detector structure D1, and a fourth distance is between the second source structure S2 and the second detector structure D2, and the first, second, third, and fourth distances are different from each other.

In an implementation of each of the configurations shown in FIGS. 13-15 between the first source structure S1 and the first detector structure D1, there are no intervening source or detector structures. Between the first source structure S1 and the second detector structure D2, D3, or D4, there are no intervening source or detector structures. Between the second source structure S2 and the first detector structure D1, there are no intervening source or detector structures. And, between the second source structure and the second detector structure D2, D3, or D4, there are no intervening source or detector structures.

In an implementation, on a line between the first source structure S1 and the first detector structure D1, there are no intervening source or detector structures. On a line between the first source structure S1 and the second detector structure D2, D3, or D4, there are no intervening source or detector structures. On a line between the second source structure S2 and the first detector structure D1, there are no intervening source or detector structures. On a line between the second source structure and the second detector structure D2, D3, or D4, there are no intervening source or detector structures.

In an implementation, there are at least three waveguides generated and emitted by the sensor probe unit 806 with either two sources and one detector or two detectors and one source in the sensor probe unit.

The measurements, for example, in millimeters or centimeters, are approximate values. The values can vary due to, for example, measurement or manufacturing tolerances (as will be understood by those of ordinary skill in the art) or other factors (as will be further understood by those of ordinary skill in the art). A measurement can vary, for example, by plus or minus 1 percent, plus or minus 5 percent, plus or minus 10 percent, plus or minus 15 percent, plus or minus 20 percent, plus or minus 1 to 5 percent, plus or minus 5 to 10 percent, or plus or minus 15 to 20 percent. Further, the measurements are for a specific implementation of the device, and other implementations can have different values, such as certain measurements, dimensions, or both made longer to accommodate smaller hands or larger hands or to access tissue in a particular location of a patient's body.

For the specific implementations described, some specific values, ranges of values, and numbers are provided. These values indicate, for example, dimension, angles, ranges, frequencies, wavelengths, numbers, a relationship (e.g., relative value), and other quantities (e.g., numbers of sensors, sources, detectors, diodes, fiber optic cables, and so forth). Some measurements are for a specific implementation of the device, and other implementations can have different values, such as certain dimensions made larger for a larger-sized product, or smaller for a smaller-sized product. The device may be made proportionally larger or smaller by adjusting relative measurements proportionally (e.g., maintaining the same or about the same ratio between different measurements). In various implementations, the values (or numbers or quantities) can be the same as the value given, about the same of the value given, at least or greater than the value given, or can be at most or less than the value given, or any combination of these. The values (or numbers or quantities) can also be within a range of any two values given or a range including the two values given. When a range is given, the range can also include any number within that range to any other number within that range.

The dimensions, for example, along an axis, a rotational orientation, or both are approximate values. The dimensions can be in values, directions, angles, or any combination of these dimensions. Dimensions, for example, of values in millimeters or centimeters, of directions along an axis or at an angular orientation relative to an axis, of an angular orientation are approximate values. The values, direction, and angles can vary due to, for example, measurement or manufacturing tolerances or other factors. A dimension can vary, for example, by plus or minus 0.1 percent, plus or minus 0.2 percent, plus or minus 0.5 percent, plus or minus 1 percent, plus or minus 5 percent, plus or minus 10 percent, plus or minus 15 percent, plus or minus 20 percent, plus or minus 0.1 to 0.2 percent, plus or minus 0.2 to 0.5 percent, plus or minus 0.5 to 1 percent, plus or minus 1 to 5 percent, plus or minus 5 to 10 percent, plus or minus 10 to 15 percent, or plus or minus 15 to 20 percent.

The shapes, for example, a geometric shape can be approximate shapes. The shapes can be in values, directions, angles, terms, or any combination of these shapes. The shapes can vary due to, for example, measurement or manufacturing tolerances or other factors. A shape can vary, for example, by plus or minus 0.1 percent, plus or minus 0.2 percent, plus or minus 0.5 percent, plus or minus 1 percent, plus or minus 5 percent, plus or minus 10 percent, plus or minus 15 percent, plus or minus 20 percent, plus or minus 0.1 to 0.2 percent, plus or minus 0.2 to 0.5 percent, plus or minus 0.5 to 1 percent, plus or minus 1 to 5 percent, plus or minus 5 to 10 percent, plus or minus 10 to 15 percent, or plus or minus 15 to 20 percent.

The orientations, for example, parallel, perpendicular, transverse, and angle are approximate values. The orientation can be in values, directions, angles, terms, or any combination of these orientations. Orientations, for example, of terms or angles can be approximate orientations. The orientations vary due to, for example, measurement or manufacturing tolerances or other factors. An orientation can vary, for example, by plus or minus 0.1 percent, plus or minus 0.2 percent, plus or minus 0.5 percent, plus or minus 1 percent, plus or minus 5 percent, plus or minus 10 percent, plus or minus 15 percent, or plus or minus 20 percent. Terms, such as about, substantially, approximately, or other relative terms can include the described ranges as will be readily understood by those of ordinary skill in the art and can include ranges that will be understood by those of ordinary skill in the art.

FIG. 16 shows a perspective top view of the sensor probe unit 806, in an implementation. The sensor probe unit includes a housing 1602 (sometimes referred to as a case or an enclosure, such as a first enclosure). The housing can have a generally rectangular-shaped top, bottom, and sides. A length L of the housing can be from about 8 millimeters to about 21 millimeters (e.g., about 12.5 millimeters). A width W of the housing can be from about 5 millimeters to about 13 millimeters (e.g., about 9 millimeters). A height H of the housing can be from about 2 millimeters to about 7 millimeters (e.g., about 5 millimeters). The housing can include a housing extension portion 1606. The housing can be formed of a plastic-type material. The plastic-type material forming the housing can be black and opaque to inhibit light from entering the sensor probe unit through the plastic-type material and to inhibit light from being transmitted from the sensor probe unit through the plastic-type material.

An electrical cable 1604 is coupled to the housing via the housing extension 1606. The housing extension can include internal structures, such as teeth that grip an outer housing of the electrical cable to provide strain relief. The electrical cable can include wires for a communication link and a power supply connection. The housing includes an interior space that is filled with a potting material 1606, such as epoxy resin.

FIG. 17 shows a perspective bottom view of the sensor probe unit 806, in an implementation. The housing includes a bottom 1630. The bottom can be a planar surface. The bottom includes a first aperture 1614 formed in the bottom, a second aperture 1616 formed in the bottom, a third aperture 1622 formed in the bottom, a fourth aperture 1624 formed in the bottom, a fifth aperture 1626 formed in the bottom, and a sixth aperture 1628 formed in the bottom. Each of the apertures extends from a first side of the bottom (e.g., outward-facing side of the bottom) to a second side of the bottom (e.g., an inward-facing side of the bottom at the interior space of the housing). The first and second apertures are arranged in a first line. The third, fourth, fifth, and sixth apertures are arranged in a second line that is not parallel and not colinear with the first line.

In an implementation, there are no apertures between the first and second source apertures configured to emit light or detect light. In an implementation, between the first aperture and the third aperture, there are no intervening apertures, configured to emit light or detect light. In an implementation, between the first aperture and the fourth aperture, there are no intervening apertures, configured to emit light or detect light. In an implementation, between the first aperture and the fifth aperture, there are no intervening apertures, configured to emit light or detect light. In an implementation, between the first aperture and the sixth aperture, there are no intervening apertures, configured to emit light or detect light.

In an implementation, between the second aperture and the third aperture, there are no intervening apertures, configured to emit light or detect light. In an implementation, between the second aperture and the fourth aperture, there are no intervening apertures, configured to emit light or detect light. In an implementation, between the second aperture and the fifth aperture, there are no intervening apertures, configured to emit light or detect light. In an implementation, between the second aperture and the sixth aperture, there are no intervening apertures, configured to emit light or detect light.

In an implementation, each of the apertures has a circular cross-section. In an implementation, the first aperture forms a beam combiner for the first and second LEDs 2304 and 2306 housed in the housing of the sensor probe unit 806. In an implementation, the second aperture forms a beam combiner for the third and fourth LEDs 2308 and 2310 housed in the housing of the sensor probe unit 806. Each of the apertures can include a waveguide (such as an optical fiber) located in each aperture.

Each aperture is filled with a window material that is substantially clear to the wavelengths of light generated by the light engine (e.g., 690 nanometers and 830 nanometers). Each window includes a first surface inside of housing 1608 and a second surface outside of housing 1608 at the bottom of the housing, having a planar surface and the second surfaces are planar with the plane of the bottom of housing 1608. The window material can be a polymer material, a plastic-type material, glass, a waveguide (e.g., an optical fiber), or another material that are clear to the wavelengths of light generated by the light engine.

In an implementation, the sensor probe unit 806 is a sealed unit that inhibits liquid and debris from entering the unit. More specifically, the potting material 1608 seals the opening of the housing and seals the housing extension 1606 around where a portion of electrical cable 1604 is located in the extension. Further, the windows are located in the apertures that seal the apertures on the bottom of the housing. Sealing the sensor probe unit from liquid (e.g., patient bodily fluid or other fluids) and debris entry prevents a patient from being electrically shocked by the sensor probe unit when the unit is attached to the patient's tissue, such as when fluid from an open wound is present or fluids used in a medical procedure are present.

Each aperture of the bottom and the window located in the aperture form at least a portion of a source structure or detector structure. Specifically, the first aperture 1614 and the window located in this aperture form at least a portion of the first source structure S1. The second aperture 1616 and the window located in this aperture form at least a portion of the second source structure S2. The third aperture 1622 and the window located in this aperture form at least a portion of the first detector structure D1. The fourth aperture 1624 and the window located in this aperture form at least a portion of the second detector structure D2. The fifth aperture 1626 and the window located in this aperture form at least a portion of the third detector structure D3. The sixth aperture 1628 and the window located in this aperture form at least a portion of the fourth detector structure D4.

Each window can have an approximate rod shape with ends that are round (e.g., circular) or that have other shapes (e.g., square). The end of the window can have substantially equal diameters (e.g., 1 millimeter) or the diameters can vary by relatively small lengths.

The edges of the sidewalls 1632 and 1634, where the sidewalls are joined to the back 1630, are rounded. The round shapes enhance the comfort of the sensor probe electronic module 808 when the bottom of the unit is placed on a patient's skin. The edges of the housing where the sidewalls meet can also be rounded.

Figure 18:
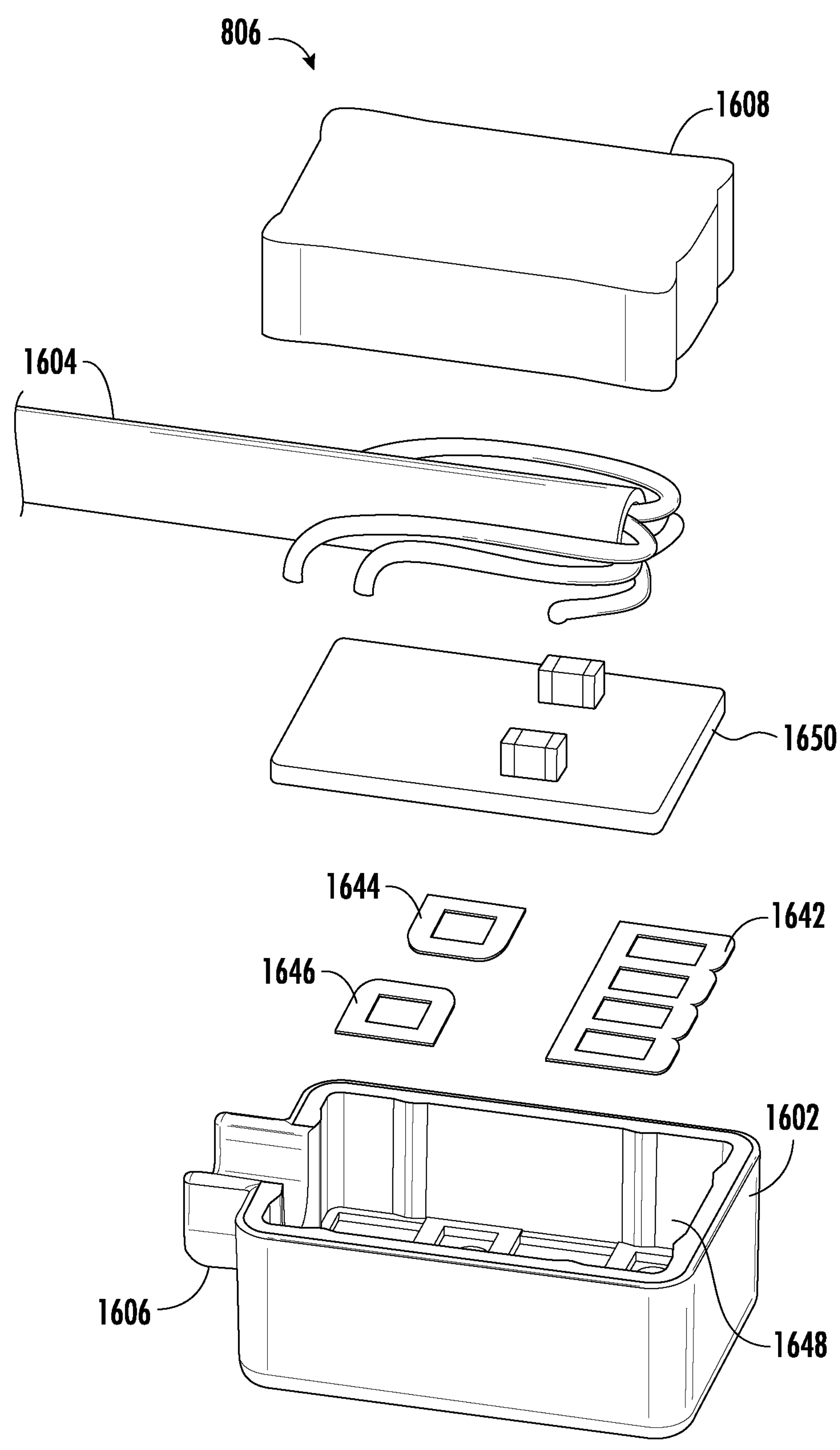
FIG. 18 shows an exploded view of the sensor probe unit, in an implantation.

FIG. 18 shows an exploded view of the sensor probe unit 806, in an implantation. The sensor probe unit further includes a printed circuit board (PCB) 1650 that is configured to fit inside the opening 1648 of housing 1602. The probe unit includes a first seal 1642, a second seal 1644, and a third seal 1646 that fit inside the opening of the housing. The seals seal portions of the bottom surface of the PCB to portions of the housing that are located in the housing opening. The seals are black and opaque. Where the seals seal portions of the PCB to the housing, the seals inhibit light from entering the sealed portions.

Figure 19:
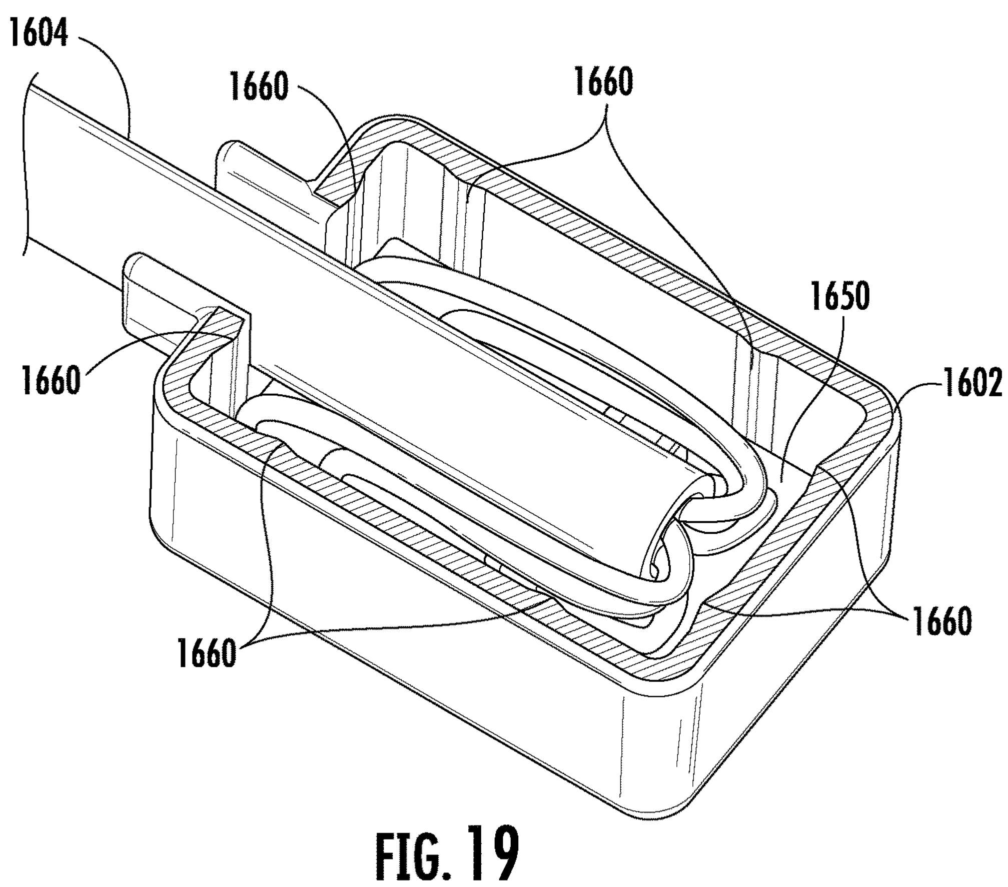
FIG. 19 shows the PCB and cable located in the opening of the sensor probe unit.

FIG. 19 shows the PCB and electrical cable located in the opening of the opening 1648 of the housing 1602. Each sidewall 1632 and 1634 of the housing 1602 includes an outer surface and an inner surface. Each inner surface of each sidewall includes one or more extensions 1660 (e.g., two extensions per side that extend into the opening 1648 of the housing. Each of the extensions can have equal heights. Sides of the PCB board are configured to contact the extensions when the PCB is located in the opening of the housing. Contact of the sides of the PCB and the extensions fix the lateral position and rotational orientation the PCB in the opening of the housing and with respect to the sidewalls of the housing.

Figure 20:
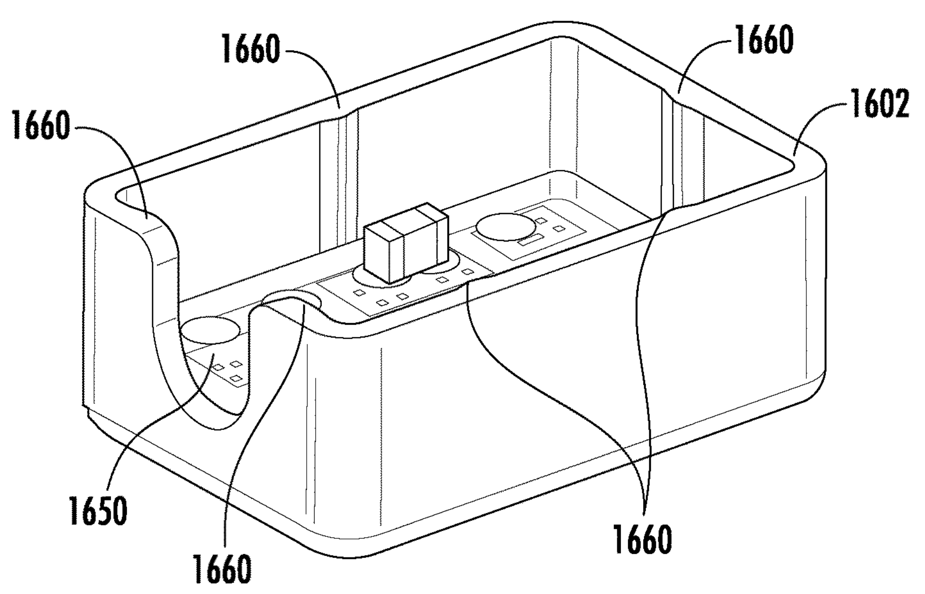
FIG. 20 shows the PCB located in the housing, in an implementation where the sides of the PCB contact the extensions to fix the lateral position and rotational orientation of the PCB in the opening of the housing.

FIG. 20 shows the PCB located in the housing, in an implementation where the sides of the PCB contact the extensions to fix the lateral position and rotational orientation of the PCB in the opening of the housing.

Figure 21:
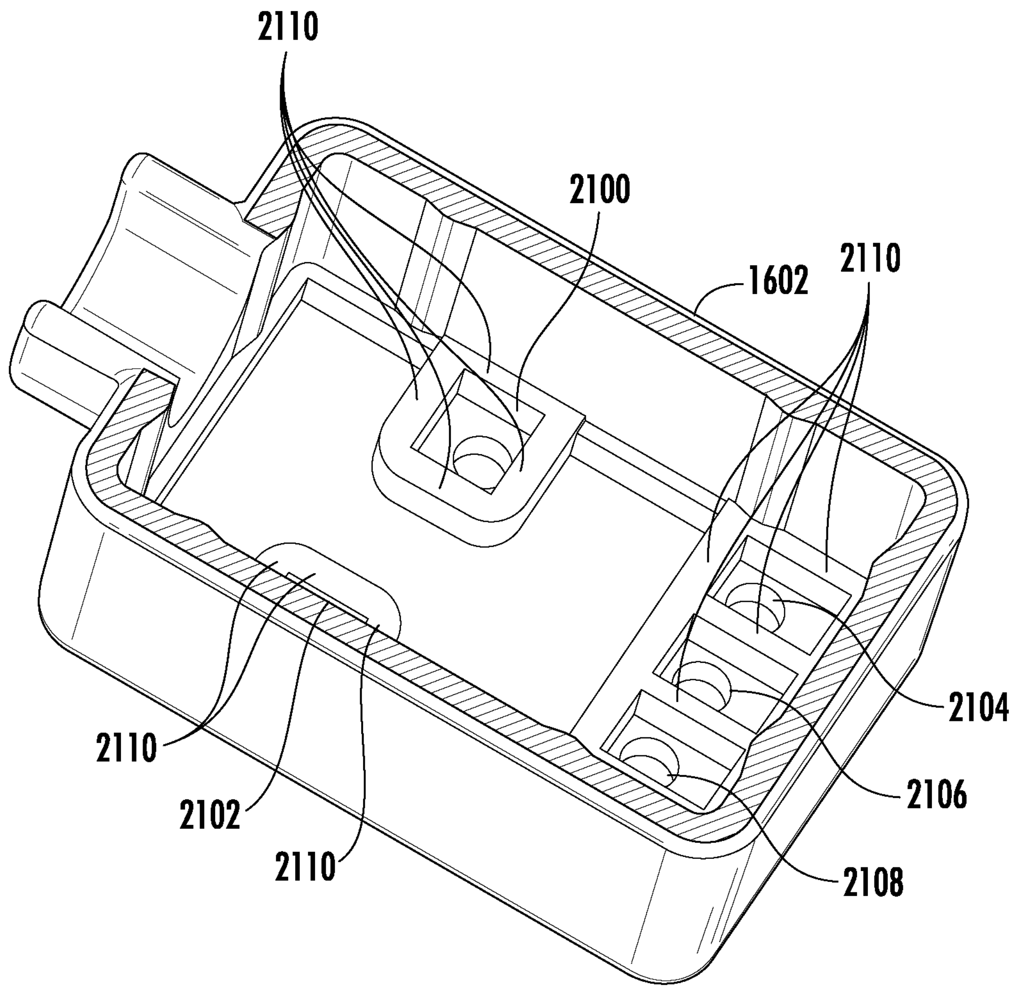
FIG. 21 shows a perspective view of the interior space of the housing.

FIG. 21 shows a perspective view of the interior space of the housing. The bottom of the housing includes a number of wells 2100, 2102, 2104, 2106, 2108, and another well in line with wells 2104, 2106, and 2108 that is not shown in the perspective view. The wells are formed in interior walls 2110 of the housing. The interior space can include six wells. Each well is formed by four surrounding interior walls 2110. In an alternative implementation, the wells are formed in the bottom of the housing where the sidewalls of the wells are the sides of the bottom of the housing. Each aperture formed in the bottom of the housing and each window located in each aperture are positioned at the bottom of the wells, respectively.

Figure 22A:
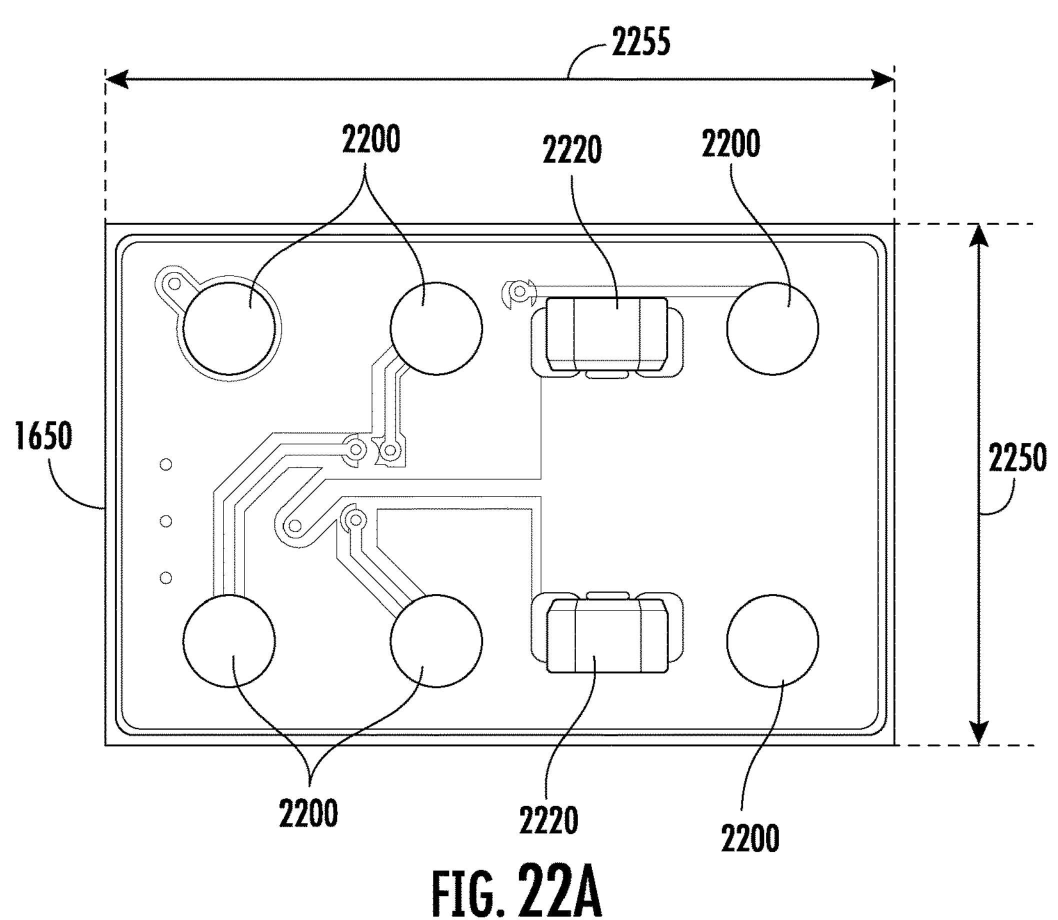
FIG. 22A shows a top view of the PCB, in an implementation.

FIG. 22A shows a top view of the PCB 1650, in an implementation. The top surface of the PCB includes a number of solder pads 2200. The solder pads can be soldered to the wires in electrical cable 1604 as shown in FIG. 19. The top surface of the PCB includes a number of capacitors (e.g., two capacitors). The capacitors can be connected across the power and ground supplied to the PCB from the sensor probe electronic module 808 via electrical cable 1604 to limit fluctuations in the supplied voltage from ground bounce.

The PCB can be from about 4 millimeters to about 10 millimeters wide (e.g., about 7.00 millimeters) 2250 and from about 7 millimeters long to about 15 millimeters (e.g., about 10.80 millimeters) long 2255, in an implementation. The PCB can have other lengths and widths in other implementations. The PCB can be from about 0.4 millimeters to about 7 millimeters (e.g., about 0.58) thick, in an implementation. The printed circuit board assembly (PCBA) with the components on the PCBA can be from about 1.8 millimeters to about 2.4 millimeters (e.g., about 2.13) thick, in an implementation.

The top surface of the PCB includes a number of solder pads 2200. The solder pads can be soldered to the wires in electrical cable 1604 as shown in FIG. 19. The top surface of the PCB includes a number of capacitors (e.g., two capacitors). The capacitors can be connected across the power and ground that are supplied to the PCB from the sensor probe electronic module 808 via electrical cable 1604 to limit fluctuations in the supplied voltage due to ground bounce.

Figure 22B:
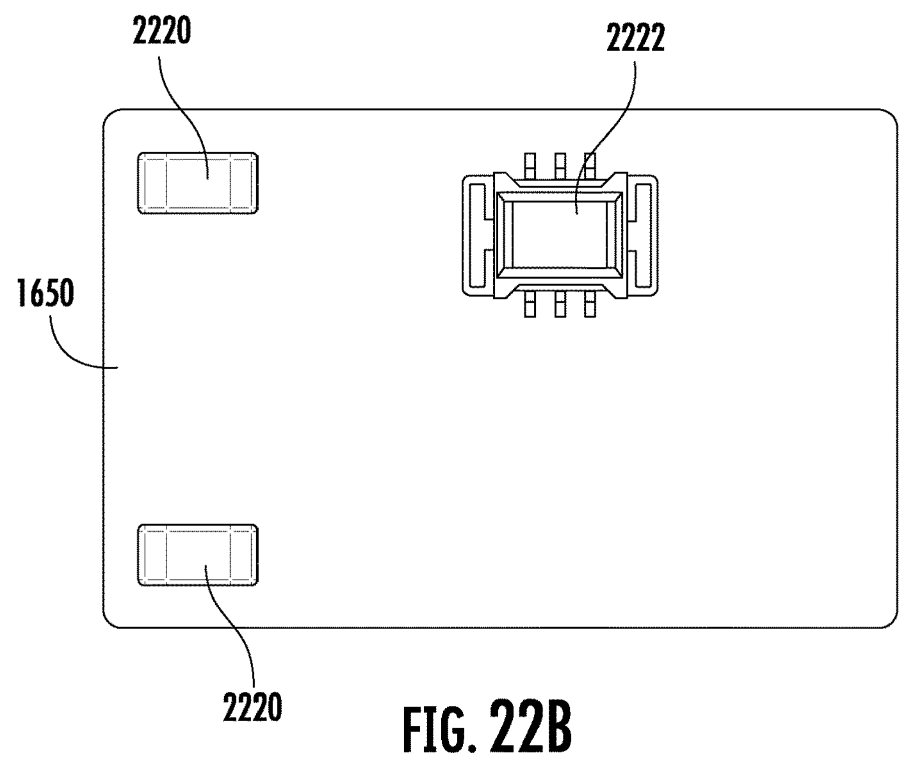
FIG. 22B shows a top view of the PCB 1650, in an implementation.

FIG. 22B shows a top view of the PCB 1650, in an implementation. The implementation of the PCBs shown in FIGS. 22A and 22B are similar. The implementation of PCB 1650, shown in FIG. 22B, includes a mezzanine connector 2222. The mezzanine connector can connect PCB 1650 to another PCB that may be included in the sensor head 806. FIG. 24B shows a sensor head implementation that includes PCB 1650 connected to another PCB, such as a flex PCB 1652 via mezzanine connector 2222. Flex PCB 1652 is described further below.

Figure 23:
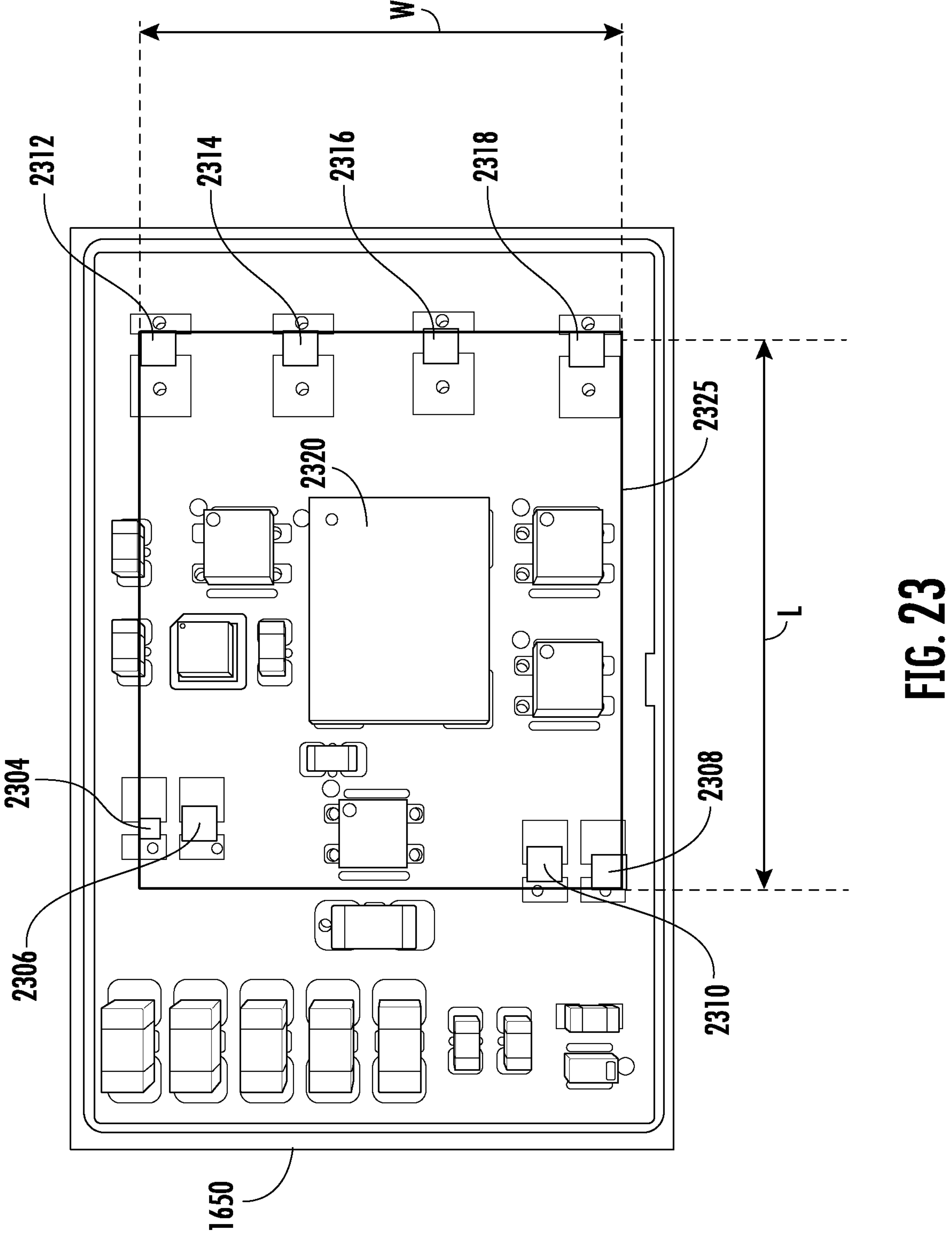
FIG. 23 shows a bottom view of the PCB, in an implementation.

FIG. 23 shows a bottom view of the PCB 1650, in an implementation. The bottom surface of the PCB includes a number of circuits mounted on the surface. The circuits include a first LED 2304, a second LED 2306, a third LED 2308, and a fourth LED 2310. The LEDs form a portion of the light engine. The first LED 2304 and the third LED 2308 generate first wavelengths, such as 830 nanometers. The second LED 2306 and the fourth LED 2310 generate second wavelengths, such as 690 nanometers. The LEDs may be IC dies (e.g., unpackaged dies) that are back ground and bonded to the PCB. The LEDs may be wire bonded to the PCB or include ball grid arrays that are reflowed to connect to the PCB.

The circuits include a first photodetector 2312, a second photodetector 2314, a photodetector LED 2316, and a photodetector LED 2318. The photodetectors may be IC dies (e.g., unpackaged dies) that are back ground and bonded to the PCB. The photodetectors may be wire bonded to the PCB or include ball grid arrays that are reflowed to connect to the PCB. The circuits include an AFE IC 2320.

When the PCB is located in the opening 1648 of housing 1602, the first and second LEDs are located in well 2102, the third and fourth LEDs are located in well 2100, the first photodiode is located in a well not shown in FIG. 21 where the well is directly adjacent to well 2108, the second photodiode is located in well 2108, the third photodiode is located in well 2106, and the fourth photodiode 2318 is located in well 2104.

Seal 1646 seals the PCB to the walls 2110 of well 2102 around the first and second LEDs located in the well so that light emitted from the first and second LEDs exits the aperture and window at the bottom of well 2102 and does not exit the aperture and window at the bottom of well 2100.

Seal 1644 seals the PCB to the walls 2110 of well 2100 around the third and fourth LEDs located in the well so that light emitted from the third and fourth LEDs exits the aperture and window at the bottom of well 2100 and does not exit the aperture and window at the bottom of well 2102.

Seal 1642 seals the PCB to the walls 2110 of wells 2104 where the fourth photodetector 2318 is sealed in the well. Seal 1642 seals the PCB to the walls 2110 of wells 2106 where the third photodetector 2316 is sealed in the well. Seal 1642 seals the PCB to the walls 2110 of wells 2108 where the second photodetector 2314 is sealed in the well. Seal 1642 seals the PCB to the walls 2110 of the wells (not shown associated with first photodetector 2312) where the first photodetector 2312 is sealed in the well.

Seal 1462, the walls 2110 forming the wells for the photodetector, and the PCB provides that light that passes through one of the apertures (e.g., aperture 1622 of D1) and the window in aperture to its associated photodetector (e.g., photodetector 2312) does not pass through any of the other apertures (e.g., aperture 1624 of D2, aperture 1626 of D3, and aperture 1628 of D4) and windows in these apertures to the photodetector (e.g., photodetector 2312). Elimination of these optical crosstalk paths improves the reliability of the oximetry measurements make oximeter device 110.

Each of the seals 1642 1644, and 1646 further prevents light emitted by the first, second, third, and fourth LEDs from reaching the first, second, third, and fourth photodetectors through interior travel in housing 1602. That is, light emitted from the first, second, third, and fourth LEDs travels out through their respective apertures and windows to be reflected from patient tissue (or a tissue analog) to enter the apertures and windows associated with the photodetectors to reach the photodetectors. In some implementations, one or more portions of the PCB is coated with an opaque coating so that light is prevented from being transmitted from the LEDs and through the PCB to the photodetectors. The walls, seals, well, PCB, and PCB opaque coating prevent light crosstalk inside of housing 1602 and provide for increased accuracy of oximetry measurements.

In an implementation, a single LED 2304 generates and emits the first and second wavelengths, where the PCB does not include the LED 2308. Further, a single LED 2308 generates and emits the first and second wavelengths, where the PCB does not include the LED 2310. Seal 1646 seals the PCB to the walls 2110 of well 2102 around the LED 2304 located in the well so that light emitted from the first and second LEDs exits the aperture and window at the bottom of well 2102 and does not exit the aperture and window at the bottom of well 2100. The aperture and window may be under LED 2304. Seal 1644 seals the PCB to the walls 2110 of well 2100 around the LED 2308 located in the well so that light emitted from the third and fourth LEDs exits the aperture and window at the bottom of well 2100 and does not exit the aperture and window at the bottom of well 2102. The aperture and window may be under LED 2308.

In an implementation, a sensor area is a smallest rectangular area 2325 or smallest square area that the LEDs and photodetectors are in. A length L of the area is from about 5.9 millimeters to about 6.3 millimeters (e.g., about 6.14 millimeters) and a width W of the area is from about 5 millimeters to about 5.2 millimeters (e.g., about 5.98 millimeters). The area of the rectangular area is from about 29.5 square millimeters to about 32.8 square millimeters (e.g., about 36.7 square millimeters).

A relatively small tissue flap or skin flap used for tissue reconstruction, such as breast reconstruction, is about 7 millimeters by about 15 millimeters. The sensor area of the sensor probe 806 has a size and shape and size that allows the sensor area to fit over the small tissue flap, such that the oxygen saturation of the entire flap can be measured and monitored.

Figure 24A:
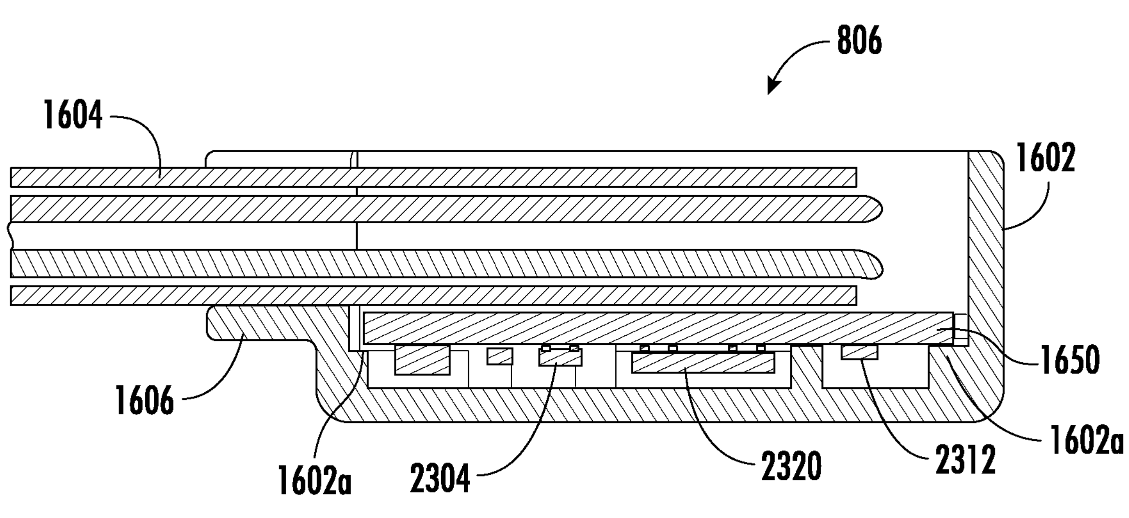
FIG. 24A shows a cross-sectional view of the sensor probe unit (i.e., sensor head), in an implementation.
Figure 24B:
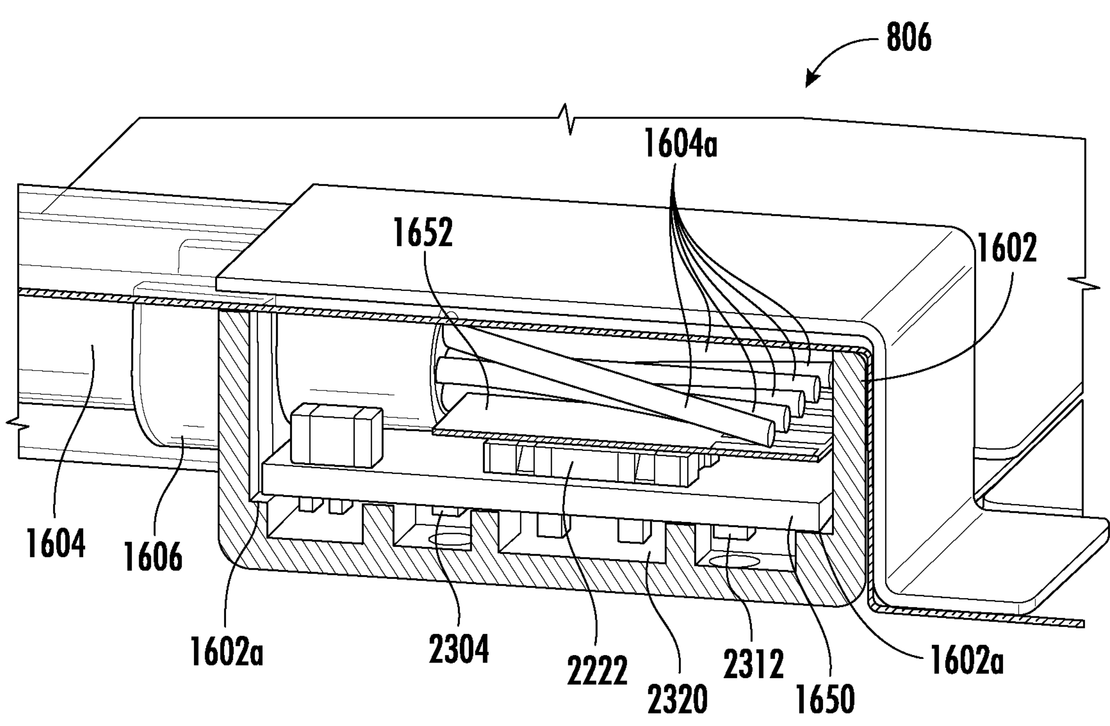
FIG. 24B shows a cross-sectional view of the sensor probe unit (i.e., sensor head), in an implementation.

FIG. 24A shows a cross-sectional view of sensor probe unit 806, in an implementation. The electrical cable 1604 enters housing 1602 through the housing extension portion 1606 of the housing. The electrical cable is above the PCB 1605 and on the opposite side of the PCB from the LEDs, such as LED 2304, AFE IC 2320, the photodetectors, such as photodetector 2312. The wires in electrical cable 1604 extend from the electrical cable housing to attach to the PCB and to the analog frontend circuit. The analog front end circuit is connected between the wires of the electrical cable and the LEDs, in an implementation.

The analog frontend circuit is connected between the wires of the electrical cable and the photodetectors, in an implementation. The connection may be a soldered connection or a mechanical connection.

In an implementation, the PCB is attached to a shelf portion 1602*a* of the housing. The PCB can be adhered to the shelf. The shelf can establish the separation of the LEDs and photodetectors from the bottom surface of the housing.

FIG. 24B shows a cross-sectional view of sensor probe unit 806, in an implementation. The electrical cable 1604 enters housing 1602 through the housing extension portion 1606 of the housing. The wires of electrical cable 1604 are connected to a PCB 1652. PCB 1652 can be relatively thin, such that the PCB is configured to flex. The flex PCB 1652 is connected to PCB 1650 via the mezzanine connector 2222. The flex of the PCB 162 allows the electrical cable and wires to be pulled or pushed relative to housing 1602 so that any strain from the electrical cable is not transferred to PCB 1650.

In the implementation, the electrical cable is above the flex PCB 1652 and on the opposite side of the flex PCB from the mezzanine connector. The flex PCB 1652 is above the PCB 1650 and is on the opposite side of PCB 1650 from the LEDs, AFE IC, photodetectors mounted on PCB 1650. In an implementation, the PCB is attached to a shelf portion 1602*a* of the housing. The PCB can be adhered to the shelf. The shelf can establish the separation of the LEDs and photodetectors from the bottom surface of the housing.

Figure 25:
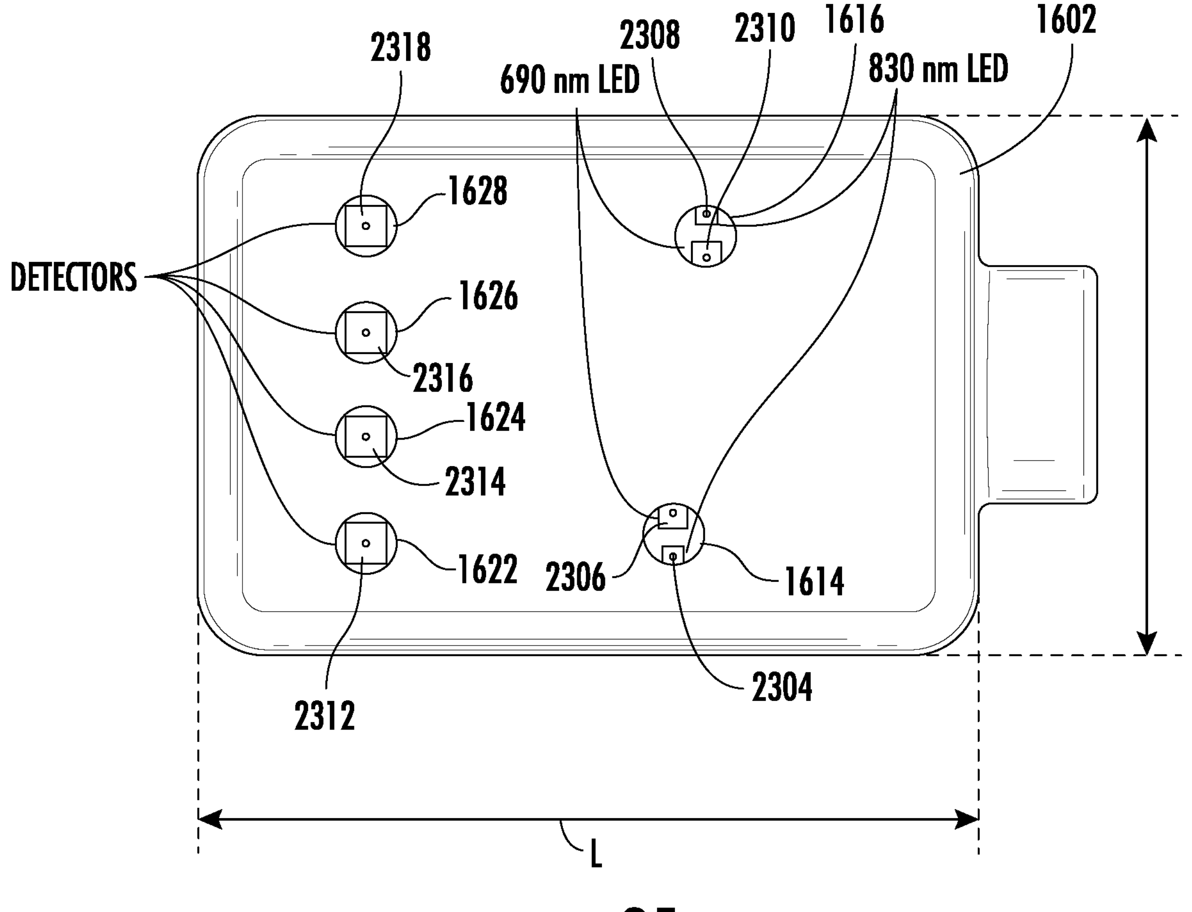
FIG. 25 shows a bottom view of the housing, in an implementation.

FIG. 25 shows a bottom view of the housing 1602, in an implementation. Aperture 1614 and the window material in the aperture are located under (i.e., exposed in an implementation where the window is translucent) a portion of LED 2306, under a portion of LED 2304, and under an area between two LEDs. Aperture 1616 and the window material in the aperture are located under (i.e., exposed in an implementation where the window is translucent) a portion of LED 2308, under a portion of LED 2310, and under an area between two LEDs.

In an implementation, a beam combiner is located in housing 1602 that is optically coupled to LEDs 2304 and 2306 and aperture 1614 and the window in this aperture (source structure S1). More specifically, the beam combiner is located optically between LEDs 2304 and 2306 and aperture 1614 and the window in this aperture (source structure S1). The beam combiner receives light generated and transmitted from LEDs 2304 and 2306 and further transmits the light to aperture 1614 and the window in this aperture (source structure S1) for transmission from the sensor probe unit 806. The beam combiner can be an optical fiber type beam combiner or another type of beam combiner.

In an implementation, a beam combiner is located in housing 1602 that is optically coupled to LEDs 2308 and 2310 and aperture 1616 and the window in this aperture (source structure S1). More specifically, the beam combiner is located optically between LEDs 2308 and 2310 and aperture 1616 and the window in this aperture (source structure S1). The beam combiner receives light generated and transmitted from LEDs 2308 and 2310 and further transmits the light to aperture 1616 and the window in this aperture (source structure S1) for transmission from the sensor probe unit 806. The beam combiner can be an optical fiber type beam combiner or another type of beam combiner.

Aperture 1622 and the window material in the aperture are located under (i.e., exposed in an implementation where the window is translucent) a portion of photodetector 2312. The diameter of the aperture may be less than the length of the diagonal of the photodetector, and the corners of the photodetector may not be viewed through the aperture and window. Aperture 1624 and the window material in the aperture are located under (i.e., exposed in an implementation where the window is translucent) a portion of photodetector 2314. The diameter of the aperture may be less than the length of the diagonal of the photodetector, and the corners of the photodetector may not be viewed through the aperture and window. Aperture 1626 and the window material in the aperture are located under (i.e., exposed in an implementation where the window is translucent) a portion of photodetector 2316. The diameter of the aperture may be less than the length of the diagonal of the photodetector, and the corners of the photodetector may not be viewed through the aperture and window. Aperture 1628 and the window material in the aperture are located under (i.e., exposed in an implementation where the window is translucent) a portion of photodetector 2318. The diameter of the aperture may be less than the length of the diagonal of the photodetector, and the corners of the photodetector may not be viewed through the aperture and window.

Figure 26:
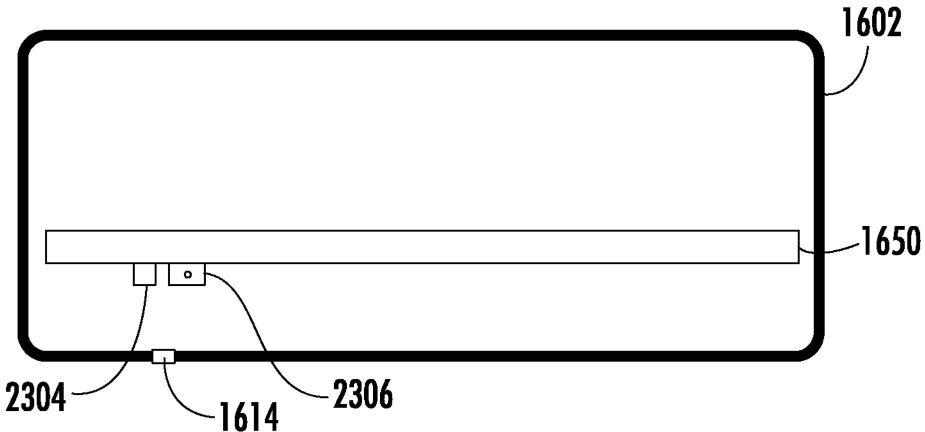
FIG. 26 shows a cross-sectional view of the sensor probe unit, in an implementation.

FIG. 26 shows a cross-sectional view of the sensor probe unit 806, in an implementation. The cross-section is across the width (W in FIG. 25) of housing 1602 through the center of aperture 1614 and the LEDs 2304 and 2306. FIG. 26 shows that aperture 1614 and the window material in the aperture are located under a portion of LED 2306, under a portion of LED 2304, and under an area between two LEDs.

Figure 27:
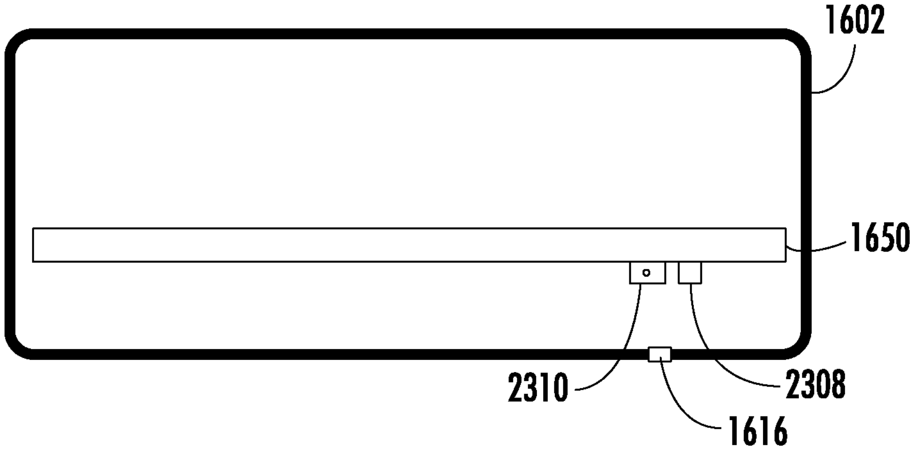
FIG. 27 shows a cross-sectional view of the sensor probe unit, in an implementation.

FIG. 27 shows a cross-sectional view of the sensor probe unit 806, in an implementation. The cross-section is across the width (W in FIG. 25) of housing 1602 through the center of aperture 1616 and the LEDs 2308 and 2310. FIG. 27 shows that aperture 1616 and the window material in the aperture are located under a portion of LED 2310, under a portion of LED 2308, and under an area between two LEDs.

Figure 28:
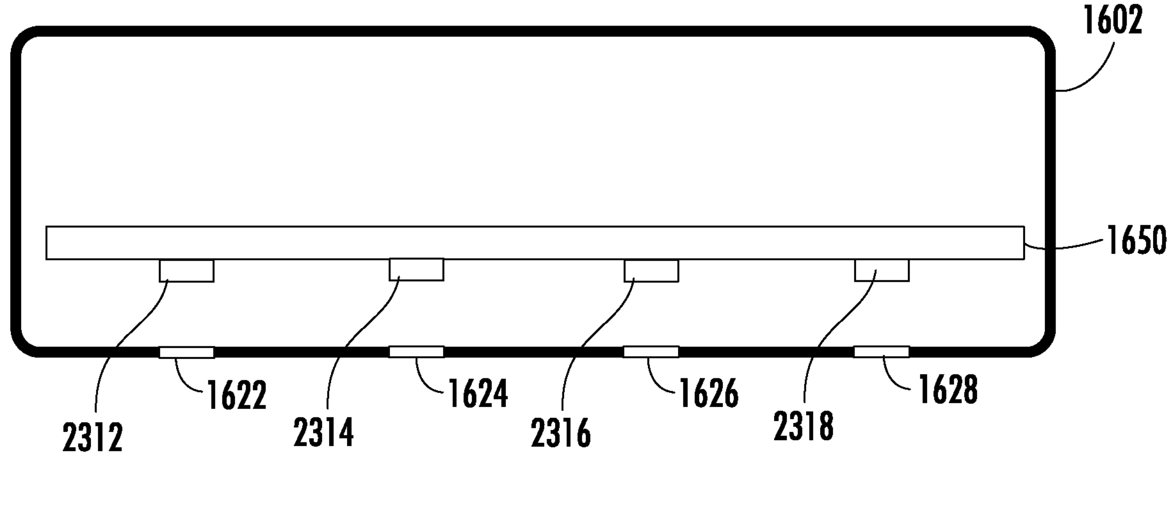
FIG. 28 shows a cross-sectional view of the sensor probe unit, in an implementation.

FIG. 28 shows a cross-sectional view of the sensor probe unit 806, in an implementation. The cross-section is across the length (L in FIG. 25) of housing 1602 through the center of apertures 1622, 1624, 1626, and 1628, and the photodetectors 2312, 2314, 2316, and 2318. FIG. 28 shows that the apertures are under the photodetectors, and the diameters of the apertures are larger than the widths of the photodetectors.

Figure 29:
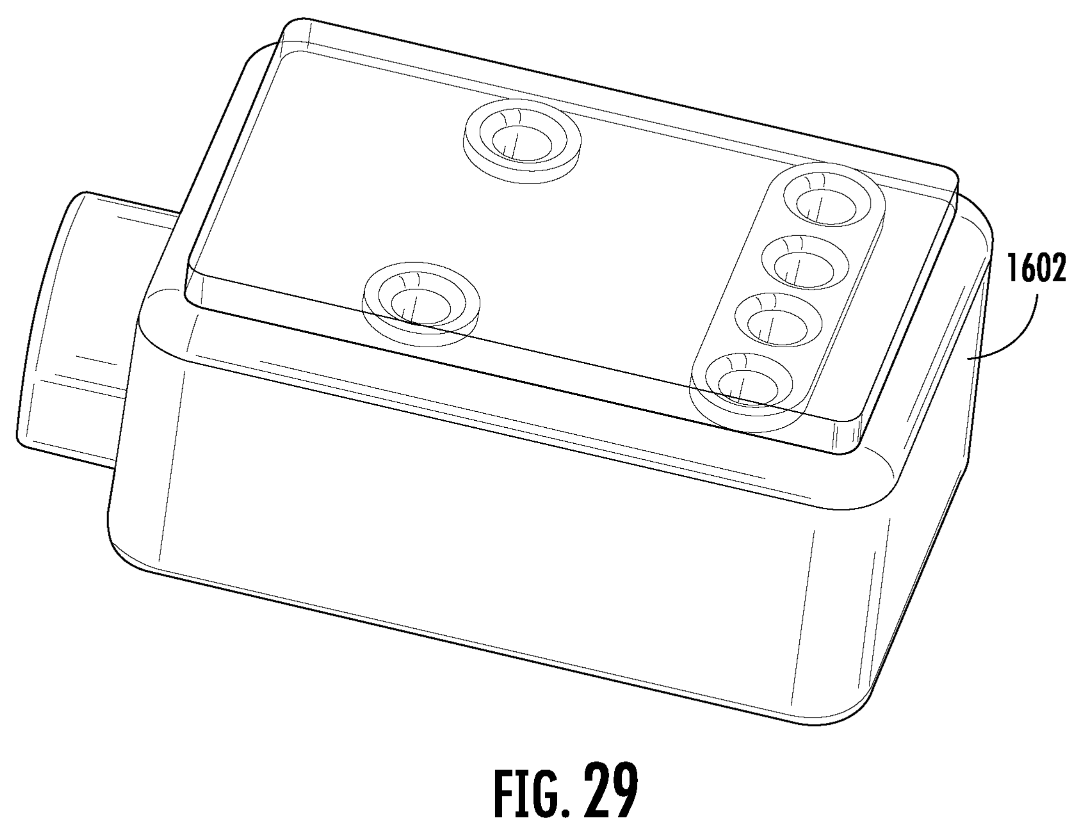
FIG. 29 shows a perspective bottom view of the bottom of the housing before the surface of the bottom of the housing is polished to a planar surface.

In an implementation, the outside surface of the bottom of the housing is planar. FIG. 29 shows a perspective bottom view of the bottom of the housing before the surface of the bottom of the housing is polished to a planar surface. In the implementation, the housing and window material can be injection modeled by injecting the black material of the housing and the translucent or semitranslucent window material. A portion of the window material is polished down so that the outer surfaces of the windows are planar with the bottom of the housing.

Figure 30A:
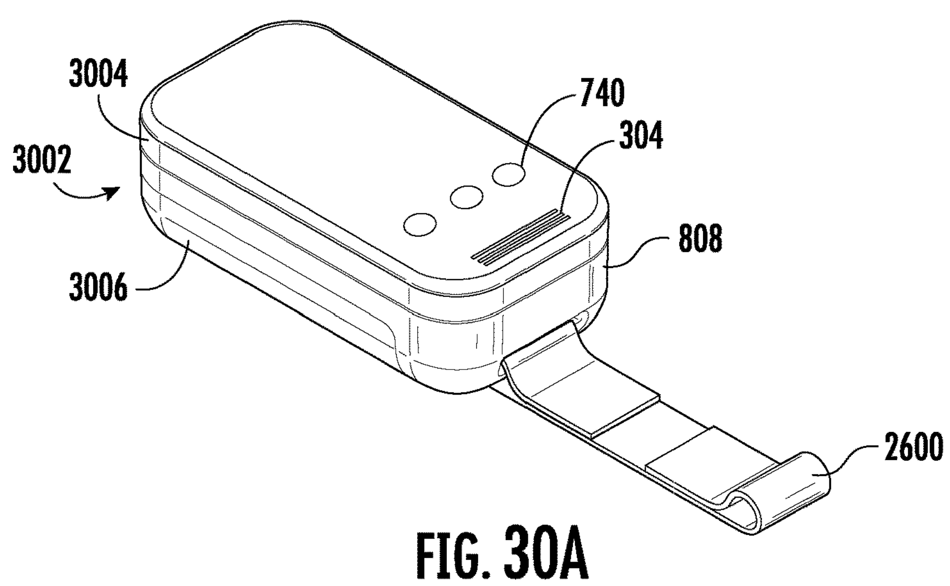
FIGS. 30A-30C show a perspective view, a top view, and a side view of the sensor probe electronic module, in an implementation.
Figure 30B:
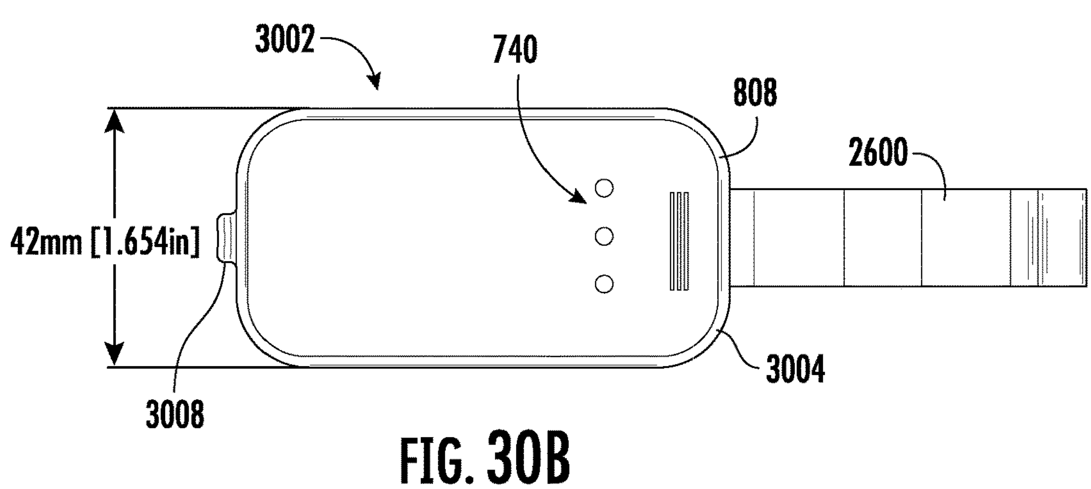
Figure 30C:
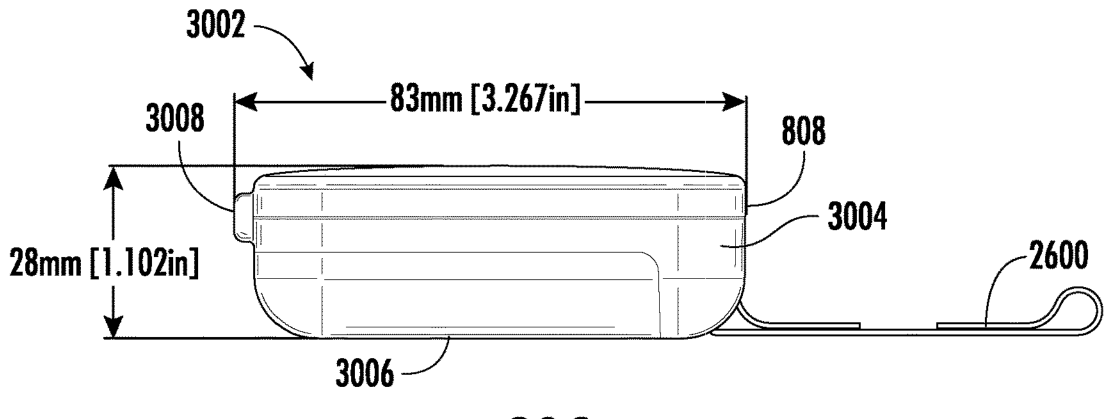

FIGS. 30A-30C show a perspective view, a top view, and a side view of the sensor probe electronic module 808, in an implementation. The module includes a housing 3002 (sometimes referred to as a case or a second enclosure), which is separate and independent from housing 1602 (e.g., the first enclosure). The housing 3002 includes a top portion 3004 and a bottom portion that forms a battery door (or battery lid) 3006. The battery door can be opened or otherwise removed from the top portion of the housing to expose a battery compartment located in the housing. The housing can have a height of about 28 millimeters (1.102 inches), a length of about 83 millimeters (3.276 inches), and a width of about 42 millimeters (1.654 inches), in an implementation. The housing can have other heights, lengths, and widths in other implementations.

A top wall 3008 of the housing includes the visual indicators 740. The visual indicators can include thinned portions (e.g., three thinned portions) of the top wall where the lights (e.g., LEDs) are located below the thinned portions of the top wall. The LEDs are connected to the processor and can be lighted to provide information, such as an identifier for the sensor probe electronic module. For example, if three oximeter devices are connected to a patient, the first probe might have a left-most visual indicator lighted to indicate the first probe, the second probe might have a middle visual indicator lighted to indicate the second probe, and the third probe might have a right-most visual indicator lighted to indicate the third probe.

The connecting surfaces between the sidewalls of the housing and the top wall housing can be rounded for comfort of handling. The connecting surfaces between the sidewalls of the housing and the bottom wall housing can be rounded for comfort of handling.

The housing can include a strap 2600. The strap can be used to attach the sensor probe electronic module to a patient, for example, when the patient is mobile.

Figure 31:
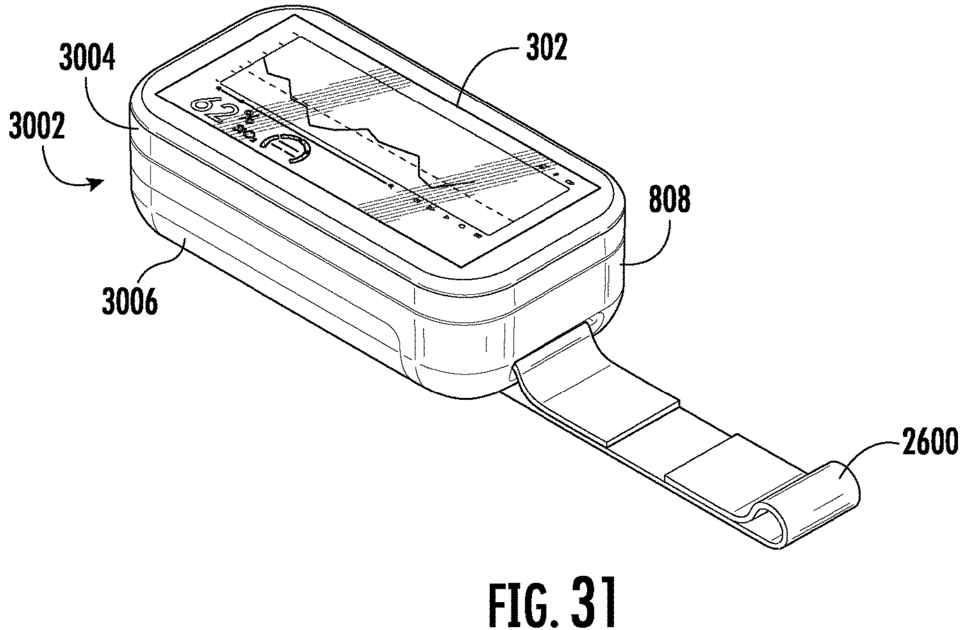
FIGS. 31-32 show a perspective view and a top view of a sensor probe electronic module that includes a display, in an implementation.
Figure 32:
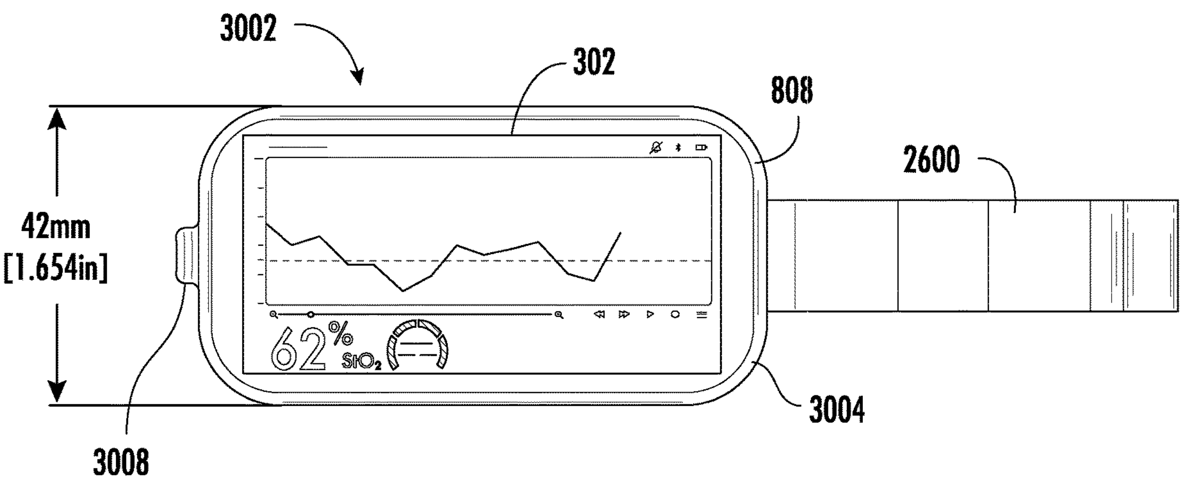

FIGS. 31-32 show a perspective view and a top view a sensor probe electronic module that includes a display 302, in an implementation. The display can be one of a variety of display types, such as an organic light-emitting diode (OLED) display, an active matrix OLED, a liquid crystal display (LCD), a thin film transistor (TFT) display, E-paper display, a micro-LED display, a mini-LED display, a segmented/character LCD display, a transflective display, or another type of display. The display can be controlled by the processor to display oximetry information generated by the oximeter device. The display can display the same oximetry information displayed on the medical device controller, as shown in FIG. 9 and described above or can display a portion of this oximetry information.

Figure 33:
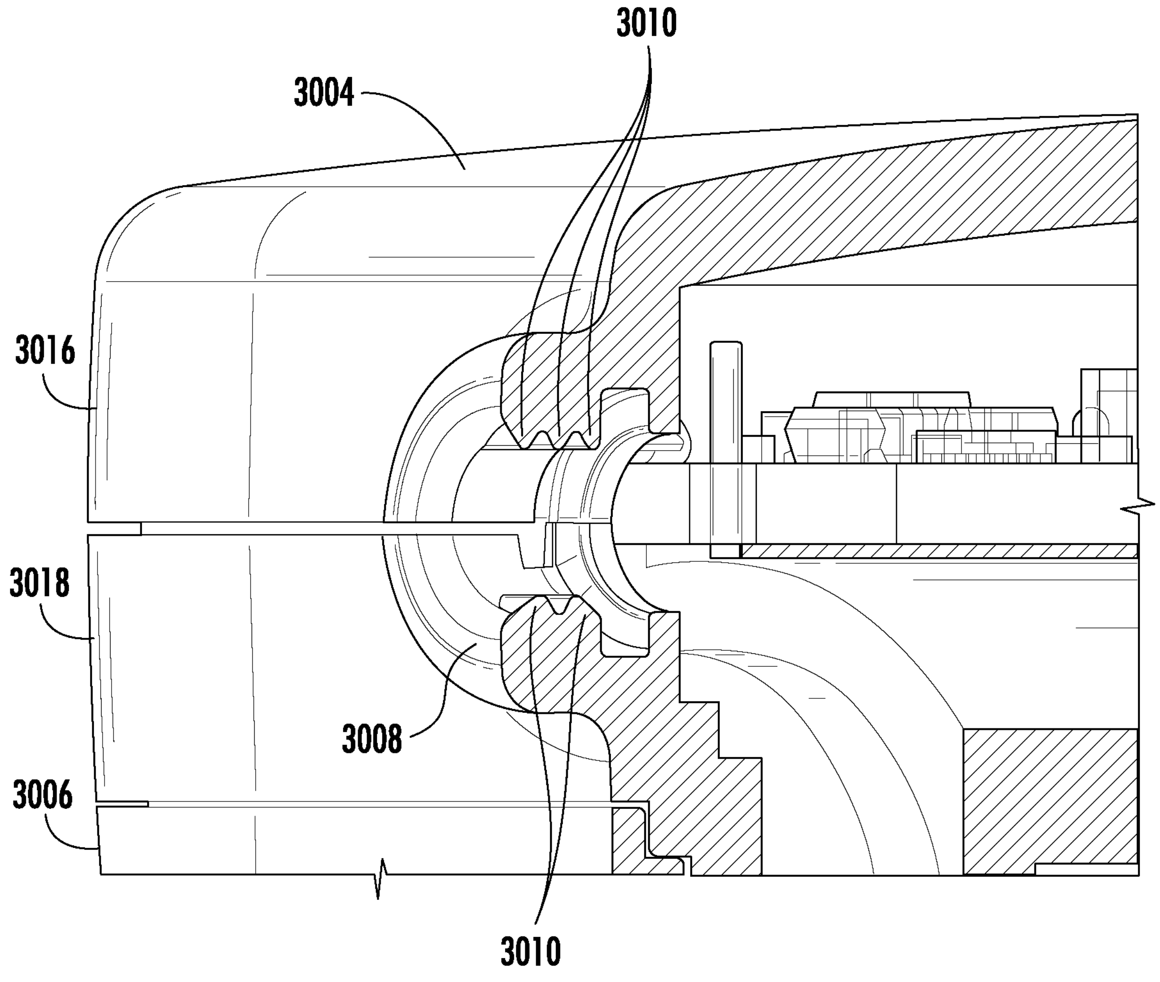
FIG. 33 shows an end view of a portion of a housing of the sensor probe electronic module.

FIG. 33 shows an end view of a portion of housing 3004. The housing includes an extension 3008 where electrical cable 1604 can be connected to the housing. Internal surfaces of the extension can include ribs 3010 that clamp the electrical cable in place to provide strain relief for the wire. A top portion 3016 of housing 3004 can include more or fewer ribs than a bottom portion 3018 of the housing. For example, a top portion of the housing can include three ribs and the bottom portion of the housing can include two ribs. The ribs can be offset, such that the two ribs in the bottom portion align with grooves between the three ribs in the top portion, so that the electrical cable can be partially deformed by the offset rigs providing increased strain relief.

Figure 34:
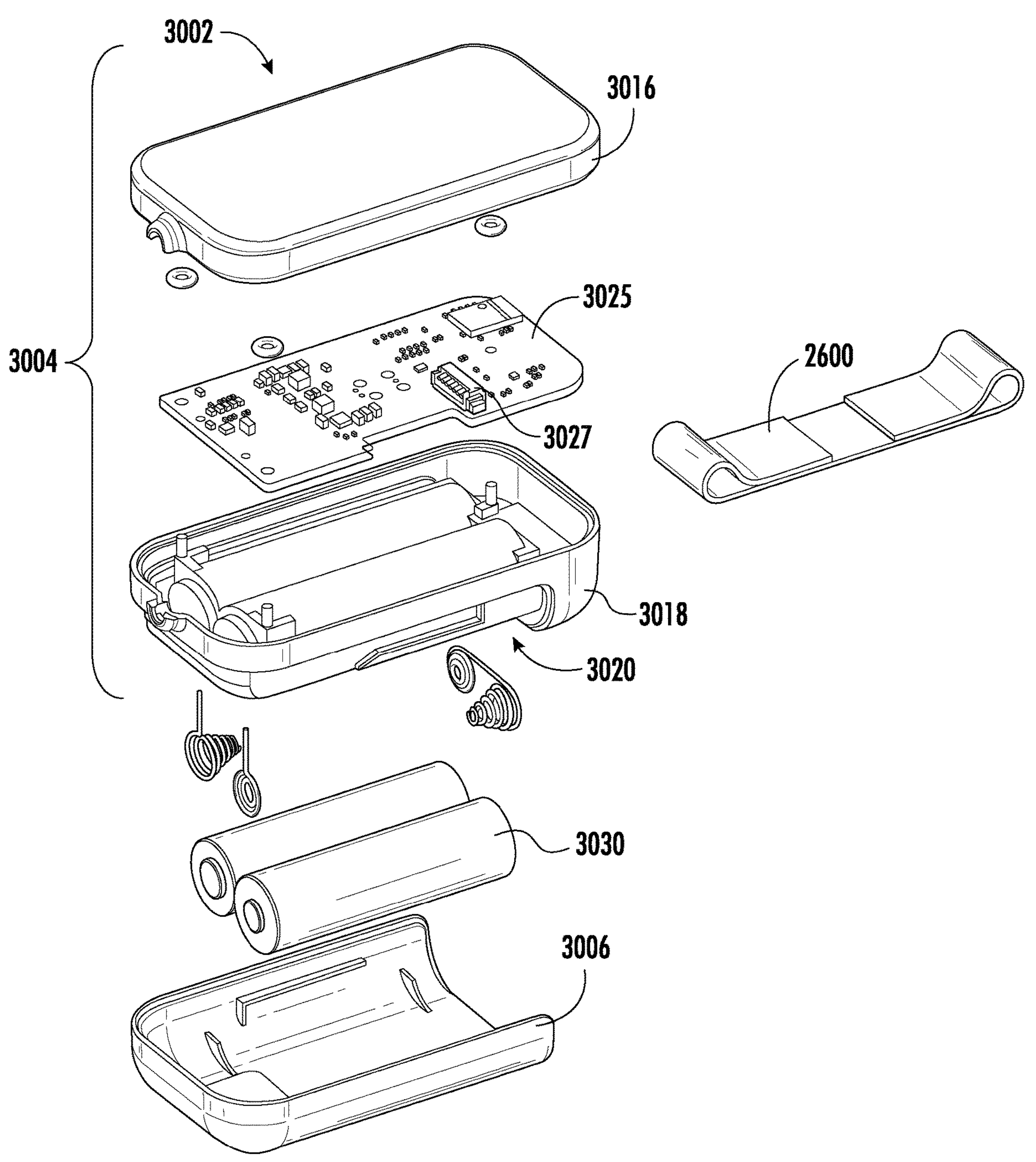
FIG. 34 shows an exploded view of a housing of the sensor probe electronic module.

FIG. 34 shows an exploded view of housing 3002 (sometimes referred to as a battery holder). The housing 3004 houses a PCB 3025 between the top portion 3016 and bottom portion 3018 of housing 3004. The PCB includes a connector 3027 (e.g., an edge connector) located on the top surface of the PCB. Electrical cable 1604 can include a connector (e.g., an edge connector) that mates with connector 3027.

The bottom portion 3018 of housing 3004 forms a battery compartment 3020 configured to hold batteries 3030. The battery compartment has positive and negative terminals that connect to the circuits housed in the housing, such as the processor, memory, wireless communication circuit, display, camera, and other circuits. The battery cover 3006 can cover the battery compartment. The battery compartment 3020 or battery cover 3006 can includes indicators for the battery terminals, such as + (i.e., plus signs) for one or more positive terminals and – (i.e., minus signs) for one or more negative battery terminals so that a user (e.g., a sterile nurse or a scrub nurse) can easily put one or more batteries in the battery housing before a medical procedure (e.g., a breast reconstruction surgery) or after the medical procedure during recovery from the procedure.

In an implementation, battery cover 3006 can be removed from housing 3004 that houses the PCB 3025 without removal of or repositioning the PCB. Further, one or more batteries can be put into the battery holder and removed from the battery holder without removal or repositioning of the PCB.

Figures 35, 36, 37:
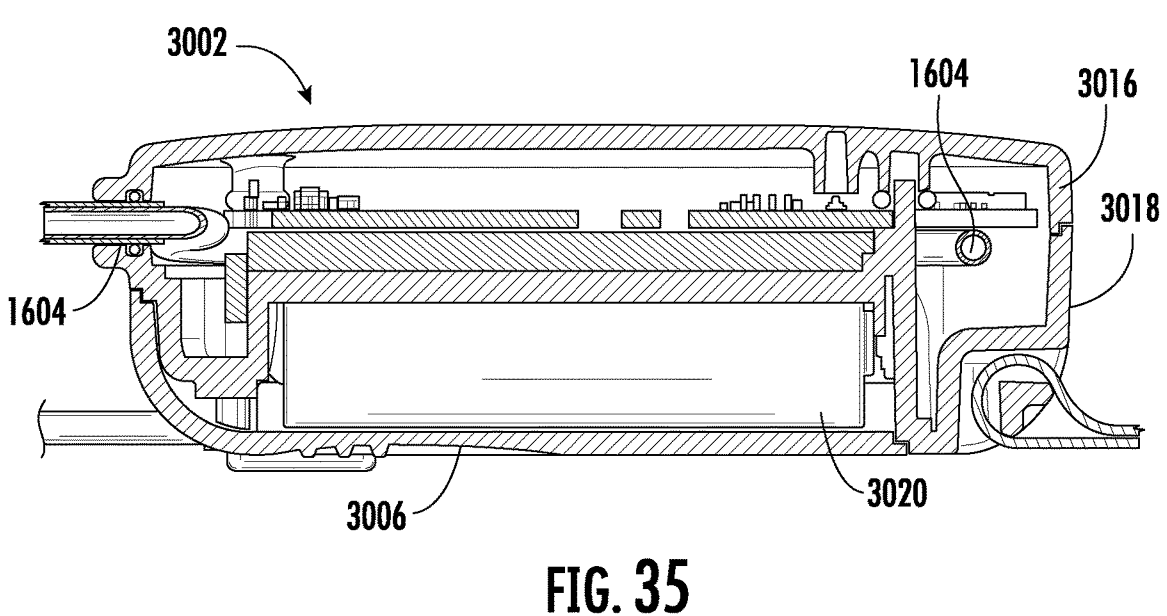
FIG. 35 shows a cross-sectional view of the housing of the sensor probe electronic module.
FIGS. 36-37 show the cable extending around a peripheral portion of the housing of the sensor probe electronic module.

FIG. 35 shows a cross-sectional view of housing 3002 through the battery holder 3020. Electrical cable 1604 extends through a channel formed by the top portion 3016 and bottom portion 3018 of housing 3004, in an implementation. The electrical cable connects the circuits in the sensor probe unit 806, such as the analog front end circuit, the LEDs, and the photodetectors, to the circuits in the sensor probe electronic module 808, such as the processor, the memory, the wireless transmission circuit, the display, and other circuits in this module. FIGS. 36 and 37 show the electrical cable extending around a peripheral portion of the channel where the channel and electrical cable extend from the bottom end of the bottom portion 3018 to the top end of the bottom portion, and extending from the left side of the bottom portion to the right side of the bottom portion where the electrical cable connects to connector 3027. The path of the electrical cable around the peripheral area of housing 3004 provides that the electrical cable makes contact with a number of surfaces inside the housing. The contact provides a relatively high strain relief for the electrical cable without the electrical cable otherwise being fastened inside the housing.

Figure 38:
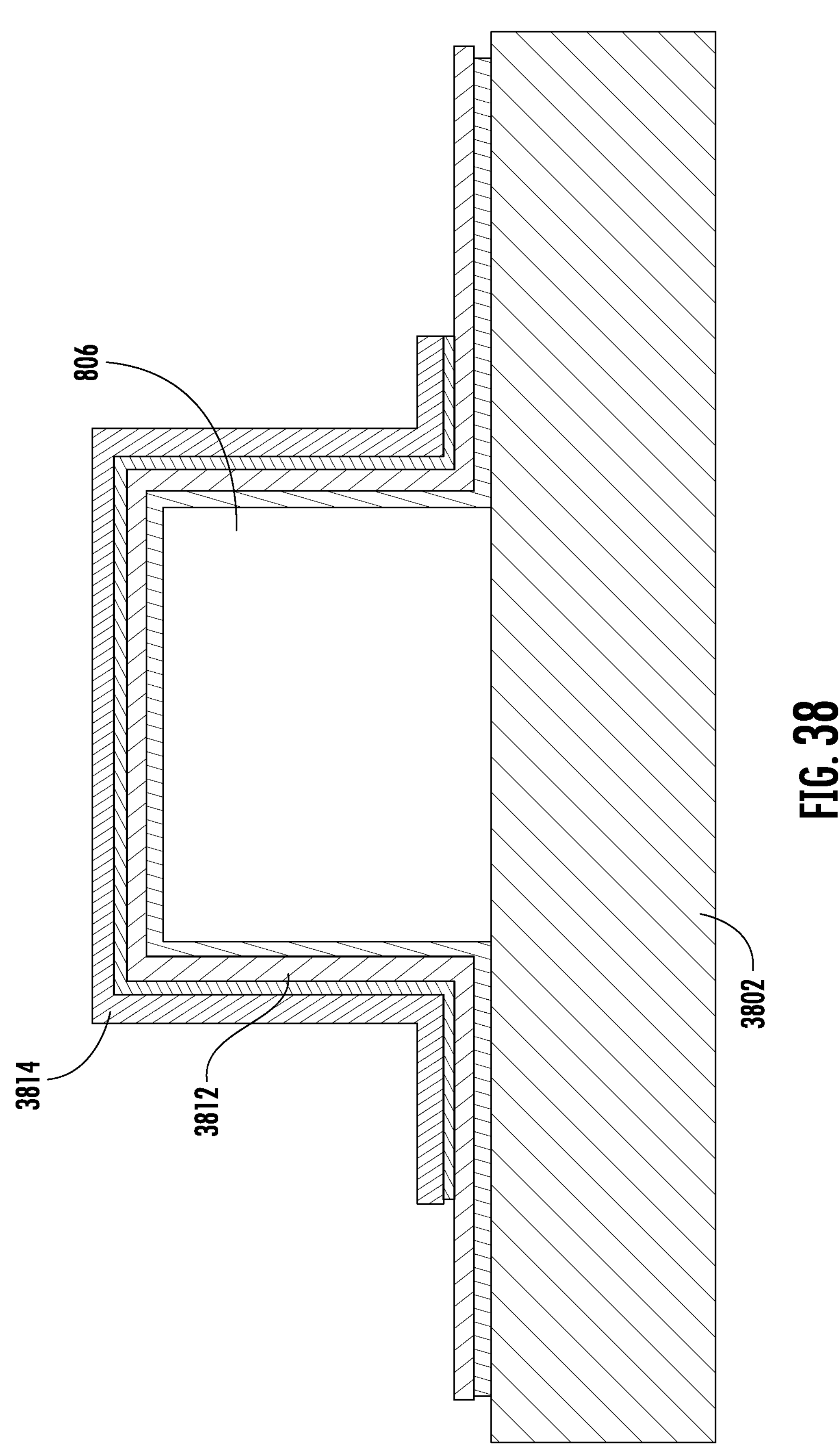
FIG. 38 shows the sensor probe unit of the oximeter device attached to patient tissue, in an implementation.

FIG. 38 shows the sensor probe unit 806 attached to patient tissue 3802, in an implementation. The sensor probe unit 806 is held in place on the tissue by a first adhesive material 3812 that is formed as a relatively thin film. The first adhesive layer can adhere to the sensor probe unit and the patient tissue to hold the sensor probe unit 806 to the tissue. The first adhesive material can have a thickness from about 30 microns to about 100 microns. The first adhesive material may be formed of a breathable, waterproof polyurethane film with an acrylic adhesive. The polyurethane film may be configured to stretch and has a first elasticity. The first adhesive material may be pulled and stretched to release the first adhesive material from patient tissue.

A second adhesive material 3814 is placed over the first adhesive material, in an implementation. The second adhesive material is also a thin film material. The second adhesive material can have a thickness from about 30 microns to about 4500 microns. The second adhesive material can be polyethylene terephthalate (PET) or another material. The second adhesive material has a second elasticity that is less than the first elasticity.

The first and second adhesive materials follow the contour of the sensor probe unit 806 along the top and sides of the housing of the sensor probe unit. The first and second adhesive materials also follow the contour where the housing of the sensor probe unit 806 contacts the patient tissue, such as at an approximately right angle. The lower elasticity of the second adhesive material inhibits the first adhesive material from stretching inadvertently and allowing the sensor probe unit to detach from the patient tissue. The first adhesive material might inadvertently stretch without the second adhesive material over it if the sensor probe unit is accidentally bumped or the patient moves and their body reshapes.

Figure 39:
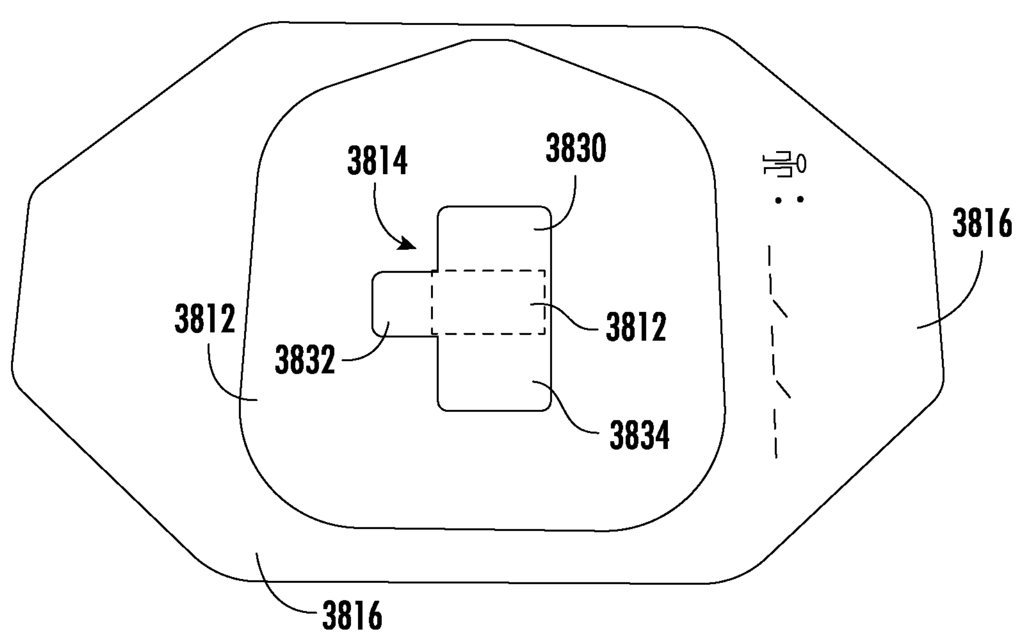
FIG. 39 shows a first adhesive material connected to a package and shows the second adhesive material connected to the first adhesive material.

FIG. 39 shows the first adhesive material 3812 connected to a package 3816 and shows the second adhesive material 3814 connected to the first adhesive material. In FIG. 39, the second adhesive material is above the first adhesive material. The first and second adhesive materials can have different colors. The first and second adhesive materials can be translucent or transparent. The second adhesive material can be smaller than the first adhesive material.

Figure 40:
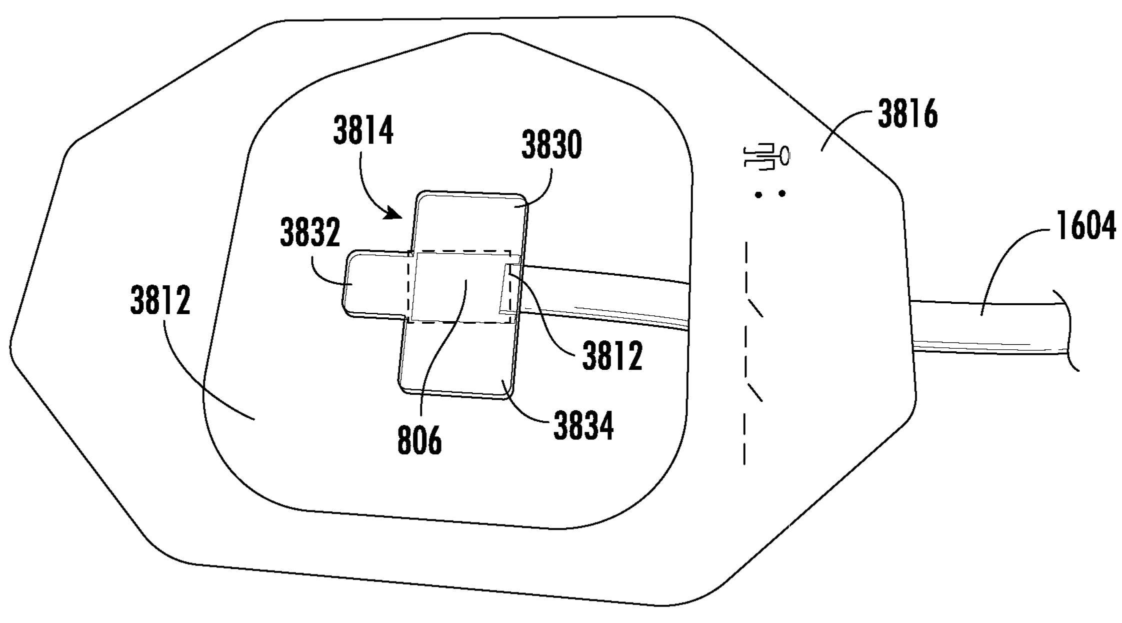
FIG. 40 shows the sensor probe unit of the oximeter device attached to the adhesive layer of the first adhesive material.

FIG. 40 shows the sensor probe unit 806 attached to the adhesive layer of the first adhesive material. The different colors of the first and second adhesive layers allow the sensor probe unit 806 to be easily placed at central area 3812 (outlined by a broken line) of the second adhesive material where two of the corners of the sensor probe unit align with two of the corners of the second adhesive material. With the corners aligned, the edge of the sensor probe unit nearest to electrical cable 1604 approximately aligns with an edge of the second adhesive material. When the sensor probe unit is positioned as described in the central area 3812, three extended portions 3830, 3832, and 3924 (e.g., wings) of the second adhesive layer extend from three of the edges of the central portion 3818. The three extended portions can be folded to adhere the first adhesive material to three sides of the housing of the sensor probe unit.

Figure 41:
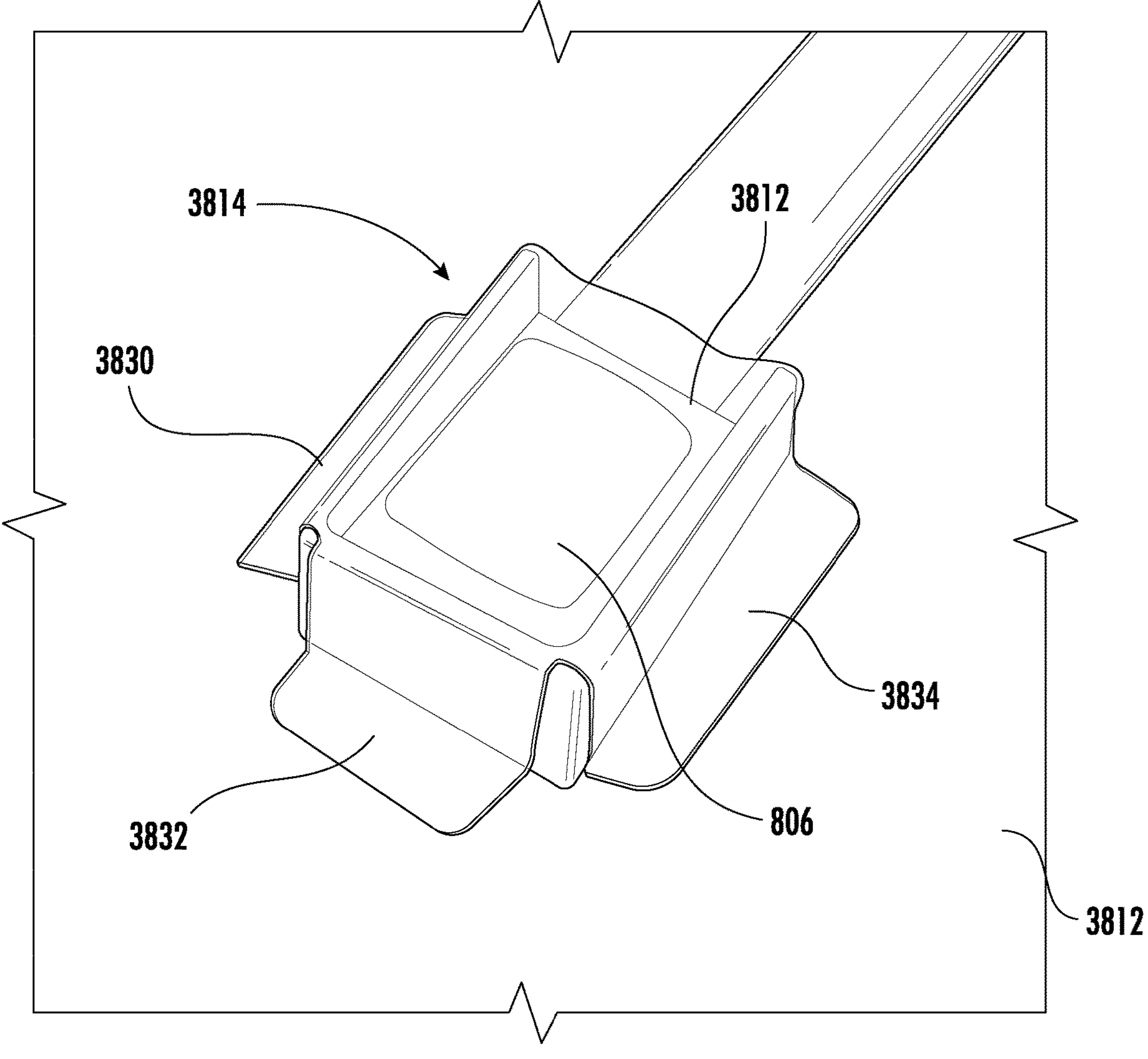
FIG. 41 shows the three extended portions of the second adhesive material folded down, such that the first adhesive material contacts three of the sides of the housing of the sensor probe unit.

FIG. 41 shows the extended portions 3830, 3832, and 3924 of the second adhesive material 3814 folded down, such that the first adhesive material 3812 contacts three of the sides of the housing of the sensor probe unit.

Figure 42:
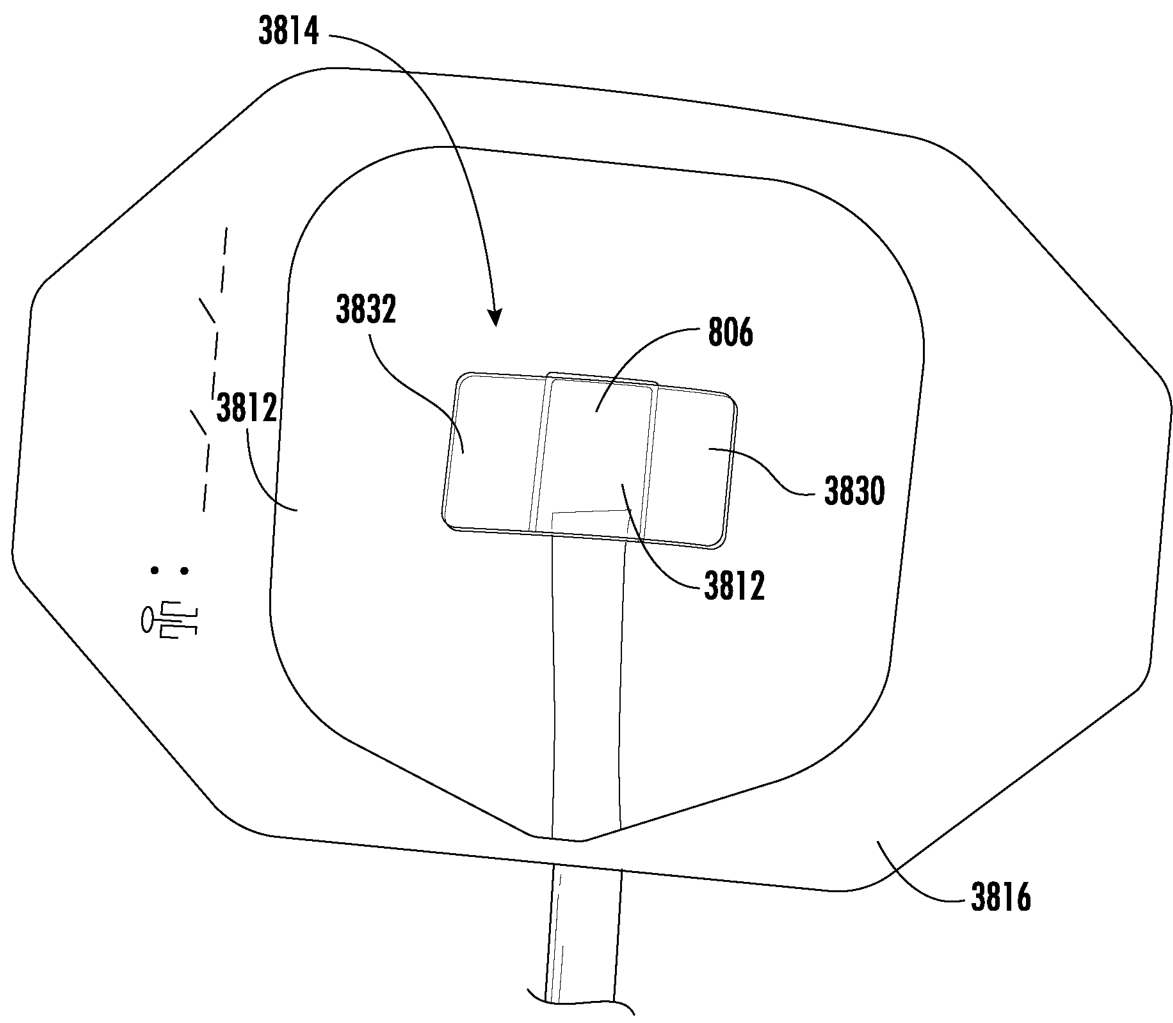
FIG. 42 shows a configuration of the second adhesive material where the material includes two extended portions that extend from the central portion of the second adhesive material, in an implementation.

FIG. 42 shows a configuration of the second adhesive material 3814 where the material includes two extended portions 3830 and 3832 that extend from the central portion 3812, in an implementation.

In an implementation, the oximeter device is packed in a kit that includes batteries that can be inserted into the sensor probe electronic module 808. The batteries are not inserted in the sensor probe electronic module in the kit. The kit can include a user guide that provides instructions to a user how to insert the batteries into the module 808. The batteries can include at least two AA batteries for an end user (e.g., medical professional) to install in module 808.

The following are incorporated by reference along with all other references cited in this application: all patent applications of ViOptix, Inc. published or issued in the U.S. or abroad with a filing date before the filing date of the present application, including U.S. Pat. No. 6,587,703, filed Jun. 7, 2001; U.S. Pat. No. 7,657,293, filed Sep. 8, 2005; U.S. Pat. No. 8,352,006, filed Jun. 24, 2007; U.S. Pat. No. 7,525,647, filed Dec. 21, 2007; U.S. Pat. No. 8,929,967, filed Apr. 28, 2008; U.S. Pat. Nos. 7,553,285, 7,569,017, 7,582,060, filed Jul. 9, 2008; U.S. Pat. No. 10,548,526, filed Jan. 6, 2014; 10,335,074, Jan. 5, 2015; U.S. Pat. No. 11,457,812, filed Aug. 6, 2019, and U.S. patent applications 63/624,782, filed Jan. 24, 2024 and Ser. No. 19/036,800, filed Jan. 24, 2025.

This description of the invention has been presented for the purposes of illustration and description. It is not intended to be exhaustive or to limit the invention to the precise form described, and many modifications and variations are possible in light of the teaching above. Elements of the various implementations can be used with other implementations in a number of ways, such as combinations, substitutions, or both. The implementations were chosen and described in order to best explain the principles of the invention and its practical applications. This description will enable others skilled in the art to best utilize and practice the invention in various implementations and with various modifications as are suited to a particular use. The scope of the invention is defined by the following claims.

What is claimed is:

1. A method comprising:

providing a kit comprising:

providing a first enclosure of an oximeter sensor comprising:

forming a first source structure and a second source structure on a first line on a first planar surface of the first enclosure, wherein the first source structure comprises a first source structure side, inside the first enclosure, and a second source structure side, outside of the first enclosure, and the second source structure comprises a third source structure side, inside the first enclosure, and a fourth source structure side, outside of the first enclosure;

providing a first emitter circuit, wherein the first emitter circuit emits light having a first wavelength, and the first emitter circuit is associated with the first source structure;

providing a second emitter circuit, wherein the second emitter circuit emits light having a second wavelength, which is different from the first wavelength, and the second emitter circuit is associated with the first source structure;

providing a third emitter circuit, wherein the third emitter circuit emits light having the first wavelength, and the third emitter circuit is associated with the second source structure;

providing a fourth emitter circuit, wherein the fourth emitter circuit emits light having the second wavelength, and the fourth emitter circuit is associated with the second source structure, the first and second emitter circuits are positioned within the first enclosure such that light emitted by either the first emitter circuit or the second emitter circuit will pass through the first source structure from the first source structure side to the second source structure side in a direction away from the first planar surface, and the third and fourth emitter circuits are positioned within the first enclosure such that light emitted by either the third emitter circuit or the fourth emitter circuit will pass through the second source structure from the third source structure side to the fourth source structure side in a direction away from the first planar surface;

forming a first detector structure and a second detector structure on a second line on the first planar surface of the first enclosure, where the second line is not collinear or parallel with the first line, and the second line does not pass through the first source structure or the second source structure;

providing a first detector circuit, wherein the first detector circuit receives light that passes through the first detector structure and not the second detector structure;

providing a second detector circuit, wherein the second detector circuit receives light that passes through the second detector structure and not the first detector structure; and coupling a front-end circuit to the first and second emitter circuits and the first and second detector circuits;

providing a second enclosure of the oximeter sensor, wherein the second enclosure is a separate and independent enclosure from the first enclosure;

providing a processor in the second enclosure;

providing a memory in the second enclosure and coupling the memory to the processor;

providing a first wireless communication circuit and coupling the first wireless communication circuit to the processor and memory;

providing a battery holder comprising positive and negative battery terminals;

coupling the battery terminals to the processor, memory, and first wireless communication circuit via a connection to the second enclosure;

externally extending an electrical cable between the first and second enclosures;

coupling the electrical cable from the front-end circuit of the first enclosure to the processor, memory, wireless communication circuit, and battery-holder battery terminals of the second enclosure; and providing a battery that is compatible with the battery holder of the second enclosure, wherein as part of the kit, the battery is not installed in the battery holder.

2. The method of claim 1 comprising:

providing a user guide, wherein the user guide provides instructions on how to install the battery into the battery holder.

3. The method of claim 1 wherein the battery comprises at least two AA batteries.

4. The method of claim 1 wherein an end user installs the battery into the battery holder.

5. The method of claim 1 comprising providing a first distance between the first source structure and the first detector structure, a second distance between the first source structure and the second detector structure, a third distance between the second source structure and the first detector structure, and a fourth distance between the second source structure and the second detector structure, wherein the first, second, third, and fourth distances are different from each other.

6. The method of claim 1 comprising providing the first enclosure comprises a third detector structure and a fourth detector structure arranged on the second line on the first planar surface of the first housing.

7. The method of claim 1 wherein the first and second source structures and the first and second detector structures comprise circular cross sections.

8. The method of claim 1 wherein the first and second source structures and the first and second detector structures comprise a polymer material.

9. The method of claim 1 wherein the first and second source structures and the first and second detector structures comprise optical fibers.

10. The method of claim 1 comprising:

providing a beam combiner comprising a first input, second input, and an output;

optically coupling the first input of the beam combiner to the first emitter circuit;

optically coupling the second input of the beam combiner to the second emitter circuit; and optically coupling the output of the beam combiner to the first source structure.

11. The method of claim 1 wherein the first and second emitter circuits are positioned within the first enclosure such that while light emitted by either the first emitter circuit or the second emitter circuit is passing through the first source structure, that light will not pass through the second source structure.

12. The method of claim 11 wherein the third and fourth emitter circuits are positioned within the first enclosure such that while light emitted by either the third emitter circuit or the fourth emitter circuit is passing through the second source structure, that light will not pass through the first source structure.

13. The method of claim 1 wherein the second enclosure comprises a battery compartment, comprising the battery holder; and providing a battery cover, which removably interlocks with the second enclosure to cover the battery compartment.

14. The method of claim 1 wherein the battery compartment comprises a first holder for a first battery cell and a second holder for a second battery cell, and the first and second holders comprise electrical connections that will couple the first battery cell and second battery cell together in series.

15. A method comprising:

providing a kit comprising:

providing a first enclosure of an oximeter probe comprising:

forming a first source structure and a second source structure on a first line on a first planar surface of the first enclosure, wherein the first source structure comprises a first source structure side, inside the first enclosure, and a second source structure side, outside of the first enclosure, and the second source structure comprises a third source structure side, inside the first enclosure, and a fourth source structure side, outside of the first enclosure;

providing a first emitter circuit, wherein the first emitter circuit emits light having a first wavelength, and the first emitter circuit is associated with the first source structure;

providing a second emitter circuit, wherein the second emitter circuit emits light having a second wavelength, which is different from the first wavelength, and the second emitter circuit is associated with the first source structure;

providing a third emitter circuit, wherein the third emitter circuit emits light having the first wavelength, and the third emitter circuit is associated with the second source structure;

providing a fourth emitter circuit, wherein the fourth emitter circuit emits light having the second wavelength, and the fourth emitter circuit is associated with the second source structure, the first and second emitter circuits are positioned within the first enclosure such that light emitted by either the first emitter circuit or the second emitter circuit will pass through the first source structure from the first source structure side to the second source structure side in a direction away from the first planar surface, and the third and fourth emitter circuits are positioned within the first enclosure such that light emitted by either the third emitter circuit or the fourth emitter circuit will pass through the second source structure from the third source structure side to the fourth source structure side in a direction away from the first planar surface;

forming a first detector structure and a second detector structure on a second line on the first planar surface of the first enclosure, where the second line is not collinear or parallel with the first line;

providing a first detector circuit, wherein the first detector circuit receives light that passes through the first detector structure and not the second detector structure;

providing a second detector circuit, wherein the second detector circuit receives light that passes through the second detector structure and not the first detector structure; and coupling a front-end circuit to the first and second emitter circuits and the first and second detector circuits;

providing a second enclosure of the oximeter probe, wherein the second enclosure is a separate and independent enclosure from the first enclosure;

providing a processor in the second enclosure;

providing a memory in the second enclosure and coupling the memory to the processor;

providing a first wireless communication circuit and coupling the first wireless communication circuit to the processor and memory;

providing a battery holder comprising positive and negative battery terminals;

coupling the battery terminals to the processor, memory, and first wireless communication circuit via a connection to the second enclosure;

externally extending an electrical cable between the first and second enclosures;

coupling the electrical cable from the front-end circuit of the first enclosure to the processor, memory, wireless communication circuit, and battery-holder battery terminals of the second enclosure;

providing a battery that is compatible with the battery holder of the second enclosure, wherein as part of the kit, the battery is not installed in the battery holder;

positioning no intervening source or detector structures between the first source structure and the first detector structure;

positioning no intervening source or detector structures between the first source structure and the second detector structure;

positioning no intervening source or detector structures between the second source structure and the first detector structure; and positioning no intervening source or detector structures between the second source structure and the second detector structure.

16. A method comprising:

providing a kit comprising:

providing a first enclosure of an oximeter probe comprising:

forming a first source structure and a second source structure on a first line on a first planar surface of the first enclosure, wherein the first source structure comprises a first source structure side, inside the first enclosure, and a second source structure side, outside of the first enclosure, and the second source structure comprises a third source structure side, inside the first enclosure, and a fourth source structure side, outside of the first enclosure;

providing a first emitter circuit, wherein the first emitter circuit emits light having a first wavelength, and the first emitter circuit is associated with the first source structure;

providing a second emitter circuit, wherein the second emitter circuit emits light having a second wavelength, which is different from the first wavelength, and the second emitter circuit is associated with the first source structure;

providing a third emitter circuit, wherein the third emitter circuit emits light having the first wavelength, and the third emitter circuit is associated with the second source structure;

providing a fourth emitter circuit, wherein the fourth emitter circuit emits light having the second wavelength, and the fourth emitter circuit is associated with the second source structure, the first and second emitter circuits are positioned within the first enclosure such that light emitted by either the first emitter circuit or the second emitter circuit will pass through the first source structure from the first source structure side to the second source structure side in a direction away from the first planar surface, and the third and fourth emitter circuits are positioned within the first enclosure such that light emitted by either the third emitter circuit or the fourth emitter circuit will pass through the second source structure from the third source structure side to the fourth source structure side in a direction away from the first planar surface;

forming a first detector structure and a second detector structure on a second line on the first planar surface of the first enclosure, where the second line is not collinear or parallel with the first line;

providing a first detector circuit, wherein the first detector circuit receives light that passes through the first detector structure and not the second detector structure;

providing a second detector circuit, wherein the second detector circuit receives light that passes through the second detector structure and not the first detector structure; and coupling a front-end circuit to the first and second emitter circuits and the first and second detector circuits;

providing a second enclosure of the oximeter probe, wherein the second enclosure is a separate and independent enclosure from the first enclosure;

providing a processor in the second enclosure;

providing a memory in the second enclosure and coupling the memory to the processor;

providing a first wireless communication circuit and coupling the first wireless communication circuit to the processor and memory;

providing a battery holder comprising positive and negative battery terminals;

coupling the battery terminals to the processor, memory, and first wireless communication circuit via a connection to the second enclosure;

externally extending an electrical cable between the first and second enclosures;

coupling the electrical cable from the front-end circuit of the first enclosure to the processor, memory, wireless communication circuit, and battery-holder battery terminals of the second enclosure;

providing a battery that is compatible with the battery holder of the second enclosure, wherein as part of the kit, the battery is not installed in the battery holder;

positioning no intervening source or detector structures on a line between the first source structure and the first detector structure;

positioning no intervening source or detector structures on a line between the first source structure and the second detector structure;

positioning no intervening source or detector structures on a line between the second source structure and the first detector structure; and positioning no intervening source or detector structures on a line between the second source structure and the second detector structure.

17. A method comprising:

providing a kit comprising:

providing a first enclosure of an oximeter sensor comprising:

forming a first source structure and a second source structure arranged on a first line on a first planar surface of the first enclosure, wherein the first source structure comprises a first source structure side, inside the first enclosure, and a second source structure side, outside of the first enclosure, and the second source structure comprises a third source structure side, inside the first enclosure, and a fourth source structure side, outside of the first enclosure;

providing a first emitter circuit, wherein the first emitter circuit emits light having a first wavelength or a second wavelength, the first wavelength is different from the second wavelength, and the first emitter circuit is associated with the first source structure;

providing a second emitter circuit, wherein the second emitter circuit emits light having the first wavelength or the second wavelength, and the second emitter circuit is associated with the second source structure, the first emitter circuit is positioned within the first enclosure such that light emitted by the first emitter circuit will pass through the first source structure from the first source structure side to the second source structure side in a direction away from the first planar surface, and the second emitter circuit is positioned within the first enclosure such that light emitted by the second emitter circuit will pass through the second source structure from the third source structure side to the fourth source structure side in a direction away from the first planar surface;

forming a first detector structure and a second detector structure arranged on a second line on the first planar surface of the first enclosure, where the second line is not collinear or parallel with the first line, and the second line does not pass through the first source structure or the second source structure;

providing a first detector circuit, wherein the first detector circuit receives light that passes through the first detector structure and not the second detector structure;

providing a second detector circuit, wherein the second detector circuit receives light that passes through the second detector structure and not the first detector structure; and coupling a front-end circuit to the first and second emitter circuits and the first and second detector circuits;

providing a second enclosure of the oximeter sensor, wherein the second enclosure is a separate and independent enclosure from the first enclosure;

providing a processor in the second enclosure;

providing a memory in the second enclosure and coupling the memory to the processor;

providing a first wireless communication circuit in the second enclosure and coupling the first wireless communication circuit to the processor and memory;

providing a battery holder comprising positive and negative battery terminals;

coupling the battery terminals to the processor, memory, and first wireless communication circuit via a connection internal to the second enclosure;

externally extending an electrical cable between the first and second enclosures;

coupling the electrical cable from the front-end circuit of the first enclosure to the processor, memory, wireless communication circuit, and battery-holder battery terminals of the second enclosure; and providing a battery that is compatible with the battery holder of the second enclosure, wherein as part of the kit, the battery is not installed in the battery holder.

18. The method of claim 17 comprising:

providing a user guide, wherein the user guide provides instructions on how to install the battery into the battery holder.

19. The method of claim 17 wherein the battery comprises at least two AA batteries and an end user installs the battery into the battery holder.

20. The method of claim 17 wherein the providing the kit comprises providing a first distance is between the first source structure and the first detector structure, a second distance is between the first source structure and the second detector structure, a third distance is between the second source structure and the first detector structure, and a fourth distance is between the second source structure and the second detector structure, wherein the first, second, third, and fourth distances are different from each other.

* * * * *